(12) United States Patent
O'Donnell, Jr. et al.

(10) Patent No.: US 9,026,372 B2
(45) Date of Patent: May 5, 2015

(54) METHODS FOR PROVIDING A SYSTEM OF CARE FOR A HIGH-DOSE OXAZAPHOSPHORINE DRUG REGIMEN

(75) Inventors: Francis O'Donnell, Jr., Longboat Key, FL (US); Carlos Santos, Tampa, FL (US)

(73) Assignee: Accentia Biopharmaceuticals, Inc., Tampa, FL (US)

( * ) Notice: Subject to any disclaimer, the term of this patent is extended or adjusted under 35 U.S.C. 154(b) by 0 days.

(21) Appl. No.: 12/789,401

(22) Filed: May 27, 2010

(65) Prior Publication Data

US 2011/0082115 A1 Apr. 7, 2011

Related U.S. Application Data

(63) Continuation-in-part of application No. 12/785,224, filed on May 21, 2010, now abandoned, which is a continuation-in-part of application No. PCT/US2008/084396, filed on Nov. 21, 2008, and a continuation-in-part of application No. PCT/US2008/084414, filed on Nov. 21, 2008.

(60) Provisional application No. 60/989,628, filed on Nov. 21, 2007, provisional application No. 61/038,033, filed on Mar. 19, 2008, provisional application No. 61/088,600, filed on Aug. 13, 2008, provisional application No. 61/095,884, filed on Sep. 10, 2008, provisional application No. 61/096,232, filed on Sep. 11, 2008, provisional application No. 61/106,073, filed on Oct. 16, 2008.

(51) Int. Cl.
| | | |
|---|---|---|
| *G01N 33/48* | (2006.01) | |
| *A61K 31/675* | (2006.01) | |
| *G06F 19/00* | (2011.01) | |
| *G06Q 50/22* | (2012.01) | |
| *G06Q 50/24* | (2012.01) | |

(52) U.S. Cl.
CPC .............. *A61K 31/675* (2013.01); *G06F 19/30* (2013.01); *G06Q 50/22* (2013.01); *G06Q 50/24* (2013.01)

(58) Field of Classification Search
CPC ....................................................... G06F 19/30
USPC .......................................................... 702/19
See application file for complete search history.

(56) References Cited

U.S. PATENT DOCUMENTS

| | | |
|---|---|---|
| 4,537,883 A | 8/1985 | Alexander et al. |
| 4,753,965 A | 6/1988 | Stemerick et al. |
| 4,841,085 A | 6/1989 | Farquhar et al. |
| 5,036,060 A | 7/1991 | Alam et al. |
| 5,055,459 A | 10/1991 | Andersson et al. |
| 5,187,266 A | 2/1993 | Farquhar et al. |
| 5,204,369 A | 4/1993 | Vallee et al. |
| 5,413,995 A | 5/1995 | Alexander et al. |
| 5,624,910 A | 4/1997 | Vallee et al. |
| 5,649,904 A | 7/1997 | Gianni |
| 5,866,169 A | 2/1999 | Hausheer et al. |
| 5,876,956 A | 3/1999 | Jones et al. |
| 5,886,028 A | 3/1999 | Vallee et al. |
| 5,914,257 A | 6/1999 | Fukaya et al. |
| 6,121,010 A | 9/2000 | Vallee et al. |
| 6,255,497 B1 | 7/2001 | Vallee et al. |
| 6,268,138 B1 | 7/2001 | Dalla-Favera et al. |
| 6,288,110 B1 * | 9/2001 | Marikovsky .................. 514/483 |
| 6,428,782 B1 | 8/2002 | Slavin et al. |
| 6,447,767 B1 | 9/2002 | Slavin et al. |
| 6,465,436 B2 | 10/2002 | Lukas et al. |
| 6,544,787 B1 | 4/2003 | Slavin |
| 6,558,662 B2 | 5/2003 | Sykes et al. |
| 6,562,347 B1 | 5/2003 | Kwak et al. |
| 6,622,805 B2 | 9/2003 | Nakashima |
| 6,627,759 B1 | 9/2003 | Smith et al. |
| 6,936,599 B2 | 8/2005 | Voskuhl |
| 7,368,434 B2 | 5/2008 | Keung et al. |
| 7,408,039 B2 | 8/2008 | Sykes et al. |
| 7,531,562 B2 | 5/2009 | Fahl et al. |
| 7,754,480 B2 | 7/2010 | Smith et al. |
| 7,892,578 B2 | 2/2011 | Sykes et al. |
| 8,673,321 B2 | 3/2014 | Brodsky et al. |
| 2001/0053362 A1 | 12/2001 | Walters |
| 2002/0048584 A1 | 4/2002 | Pomerantz |
| 2003/0007968 A1 | 1/2003 | Larsen et al. |
| 2003/0073649 A1 | 4/2003 | DiMartino et al. |
| 2003/0099622 A1 | 5/2003 | Hering et al. |
| 2004/0023318 A1 | 2/2004 | Smith et al. |

(Continued)

FOREIGN PATENT DOCUMENTS

| | | |
|---|---|---|
| WO | WO 96/36344 A1 | 11/1996 |
| WO | WO-98/20932 | 5/1998 |

(Continued)

OTHER PUBLICATIONS

Yamada et al., "A New G-CSF-Supported Combination Chemotherapy, ISG15, for Adult T-cell Leukaemia-Lymphoma: Japan Clinical Oncology Group Study 9303" British Journal of Haematology (2001) vol. 113, pp. 375-382.*
Brodsky, R.A. "High Dose Cyclophosphamide Treatment for Autoimmune Disorders" *The Scientific World Journal*, 2002, 2:1808-1815.
Anderson, L.W. et al. "Cyclophosphamide and 4-Hydroxycyclophosphamide/Aldophosphamide Kinetics in Patients Receiving High-Dose Cyclophosphamide Chemotherapy" *Clinical Cancer Research*, Sep. 1996, 2:1481-1487.
Awad, A. et al. "Cyclophosphamide in multiple sclerosis: scientific rationale, history and novel treatment paradigms" *Ther Adv Neurol Disord*, 2009, 2(6):357-368.
"Biovest Secures Worldwide Exclusive License to Late-Stage Technology for Elimination of Transplant Rejection" Press Release, Jan. 22, 2008 at 08:30 AM EST.

(Continued)

*Primary Examiner* — Jerry Lin
(74) *Attorney, Agent, or Firm* — Saliwanchik, Lloyd & Eisenschenk

(57) ABSTRACT

The present invention provides methods of treating subjects with an oxazaphosphorines, methods of identifying subjects that are suitable for oxazaphosphorine treatment, and systems for ensuring the safety and efficacy of a treatment that includes oxazaphosphorine administration.

32 Claims, 5 Drawing Sheets

(56) References Cited

U.S. PATENT DOCUMENTS

| | | |
|---|---|---|
| 2004/0064037 A1* | 4/2004 | Smith .......................... 600/420 |
| 2004/0152630 A1 | 8/2004 | Fu et al. |
| 2004/0214902 A1 | 10/2004 | Wang et al. |
| 2005/0108067 A1* | 5/2005 | Chapman et al. .................. 705/4 |
| 2005/0201980 A1 | 9/2005 | Moran |
| 2005/0272698 A1 | 12/2005 | Daftary et al. |
| 2006/0002930 A1 | 1/2006 | Brunetta et al. |
| 2006/0229233 A1 | 10/2006 | Frenkel et al. |
| 2006/0253263 A1 | 11/2006 | Meshkin |
| 2007/0173442 A1 | 7/2007 | Vollmer |
| 2007/0202077 A1* | 8/2007 | Brodsky et al. .............. 424/85.1 |
| 2011/0092462 A1 | 4/2011 | Brodsky et al. |
| 2011/0097426 A1 | 4/2011 | O'Donnell et al. |
| 2011/0117050 A1 | 5/2011 | O'Donnell et al. |
| 2011/0123482 A1 | 5/2011 | Kaplin et al. |
| 2011/0212052 A1 | 9/2011 | Kaplin |
| 2012/0100162 A1 | 4/2012 | Brodsky et al. |
| 2012/0128685 A1 | 5/2012 | Brodsky et al. |
| 2012/0129206 A1 | 5/2012 | Brodsky et al. |
| 2012/0148611 A1 | 6/2012 | Brodsky et al. |
| 2012/0237472 A1 | 9/2012 | Kaplin et al. |

FOREIGN PATENT DOCUMENTS

| | | |
|---|---|---|
| WO | WO 98/42378 A1 | 10/1998 |
| WO | WO 99/42099 A1 | 8/1999 |
| WO | WO 00/27428 A1 | 5/2000 |
| WO | WO-00/40701 | 7/2000 |
| WO | WO 00/74718 A1 | 12/2000 |
| WO | WO-2005/057213 | 6/2005 |
| WO | WO 2007/065167 | 6/2007 |
| WO | WO 2008/034071 | 3/2008 |
| WO | WO 2008/034071 A2 | 3/2008 |
| WO | WO 2008/034074 A2 | 3/2008 |
| WO | WO 2008/034076 A2 | 3/2008 |
| WO | WO 2008/156494 A1 | 12/2008 |
| WO | WO 2009/045464 A1 | 4/2009 |
| WO | WO-2009/067690 | 5/2009 |
| WO | WO-2009/067699 | 5/2009 |
| WO | WO 2009/094456 A2 | 7/2009 |

OTHER PUBLICATIONS

Brannagan, T.H. et al. "High-dose cyclophosphamide without stem-cell rescue for refractory CIDP" *Neurology*, Jun. 2002, 58:1856-1858.

Brannagan, T.H. et al. "High-dose cyclophosphamide without stem cell rescue for refractory multifocal motor neuropathy" *Muscle Nerve*, Aug. 2006, 34:246-250.

Brien, J.F. et al. "Aldehyde dehydrogenase inhibitors as alcohol-sensitizing drugs: a pharmacological perspective" *TIPS*, Dec. 1985, 477-480.

Brodsky, R.A. et al. "Complete remission in severe aplastic anemia after high-dose cyclophosphamide without bone marrow transplantation" *Blood*, Jan. 1996, 87(2):491-494.

Brodsky, R.A. et al. "Immunoablative High-Dose Cyclophosphamide without Stem-Cell Rescue for Refractory, Severe Autoimmune Disease" *Ann Intern Med.*, Dec. 1998, 129(12):1031-1035.

Brodsky, R.A. et al. "Bone marrow transplantation for autoimmune diseases" *Current Opinion in Oncology*, Mar. 1999, 11(2): 83-86.

Brodsky, R.A. et al. "Elimination of Alloantibodies by Immunoablative High-Dose Cyclophosphamide" *Transplantation*, Feb. 2001, 71(3):482-484.

Brodsky, R.A. et al. "Durable Treatment-Free Remission after High-Dose Cyclophosphamide Therapy for Previously Untreated Severe Aplastic Anemia" *Ann Intern Med.*, Oct. 2001, 135(7):477-483.

Brodsky, R.A. "High-dose cyclophosphamide for aplastic anemia" *Curr Opin Oncol*, 2002, 14:143-146.

Brodsky, R.A. et al. "High-dose cyclophosphamide as salvage therapy for severe aplastic anemia" *Experimental Hematology*, 2004, 32:435-440.

Brodsky, R.A. "Acquired Severe Aplastic Anemia in Children: Is There a Standard of Care?" *Pediatr Blood Cancer*, 2004, 43:711-712.

Brodsky, R.A. et al. "Riddle: What do aplastic anemia, acute promyelocytic leukemia, and chronic myeloid leukemia have in common?" *Leukemia*, 2004, 18:1740-1742.

Cohen, L. "Optimization of dose-time factors for a tumor and multiple associated normal tissues" *Int. J. Radiation Oncology Biol. Phys.*, Feb. 1987, 13(2):251-258.

D'Crus, D. "High-dose intravenous cyclophosphamide therapy in severe SLE" *Lupus*, 2002, 11:403-404.

Deangelis, T. et al. "Multiple sclerosis: new treatment trials and emerging therapeutic targets" *Curr Opin Neurol*, 2008, 21:261-271.

De Bittencourt, P.R.M. et al. "Multiple sclerosis: long-term remission after a high dose of cyclophosphamide" *Acta Neurol Scand*, 2005, 111:195-198.

Dockham, P.A. et al. "Relative Contribution of Human Erythrocyte Aldehyde Dehydrogenase to the Systemic Detoxification of the Oxazaphosphorines" *Drug Metabolism and Disposition*, 1997, 25(12):1436-1441.

Drachman, D.B. et al. "Treatment of Refractory Myasthenia: "Rebooting" with High-Dose Cyclophosphamide" *Ann Neurol*, Jan. 2003, 53(1):29-34.

Drachman, D.B. et al. "High-dose therapy for autoimmune neurologic diseases" *Curr Opin Oncol*, 2005, 17:83-88.

Emadi, A. et al. "Cyclophosphamide and cancer: golden anniversary" *Nat. Rev. Clin. Oncol.*, Nov. 2009, 6:638-647.

Gauthier, S.A. et al. "Cyclophosphamide Therapy for MS" *The International MS Journal*, 2005, 12:52-58.

Germolec, D.R. et al. "Induction of CYP1A1 and ALDH-3 in Lymphoid Tissues from Fisher 344 Rats Exposed to 2,3,7,8-Tetrachlorodibenzodioxin (TCDD)" *Toxicology and Applied Pharmacology*, 1996, 137:57-66.

Ginestier, C. et al. "ALDH1 is a marker of normal and malignant human mammary stem cells and a predictor of poor clinical outcome" *Cell Stem Cell*, Nov. 15, 2007, 1(5):555-567.

Gladstone, D.E. et al. "High-dose cyclophosphamide for severe systemic lupus erythematosus" *Lupus*, 2002, 11:405-410.

Gladstone, D.E. et al. "High dose cyclophosphamide for severe refractory myasthenia gravis" *J Neurol Neurosurg Psychiatry*, 2004, 75:789-791.

Gladstone, D.E. et al. "High-dose cyclophosphamide results in long-term disease remission with restoration of a normal quality of life in patients with severe refractory chronic inflammatory demyelinating polyneuropathy" *Journal of the Peripheral Nervous System*, 2005, 10:11-16.

Gladstone, D.E. et al. "High-Dose Cyclophosphamide for Moderate to Severe Refractory Multiple Sclerosis" *Arch Neurol*, Oct. 2006, 63:1388-1393.

Hacker, M.P. et al. "Effect of Disulfiram (Tetraethylthiuram Disulfide) and Diethyldithiocarbamate on the Bladder Toxicity and Antitumor Activity of Cyclophosphamide in Mice" *Cancer Research*, Nov. 1982, 42:4490-4494.

Hadidi, A.H.F.A. et al. "Phenotypically Deficient Urinary Elimination of Carboxyphosphamide after Cyclophosphamide Administration to Cancer Patients" *Cancer Research*, Sep. 15, 1988, 48:5167-5171.

Hansell, N.K. et al. "Erythrocyte Aldehyde Dehydrogenase Activity: Lack of Association with Alcohol Use and Dependence or Alcohol Reactions in Australian Twins" *Alcohol & Alcoholism*, 2005, 40(5):343-348.

Helander, A. et al. "Comparision of Blood Aldehyde Dehydrogenase Activities in Moist Snuff Users, Cigarette Smokers and Nontobacco Users" *Alcohol Clin Exp Res*, 1991, 15(1):1-6.

Helander, A. "Aldehyde Dehydrogenase in Blood: Distribution, Characteristics and Possible Use as Marker of Alcohol Misuse" *Alcohol & Alcoholism*, 1993, 28(2):135-145.

Henze, T. "Managing Sepcific Symptoms in People with Multiple Sclerosis" *The International MS Journal*, 2005, 12:60-68.

Hilton, J. "Role of Aldehyde Dehydrogenase in Cyclophosphamide-resistant L1210 Leukemia" *Cancer Res*, Nov. 1984, 44:5156-5160.

(56) References Cited

OTHER PUBLICATIONS

Huhn, R.D, et al. "High-dose cyclophosphamide with autologous lymphocyte-depleted peripheral blood stem cell (PBSC) support for treatment of refractory chronic autoimmune thrombocytopenia" *Blood*, Jan. 2003, 101(1):71-77.

Jeavons, C.M. et al. "Effects of Elevated Female Sex Steroids on Ethanol and Acetaldehyde Metabolism in Humans" *Alcohol Clin Exp Res*, 1984, 8(4):352-358.

Jones, R.J. et al. "Assessment of aldehyde dehydrogenase in viable cells" *Blood*, May 1995, 85(10):2742-2746.

Kastan, M.B. et al. "Direct Demonstration of Elevated Aldehyde Dehydrogenase in Human Hematopoietic Progenitor Cells" *Blood*, May 1990, 75(10):1947-1950.

Kohn, F.R. et al. "Aldehyde Dehydrogenase Activity as the Basis for the Relative Insensitivity of Murine Pluripotent Hematopoietic Stem Cells to Oxazaphosphorines" *Biochemical Pharmacology*, 1985, 34(19):3465-3471.

Kohn, F.R. et al. "Effect of Aldehyde Dehydrogenase Inhibitors on the *ex Vivo* Sensitivity of Human Multipotent and Committed Hematopoietic Progenitor Cells and Malignant Blood Cells to Oxazaphosphorines" *Cancer Research*, Jun. 15, 1987, 47:3180-3185.

Kohn, F.R. et al "Effect of Aldehyde Dehydrogenase Inhibitors on the *ex Vivo* Sensitivity of Murine Late Spleen Colony-Forming Cells (Day-12 CFU-S) and Hematopoietic Repopulating Cells to Mafosfamide (Asta Z 7557)" *Biochemical Pharmacology*, 1987, 36(17):2805-2811.

Krishnan, M.H.S. et al. "Reduction of Disease Activity and Disability With High-Dose Cyclophosphamide in Patients With Aggressive Multiple Sclerosis" *Arch Neurol*, Aug. 2008, 65(8):1044-1051.

Kumar, P. et al. "Chemoprotective action of Septilin against Cyclophosphamide Toxicity" *Indian Journal of Pharmaceutical Sciences*, 1995, 57(5):215-217.

Kwak, L.W. et al. "Vaccination with syngeneic, lymphoma-derived immunoglobulin idiotype combined with granulocyte/macrophage colony-stimulating factor primes mice for a protective T-cell response" *Proc. Natl. Acad. Sci. USA*, Oct. 1996, 93:10972-10977.

La Mantia, L. et al., "Cyclophosphamide for multiple sclerosis (Review)" *Cochrane Database of Systematic Reviews*, 2007, 1:1-23.

Lin, K.H. et al. "Regulation of Aldehyde Dehydrogenase Activity in Five Rat Hepatoma Cell Lines" *Cancer Res*, Nov. 1984, 44:5219-5226.

Lin, P.T. et al. "High-Dose Cyclophosphamide in Refractory Myasthenia Gravis With MuSK Antibodies" *Muscle Nerve*, Mar. 2006, 33:433-435.

Lindahl, R. "Aldehyde Dehydrogenases and Their Role in Carcinogensis" *Critical Reviews in Biochemistry and Molecular Biology*, 1992, 27(4,5):283-335.

Lioznov, M.V. et al. "Aldehyde dehydrogenase activity as a marker for the quality of hematopoietic stem cell transplants" *Bone Marrow Transplantation*, 2005, 35:909-914.

Luznik, L. et al. "Durable engraftment of major histocompatibility complex-incompatible cells after nonmyeloablative conditioning with fludarabine, low-dose total body irradiation, and post-transplantation cyclophosphamide" *Blood*, Dec. 2001, 98(12):3456-3464.

Luznik, L. et al. "Post-Transplantation High-Dose Cyclophosphamide (Cy) is Effective Single Agent GVHD Prophylaxis That Permits Prompt Immune Reconstruction after Myeloablative HLA Matched Related and Unrelated Bone Marrow Transplantation (BMT)" Session Type: Poster Sesion, Board #120-III; presented at American Society of Hematology (ASH) Annual Meeting Dec. 11, 2006; Abstract # 2891 appears in Blood, 108(11), (Nov. 16, 2006).

Luznik, L. et al. "Post-Transplantation High-Dose Cyclophosphamide (Cy) is Effective Single Agent GVHD Prophylaxis That Permits Prompt Immune Reconstruction after Myeloablative HLA Matched Related and Unrelated Bone Marrow Transplantation (BMT)" *Biology of Blood and Marrow Transplantation*, Feb. 2007, 13(2)(1):4, Abstracts from the 2007 BMT Tandem Meetings; Available online Jan. 25, 2007.

Magni, M. et al. "Induction of cyclophosphamide-resistance by aldehyde-dehydrogenase gene transfer" *Blood*, 1996, 87:1097-1103.

Maki, P.A. et al. "Potentiation of the Cytotoxic Action of Mafosfamide by *N*-Isopropyl-*p*-formylbenzamide, a Metabolite of Procarbazine" *Cancer Research*, Aug. 15, 1991, 51:4170-4175.

McGuire, T.R. et al. "High-dose cyclophosphamide in multiple sclerosis patients undergoing autologous stem cell transplantation" *International Immunopharmacology*, 2003, 3:279-283.

Moreb, J.S. et al. "Retinoic Acid Down-Regulates Aldehyde Dehydrogenase and Increases Cytotoxicity of 4-Hydroperoxycyclophosphamide and Acetaldehyde" *The Journal of Pharmacology and Experimental Therapeutics*, 2005, 312(1):339-345.

Moyo, V.M. et al. "High-dose cyclophosphamide for refractory autoimmune hemolytic anemia" Blood, Jul. 2002, 100(2):704-706.

Nousari, H.C. et al. "Immunoablative high-dose cyclophosphamide without stem cell rescue in paraneoplastic pemphigus: Report of a case and review of this new therapy for severe autoimmune disease" *J Am Acad Dermatol*, May 1999, 40(5)(1):750-754.

Nousari, C.H. etal. "Evaluating the role of immunoablative high-dose cyclophosphamide therapy in pemphigus vulgaris" *J Am Acad Dermatol*, Jul. 2003, 49(1):148-150.

Perini, P. et al. "Cyclophosphamide is effective in stabilizing rapidly deteriorating secondary progressive multiple sclerosis" *J Neurol*, 2003, 250:834-838.

Petri, M. et al. "High-Dose Cyclophosphamide Without Stem Cell Transplantation in Systemic Lupus Erythematosus" *Arthritis & Rheumatism*, Jan. 2003, 48(1):166-173.

Povsic, T.J. et al. "Circulating Progenitor Cells Can Be Reliably Identified on the Basis of Aldehyde Dehydrogenase Activity" *Journal of the American College of Cardiology*, Dec. 2007, 50(23):2243-2248.

Prestrud, A.A. et al. "High-dose cyclophosphamide therapy without stem cell rescue for severe refractory autoimmune illnesses: comment on the article by Moore et al" *Arthritis & Rheumatism*, May 2003, 48(5):1463.

Rekha, G.K. et al. "Multienzyme-mediated stable and transient multidrug resistance and collateral sensitivity induced by xenobiotics" *Cancer Chemother Pharmacol*, 1997, 40:215-224,.

Russo, J.E. et al. "Characterization of Cytosolic Aldehyde Dehydrogenase from Cyclophosphamide Resistant L1210 Cells" *Cancer Res*, Jun. 1988, 48:2963-2968.

Safety Data Sheet "Cyclosphosphamide" Division of Occupational Health and Safety National Institutes of Health, prepared by the Environmental Control and Research Program, Mar. 1987, 8 pages.

Sahovic, E.A. et al. "Role for Aldehyde Dehydrogenase in Survival of Progenitors for Murine Blast Cell Colonies after Treatment with 4-Hydroperoxycyclophosphamide *in Vitro*" *Cancer Research*, Mar. 1, 1988, 48:1223-1226.

Schwartzman, R.J. et al. "High-Dose Cyclophosphamide in the Treatment of Multiple Sclerosis" *CNS Neuroscience & Therapeutics*, 2009, 15:118-127.

Sehgal, A. et al. "Infectious Complications of High-Dose Cyclophosphamide Treatment in Autoimmune Disease" Blood (ASH Annual Meeting Abstracts), 2004, 104: Abstract 5091.

Shammo, J. et al. "Immune Ablation Using High-Dose Cyclophosphamide without Stem Cell Rescue for Intractable Multiple Sclerosis" Blood (ASH Annual Meeting Abstracts), 2005, 106: Abstract 5504.

Shih, W.W.H. et al. "Difference in effect of single immunosuppressive agents (cyclophosphamide, CCNU, 5-FU) on peripheral blood immune cell parameters and central nervous system immunoglobulin synthesis rate in patients with multiple sclerosis" *Clin. Exp. Immunol.*, 1983, 53:122-132.

Slådek, N.E. et al. "Aldehyde Dehydrogenase-Mediated Cellular Relative Insensitivity to the Oxazaphosphorines" *Curr. Pharm. Des.*, 1999, 5(8):607-625.

Slådek, N.E. et al. "Cellular levels of aldehyde dehydrogenases (ALDH1A1 and ALDH3A1) as predictors of therapeutic responses

(56) References Cited

OTHER PUBLICATIONS to cyclophosphamide-based chemotherapy of breast cancer: a retrospective study" *Cancer Chemother Pharmacol*, 2002, 49:309-321.
Slådek, N.E. et al. "Human Aldehyde Dehydrogenases: Potential Pathological, Pharmacological, and Toxicological Impact" *J. Biochem. Molecular Toxicology*, 2003, 17(1):7-23.
Smith, D.R. et al. "A randomized blinded trial of combination therapy with cyclophosphamide in patients with active multiple sclerosis on interferon beta" *Multiple Sclerosis*, 2005, 11:573-582.
Sreerama, L. et al. "Identification of a Methylcholanthrene-induced Aldehyde Dehydrogenase in a Human Breast Adenocarcinoma Cell Line Exhibiting Oxazaphosphorine-specific Acquired Resistance" *Cancer Res*, Apr. 1994, 54:2176-2185.
Sreerama, L. et al. "Identification of a Class 3 Aldehyde Dehydrogenase in Human Saliva and Increased Levels of this Enzyme, Glutathione S-Transferases, and DT-Diaphorase in the Saliva of Subjects Who Continually Ingest Large Quantities of Coffee or Broccoli" *Clin Cancer Res*, Oct. 1995, 1:1153-1163.
Sreerama, L. et al. "Cellular Levels of Class 1 and Class 3 Aldehyde Dehydrogenases and Certain Other Drug-metabolizing Enzymes in Human Breast Malignancies" *Clinical Cancer Research*, Nov. 1997, 3:1901-1914.
Takebe, N. et al. "Generation of Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene" *Molecular Therapy*, Jan. 2001, 3(1):88-96.
Venkataranganna, M.V. et al. "Pharmacodynamics & toxicological profile of PartySmart, a herbal preparation for alcohol hangover in Wistar rats" *Indian J Med Res*, May 2008, 127:460-466.
Weiner, H.L. et al. "Treatment of multiple sclerosis with cyclophosphamide: critical review of clinical and immunologic effects" *Mult Scler*, 2002, 8:142-154.
Zhang, J. et al. "Clinical Pharmacology of Cyclophosphamide and Ifosfamide" *Current Drug Therapy*, 2006, 1:55-84.
Notification of Transmittal of the International Search Report and the Written Opinion of the International Searching Authority dated Jun. 10, 2009 in International Application Serial No. PCT/US2008/084396, filed Nov. 21, 2008.
Notification of Transmittal of the International Search Report and the Written Opinion of the International Searching Authority dated Jun. 25, 2009 in International Application Serial No. PCT/US2008/084414, filed Nov. 21, 2008.
Groot et al. "Aldehyde Dehydrogenase Involvement in a Variant of the Brown Norway Rat Acute Myelocytic Leukaemia (BNML) that Acquired Cyclophosphamide Resistance *in Vivo*" European Journal of Cancer, 1994, 30A(14): 2137-2143.
Freeman, E. "High Time for HiCy?" *Hopkins Medicine*, Winter 2008, pp. 21-27.
Santos, G.W. Of al. "The Use of Cyclophosphamide for Clinical Marrow Transplantation" *Transplant Proc.*, Dec. 1972, 4(4):559-564.
Zoumbos, N.C. et al. "Circulating Activated Suppressor T Lymphocytes in Aplastic Anemia" *The New England Journal of Medicine*, Jan. 31, 1985, 312(5):257-265.
Leandro, M. et al. "An Open Study of B Lymphocyte Depletion in Systemic Lupus Erythematosus" *Arthritis & Rheumatism*, Oct. 2002, 46(10):2673-2677.
Brown Ra et al., "High-Dose Etoposide and Cyclophosphamide Without Bone Marrow Transplantation for Resistant Hematological Malignancy" *Blood*, 1990, 76(3):437-479.
Office Action dated May 20, 2013 in U.S. Appl. No. 12/789,401, filed May 27, 2010.
Office Action dated Oct. 11, 2012 in U.S. Appl. No. 12/789,401, filed May 27, 2010.
Office Action dated Jan. 2, 2014 in U.S. Appl. No. 12/785,211, filed May 21, 2010.
Office Action dated Mar. 7, 2013 in U.S. Appl. No. 12/785,211, filed May 21, 2010.
Office Action dated Apr. 2, 2009 in U.S. Appl. No. 11/566,296, filed Dec. 4, 2006.
Office Action dated May 14, 2008 in U.S. Appl. No. 11/566,296, filed Dec. 4, 2006.
Office Action dated Mar. 14, 2013 in U.S. Appl. No. 12/777,729, filed May 11, 2010.
Office Action dated Apr. 13, 2012 in U.S. Appl. No. 12/777,729, filed May 11, 2010.
Office Action dated Dec. 21, 2012 in U.S. Appl. No. 13/240,433, filed Sep. 22, 2011.
Office Action dated Oct. 4, 2013 in U.S. Appl. No. 13/240,433, filed Sep. 22, 2011.
Office Action dated Dec. 31, 2012 in U.S. Appl. No. 13/230,212, filed Sep. 12, 2011.
Office Action dated Feb. 27, 2014 in U.S. Appl. No. 13/232,326, filed Sep. 14, 2011.
Office Action dated Sep. 11, 2013 in U.S. Appl. No. 13/232,326, filed Sep. 14, 2011.
Office Action dated Oct. 19, 2012 in U.S. Appl. No. 13/232,326, filed Sep. 14, 2011.
Office Action dated Jun. 14, 2012 in U.S. Appl. No. 13/232,326, filed Sep. 14, 2011.
Office Action dated Apr. 1, 2014 in U.S. Appl. No. 13/240,465, filed Sep. 22, 2011.
Office Action dated Nov. 8, 2013 in U.S. Appl. No. 13/240,465, filed Sep. 22, 2011.
Office Action dated May 24, 2013 in U.S. Appl. No. 13/240,465, filed Sep. 22, 2011.
Adamkiewicz, T.V. et al. "Unrelated cord blood transplantation in children with sickle cell.disease: Review of four-center experience" *Pediatr Transplantation*, 2007, 11:641-644.
Alyea, E.P. et al. "Comparative outcome of nonmyeloablative and myeloablative allogeneic hematopoietic cell transplantation for patients older than 50 years of age" *Blood*, Feb. 15, 2005, 105(4):1810-1814.
Alyea, E.P. et al. "Impact of Conditioning Regimen Intensity on Outcome of Allogeneic Hematopoietic Cell Transplantation for Advanced Acute Myelogenous Leukemia and Myelodysplastic Syndrome" *Biology of Blood and Marrow Transplantation*, 2006, 12:1047-1055.
Attema-De Jonge, M.E. "Pharmacokinetically guided dosing of (high-dose) chemotherapeutic agents" Thesis University Utrecht, Dec. 17, 2004, pp. 1-313.
Bacigalupo, A. et al. "Defining the Intensity of Conditioning Regimens: working definitions" *Biol Blood Marrow Transplant*, Dec. 2009, 15(12):1628-1633.
Baron, F. et al. "Allogeneic Hematopoietic Cell Transplantation Following Nonmyeloablative Conditioning as Treatment for Hematologic Malignancies and Inherited Blood Disorders" *Molecular Therapy*, Jan. 2006, 13(1):26-41.
Bernaudin, F. et al. "Long-term results of related myeloablative stem-cell transplantation to cure sickle cell disease" *Blood*, Oct. 1, 2007, 110(7):2749-2756.
Billings Gazette Article, "Chemo drug might help advanced MS patients" Posted Apr. 28, 2004.
Billings Gazette Article, "Health: Chemo drug might help advanced MS patients" Posted Apr. 28, 2004.
Brodsky RA, "Biology and management of acquired severe aplastic anemia" 1998, *Current Opinion in Oncology*, 1998, 10(2):95-9. Abstract.
Brodsky, R.A. "Reduced intensity HLA-haploidentical BMT with post transplantation cyclophosphamide in nonmalignant hematologic diseases" *Bone Marrow Transplant*, Oct. 2008, 42(8):523-527.
Brodsky, R.A. et al. "Multicenter phase 3 study of the complement inhibitor eculizumab for the treatment of patients with paroxysmal nocturnal hemoglobinuria" *Blood*, Feb. 15, 2008, 111(4):1840-1847.
Brown, R.A. et al. "High-Dose Etoposide, Cyclophosphamide, and Total Body Irradiation With Allogeneic Bone Marrow Transplantation for Patients With Acute Myeloid Leukemia in Untreated First Relapse: A Study by the North American Marrow Transplant Group" *Blood*, Mar. 1, 1995, 85(5):1391-1395.
Burroughs, L. et al. "Comparison of Allogeneic Hematopoietic Cell Transplantation (HCT) after Nonmyeloablative Conditioning with HLA-Matched Related (MRD), Unrelated (URD), and Related Haploidentical (Haplo) Donors for Relapsed or Refractory Hodgkin Lymphoma (HL)" *Blood (ASH Annual Meeting Abstracts)*, 2007, 110: Abstract 173.
Burroughs, L.M. et al. "Comparison of Outcomes of HLA-Matched Related, Unrelated, or HLA-Haploidentical Related Hematopoietic Cell Transplantation following Nonmyeloablative Conditioning for

(56) References Cited

OTHER PUBLICATIONS

Relapsed or Refractory Hodgkin Lymphoma" *Biol Blood Marrow Transplant*, Nov. 2008, 14(11):1279-1287.

Chung D et al., "Anti-Thymocyte Globulin Prevents Autoimmune Encephalomyelitis by Expanding Myelin Antigen Specific Foxp3+ Regulatory T Cells" *Clinical Immunology*, 2007, 123:S10-S11. Abstract.

Davis et al., "Idiotype Vaccination Following ABMT Can Stimulate Specific Anti-Idiotype Immune Responses in Patients with B-Cell Lymphoma" *Biology of Blood and Marrow Transplantation*, 2001, 7:517-522.

Demirer, T. et al. "High-Dose Cyclophosphamide, Carmustine, and Etoposide Followed by Allogeneic Bone Marrow Transplantation in Patients With Lymphoid Malignancies Who Had Received Prior Dose-Limiting Radiation Therapy" *J Olin Oncol*, Mar. 1995, 13(3):596-602.

Dezern, A.E. et al. "Post-transplantation cyclophosphamide for GVHD prophylaxis in severe aplastic anemia" *Bone Marrow Transplantation*, 2010, pp. 1-2.

Djulbegovic, B. et al. "Nonmyeloablative Allogeneic Stem-Cell Transplantation for Hematologic Malignancies: A Systematic Review" *Cancer Control*, 2003, 10(1):17-41.

Droz, J.P. et al. "Failure of High-Dose Cyclophosphamide and Etoposide Combined with Double-Dose Cisplatin and Bone Marrow Support in Patients with High-Volume Metastatic Nonseminomatous Germ-Cell Tumours: Mature Results of a Randomised Trial" *European Urology*, 2007, 51:739-748.

Eto, M. et al. "Specific Destruction of Host-Reactive Mature T Cells of Donor Origin Prevents Graft-Versus-Host Disease in Cyclophosphamide-Induced Tolerant Mice" *The Journal of Immunology*, Mar. 1, 1991, 146(5):1402-1409.

European Search Report dated Oct. 7, 2011 from EP 08836174.6.

Fuchs Ej et al., "Post-transplantation cyclophosphamide (Cy) reduces graft rejection and graft-versus-host disease (GVHD) after non-myeloablative, partially HLA-mismatched (haploidentical) bone marrow transplantation (BMT)" *Blood*, 2004, 104:437a.

Hess, D.A. et al. "Selection based on CD133 and high aldehyde dehydrogenase activity isolates , long-term reconstituting human hematopoietic stem cells" *Blood*, Mar. 1, 2006, 107(5):2162-2169.

Hillmen, P. et al. "The Complement Inhibitor Eculizumab in Paroxysmal Nocturnal Hemoglobinuria" *N Engl J Med*, Sep. 21, 2006, 355(12):1233-1243.

Horan, J.T. et al. "Hematopoietic stem cell transplantation for multiply transfused patients with sickle cell disease and thalassemia after low-dose total body irradiation, fludarabine, and rabbit antithymocyte globulin" *Bone Marrow Transplantation*, 2005, 35:171-177.

Hsu, FJ et al., "Vaccinnation of patients with B-cell lymphoma using autologous antigen-pulsed dendritic cells" *Nature Medicine*, 1996, 2(1):52-58.

Huzly D, et al., "Routine Immunizations in Adult Renal Transplant Recipients." *Transplantation*, 1997, 63:839-845.

Iannone, R. et al. "Results of Minimally Toxic Nonmyeloablative Transplantation in Patients with Sickle Cell Anemia and β-Thalassemia" *Biology of Blood and Marrow Transplantation*, 2003, 9:519-528.

International Search Report dated Dec. 16, 2008, from PCT/US08/11402.

International Search Report dated Dec. 24, 2008 from PCT/US07/81614.

International Search Report dated Jan. 29, 2009 from PCT/US2007/078521.

International Search Report dated Jan. 8, 2009 from PCT/US2007/078524.

International Search Report dated Jun. 7, 2007 from PCT/US2006/061549.

International Search Report dated Nov. 6, 2008 from PCT/US2007/078518.

Jalla, S. et al. "Cyclophosphamide Plus Allogeneic CD4+T Cell Infusion Induces Anti-Lymphoma Immunity Despite Lack of Graft-Versus-Host Disease (GVHD) or Sustained Engraftment" *Blood (ASH Annual Meeting abstracts)*, 2004, 104: Abstract 3063.

Kasamon, Y.L. et al. "Greater HLA Disparity Is Associated with Reduced Risk of Relapse and Improved Event-Free Survival after Nonmyeloablative, HLA-Haploidentical BMT with Post-Transplantation High-Dose Cyclophosphamide" *Blood (ASH Annual Meeting abstracts)*, 2008, 112: Abstract 150.

Kasamon, Y.L. et al. "Immunologic recovery following autologous stem-cell transplantation with pre- and posttransplantation rituximab for low-grade or mantle cell lymphoma" *Annels of Oncology*, Jun. 2010, 21(6):1203-1210.

Kasamon, Y.L. et al. "Nonmyeloablative HLA-Haploidentical BMT with High-Dose Posttransplantation Cyclophosphamide: Effect of HLA Disparity on Outcome" *Biol Blood Marrow Transplant*, Apr. 2010, 16(4):482-489.

Kerr D et al., "Revimmune: Delivering a knockout punch to autoimmune diseases" *Specialty Pharma—Therapeutic Focus*, 2007, 7(6):80-83.

Krishnan C et al., "High-Dose Cyclophosphamide in the Treatment of Aggressive Multiple Sclerosis" *American Academy of Neurology*, Annual Meeting: 2006 Abstract (Apr. 4, 2006).

Krishnan C et al., "Reduction of Disease Activity and Disability with High Dose Cyclophosphamide in Patients with Aggressive Multiple Sclerosis" *Archives of Neurology*, 2008, 65(8):E1-E8.

Levy, M.Y. et al. "Clinical Tumor Responses Despite Graft Rejection after Nonmyeloablative Conditioning and Transplantation of Partially HLA-Mismatched (Haploidentical) Bone Marrow" *Blood (ASH Annual Meeting Abstracts)*, 2005, 106: Abstract 2897.

Luznik L et al., "Post Transplantation Cyclophosphamide Facilitates Engraftment of Major Histocompatibility Complex-Identical Allogenic Marrow in Mice conditioned with Low-Dose Total Body lrridiation" *Biology of Blood and Marrow Transplantation*, 2002, 8:131-138.

Luznik, L. et al. "Post-transplantation high dose cyclophosphamide (CY) is effective single agent for prevention of acute and chronic graft versus host disease after myeloablative HLA matched related and unrelated bone marrow transplantation (BMT)" *Blood (ASH Annual Meeting Abstracts)*, 2008, 112: Abstract 56.

Luznik, L. et al. "High-dose cyclophosphamide as single-agent, short-course prophylaxis of graft-versus-host disease" *Blood*, Apr. 22, 2010, 115(16):3224-3230.

Luznik, L. et al. "High-dose cyclophosphamide for graft-versus-host disease prevention" *Current Opinion in Hematology*, 2010, 17:493-499.

Luznik, L. et al. "High-dose, post-transplantation cyclophosphamide to promote graft-host tolerance after allogeneic hematopoietic stem cell transplantation" *Immunol Res*, 2010, 47:65-77.

Luznik, L. et al. "HLA-Haploidentical Bone Marrow Transplantation for Hematologic Malignancies Using Nonmyeloablative Conditioning and High-Dose, Posttransplantation Cyclophosphamide" *Biol Blood Marrow Transplant*, Jun. 2008, 14(6):641-650.

Luznik, L. et al. "Nonmyeloablative alternative donor transplants" *Current Opinion in Oncology*, 2003, 15:121-126.

Maksymovvych WP et al., "Evaluation and Validation of the Patient Acceptable Symptom State (PASS) in Patients With Ankylosing Spondylitis" *Arthritis & Rheumatism (Arthritis Care & Research)*, 2007, 57(1): 133-139.

Mayumi, H. et al. "Cyclophosphamide-Induced Immunological Tolerance: an Overview" *Immunobiol.*, 1996, 195:129-139.

Mayumi, H. et al. "Drug-Induced Tolerance to Allografts in Mice" *Transplantation*, 1987, 44(2):286-290.

Mentzer, W.C. et al. "Availability of Related Donors for Bone Marrow Transplantation in Sickle Cell Anemia" *Am. J. Pediatr. Hematol. Onco.*, 1994, 16(1):27-29.

Mickey MR et al., "Correlation of Clinical and Immunologic States in Multiple Sclerosis" *Archives of Neurology*, 1987;44(4):371-375. Abstract.

Mielcarek, M. et al. "Graft-versus-host disease after nonmyeloablative versus conventional hematopoietic stem cell transplantation" *Blood*, Jul. 15, 2003, 102(2):756-762.

(56) References Cited

OTHER PUBLICATIONS

Mink, S.A. et al. "High-Dose Therapy in Lymphomas: A Review of the Current Status of Allogeneic and Autologous Stem Cell Transplantation in Hodgkin's Disease and Non-Hodgkin's Lymphoma" *The Oncologist*, 2001, 6:247-256.
Moody DJ et al., "Administration of monthly-pulse cyclophosphamide in multiple sclerosis patients. Effects of long-term treatment on immunologic parameters." *Journal of Neuroimmunology*, 1987, 14(2):161-73. Abstract.
Moreb JS et al., "Heterogeneity of Aldehyde Dehydrogenase Expression in Lung Cancer Cell Lines Is Revealed by Aldefluor Flow Cytometry-Based Assay" *Cytometry Part B (Clinical Cytometry)*, 2007, 72B:281-289.
Noonan, K. et al. "Enrichment of Allogeneic Tumor Antigen-Specific T Cells From Bone Marrow (BM) of Patients Treated with High-Dose Post-Transplant Cyclophoshamide (Cy)—A Novel Approach to Adoptive Immunotherapy" *Blood (ASH Annual Meeting Abstracts)*, 2011, 118: Abstract 647.
O'Donnell, P. et al. "Favorable Outcome of Patients with Relapsed Hodgkin Lymphoma (HL) after Nonmyeloablative Hematopoietic Cell Transplantation (NM-HCT) Using Related Haploidentical Donors" *Blood (ASH Annual Meeting Abstracts)*, 2006, 108: Abstract 3135.
O'Donnell, P.V. et al. "Nonmyeloablative Bone Marrow Transplantation from Partially HLA-Mismatched Related Donors Using Posttransplantation Cyclophosphamide" *Biology of Blood and Marrow Transplantation*, 2002, 8:377-386.
Office Action dated Jan. 4, 2013 in U.S. Appl. No. 13/240,443, filed Sep. 22, 2011.
Office Action dated May 22, 2012 in U.S. Appl. No. 13/240,443, filed Sep. 22, 2011.
Openshaw, H. et al. "Peripheral Blood Stem Cell Transplantation in Multiple Sclerosis With Busulfan and Cyclophosphamide Conditioning: Report of Toxicity and Immunological Monitoring" *Biology of Blood and Marrow Transplantation*, 2000, 6:563-575.
Pallera et al., "Managing the Toxicity of Hematopoietic Stem Cell Transplant" *J. Support. Oncol.*, 2004, 2(3):223-247.
Panepinto, J.A. et al. "Matched-related donor transplantation for sickle cell disease: report from the Center for International Blood and Transplant Research" *British Journal of Haematology*, 2007, 137:479-485.
Perry, J.J. et al. "Administration and pharmacokinetics of high-dose cyclophosphamide with hemodialysis support for allogeneic bone marrow transplantation in acute leukemia and end-stage renal disease" *Bone Marrow Transplantation*, 1999, 23:839-842.
Peters, W.P. et al. "High-Dose Combination Alkylating Agents With Bone Marrow Support as Initial Treatment for Metastatic Breast Cancer" *J Clin Oncol*, Sep. 1998, 6(9):1368-1376.
Petrus, M.J. et al. "An Immunoablative Regimen of Fludarabine and Cyclophosphamide Prevents Fully MHC-Mismatched Murine Marrow Graft Rejection Independent of GVHD" *American Society for Blood and Marrow Transplantation*, 2000, pp. 182-189.
Rossi, H.A. et al. "High-dose cyclophosphamide, BCNU, and VP-16 (CBV) conditioning before allogeneic stem cell transplantation for patients with non-Hodgkin's lymphoma" *Bone Marrow Transplantation*, 2003, 31:441-446.
Rother, R.P. et al. "Discovery and development of the complement inhibitor eculizumab for the treatment of paroxysmal nocturnal hemoglobinuria" *Nature Biotechnology*, Nov. 2007, 25(11):1256-1264.
Ruggieri, M. et al. "Glatiramer Acetate in Multiple Sclerosis: A Review" *CNS Drug Reviews*, 2007, 13(2):178-191.
Savage WJ et al., "Treatment of Hepatitis-Associated Aplastic Anemia with High Dose Cyclophosphamide" ASH 2006, Session Type: Poster Session, Board #103-I; Abstract 179 (Dec. 9, 2006); Abstract #975 appears in Blood, 108(11), Nov. 16, 2006.
Snowden, J.A. "Haemopoetic Stem Cell Transplantation in Autoimmune Disease" Bangkok, Thailand, Oct. 24-28, 1999, pp. 180-183.
Spitzer, T.R. "Nonmyeloablative Allogeneic Stem Cell Transplant Strategies and the Role of Mixed Chimerism" *The Oncologist*, 2000, 5:215-223.
Storb, R. et al. "Marrow Transplantation From HLA-Identical Siblings for Treatment of Aplastic Anemia: Is Exposure to Marrow Donor Blood Products 24 Hours Before High-Dose Cyclophosphamide Needed for Successful Engraftment?" *Blood*, Apr. 1983, 61(4):672-675.
Supplementary European Search Report dated Apr. 27, 2011 from EP 11 00 1548.
Swinnen LJ et al., "Phase II Study of High Dose Outpatient Cyclophosphamide and Rituximab, without Stem Cell Support, for Low Grade and Mantle Cell Lyphoma" ASH 2006, Session Type: Poster Session, Board #919-II, Abstract 241 (Dec. 10, 2006); Abstract #2741 appears in Blood, 108(11), Nov. 16, 2006.
Symons, H. et al. "HLA-Haploidentical Bone Marrow Transplantation (BMT) for High Risk Hematologic Malignancies Using Myeloablative Conditioning and High-Dose, Posttransplantation Cyclophosphamide" *Blood (ASH Annual Meeting Abstracts)*, 2010, 116: Abstract 2362.
Symons, H.J. et al. "Impact of Killer Immunoglobulin Receptor (KIR) Ligand Incompatibility in Nonmyeloablative Bone Marrow Transplantation (BMT) from Haploidentical Donors" *Blood (ASH Annual Meeting Abstracts)*, 2010, 116: Abstract 604.
Symons, H.J. et al. "Improved survival with inhibitory Killer Immunoglobulin Receptor (KIR) gene mismatches and KIR haplotype B donors after nonmyeloablative, HLA-haploidentical bone marrow transplantation" *Biol Blood Marrow Transplant*, Apr. 2010, 16(4):533-542.
Symons, H.J. et al. "Low Incidence of CMV Reactivation and Infectious Morbidity and Mortality after Nonmyeloablative Haploidentical Bone Marrow Transplantation Incorporating Post-Transplantation Cyclophosphamide" *Blood (ASH Annual Meeting Abstracts)*, 2005, 106: Abstract 3245.
Symons, H.J. et al. "Low Incidence of CMV Reactivation and Infection after Allogeneic Bone Marrow Transplantation (BMT) Incorporating Post-Transplantation Cyclophosphamide (Cy)" *Blood (ASH Annual Meeting Abstracts)*, 2006, 108: Abstract 2859.
Takahashi, Y. et al. "In vitro and in vivo evidence of PNH cell sensitivity to immune attack after nonmyeloablative allogeneic hematopoietic cell transplantation" *Blood*, Feb. 15, 2004, 103(4):1383-1390.
Today's Sunbeam Article, "For Pennsville woman with MS, new treatment has been 'just a miracle'" posted Apr. 25, 2004.
Toze, C.L. et al. "Myeloablative allografting for chronic lymphocytic leukemia: evidence for a potent graft-versus-leukemia effect associated with graft-versus-host disease" *Bone Marrow Transplantation*, 2005, 36:825-830.
Uitdehaag BMJ et al., "Long-Lasting Effects of Cyclophosphamide on Lymphocytes in Peripheral Blood and Spinal Fluid" *Acta Neurologica Scandinavica*, 1989, 79(1):12-17. Abstract.
USA Today Article, "Researchers say large doses of chemo drug may fight MS" Posted Mar. 23, 2004.
Van Besien, K. et al. "Fludarabine-based conditioning for allogeneic transplantation in adults with sickle cell disease" *Bone Marrow Transplantation*, 2000, 26:445-449.
Vose, J.M. "Single Dose Pegfilgrastin (SD/01) Is as Effective as Daily Filgrastim Following ESHAP Chemotherapy for Subjects with Non-Hodgkin's Lymphoma or Hodgkin's Disease: Results of a Randomized, Open-Label Study" OncoLink Scientific Meetings Coverage, held Tuesday, Dec. 11, 2001, retrieved from http://www.oncolink.org/conferences/article.cfm?id=490.
Walters, M.C. "Cord blood transplantation for sickle cell anemia: Bust or boom?" *Pediatr Transplantation*, 2007, 11:582-583.
Zhou, X. et al. "Synergy between Nonmyeloablative Doses of Intravenous Busulfan and Post- Transplantation Cyclophosphamide for Induction of Tolerance to MHC-Compatible Stem Cell Allografts" *Blood, (ASH Annual Meeting Abstracts)*, 2005, 106: Abstract 3040.

* cited by examiner

| basegel | fugel | age | dzdurat | minwbc | geoaldh | meanaldh | CD4stim mean | CD4stimg eo | CD8mean | CD8geo | avg nadir wbc | new avg nadir wbc over 6 days | avg 5days |
|---|---|---|---|---|---|---|---|---|---|---|---|---|---|
| 4.50 | 0.00 | 47.00 | 15.00 | 70.00 | 135.00 | 177.00 | 14.31 | 11.70 | 6.07 | 5.76 | 106.00 | 88.00 | 86.00 |
| 5.50 | 0.00 | 46.00 | 9.00 | 0.00 | 130.00 | 171.00 | 13.26 | 10.72 | 5.04 | 4.62 | 45.40 | 35.00 | 39.00 |
| 8.00 | 0.00 | 27.00 | 2.00 | 6.00 | 115.00 | 159.00 | 15.94 | 11.08 | 5.36 | 4.96 | 39.60 | 33.00 | 30.00 |
| 8.00 | 0.00 | 46.00 | 15.00 | 12.00 | 105.00 | 134.00 | 10.86 | 8.26 | 6.17 | 5.74 | 36.20 | 45.00 | 36.00 |
| 9.00 | 1.00 | 44.00 | 15.00 | 24.00 | 172.00 | 217.00 | 11.95 | 9.89 | 5.05 | 4.65 | 122.80 | 119.00 | 75.00 |
| 8.50 | 2.00 | 28.00 | 3.00 | 0.00 | 77.00 | 93.00 | 6.77 | 5.63 | 8.54 | 7.80 | 32.40 | 29.00 | 25.00 |
| 7.00 | 7.00 | 20.00 | 4.00 | 31.00 | 148.00 | 201.00 | 11.96 | 9.28 | 5.81 | 5.39 | 69.20 | 76.00 | 69.00 |
| 6.00 | 0.00 | 28.00 | 1.50 | 12.00 | 95.00 | 115.00 | 6.59 | 5.44 | 8.21 | 7.68 | 63.60 | 65.00 | 64.00 |
| 2.50 | 1.00 | 29.00 | 4.00 | 50.00 | 161.00 | 200.00 | 23.94 | 19.74 | 7.73 | 7.17 | 72.00 | 83.00 | 72.00 |

Figure 1

| Spearman's rho | | | geoaldh | meanaldh | 6 day average | 5 day average |
|---|---|---|---|---|---|---|
| | geoaldh | Correlation Coefficient | 1.000 | .983() | .800() | .783(*) |
| | | Sig. (2-tailed) | - | 0.000 | 0.010 | 0.013 |
| | | N | 9 | 9 | 9 | 9 |
| | meanaldh | Correlation Coefficient | .983(**) | 1.000 | .783(*) | .767(*) |
| | | Sig. (2-tailed) | 0.000 | - | 0.013 | 0.016 |
| | | N | 9 | 9 | 9 | 9 |
| | 6 day average | Correlation Coefficient | .800(**) | .783(*) | 1.000 | .967(**) |
| | | Sig. (2-tailed) | 0.010 | 0.013 | - | 0.000 |
| | | N | 9 | 9 | 9 | 9 |
| | 5 day average | Correlation Coefficient | .783(*) | .767(*) | .967(**) | 1.000 |
| | | Sig. (2-tailed) | 0.013 | 0.016 | 0.000 | - |
| | | N | 9 | 9 | 9 | 9 |

Figure 2

METHODS FOR PROVIDING A SYSTEM OF CARE FOR A HIGH-DOSE OXAZAPHOSPHORINE DRUG REGIMEN

CROSS REFERENCE TO RELATED APPLICATIONS

This application is a continuation-in-part of U.S. application Ser. No. 12/785,224, filed May 21, 2010, now abandoned which is a continuation-in-part of International Application No. PCT/US2008/084396, filed Nov. 21, 2008, and International Application No. PCT/US2008/084414, filed Nov. 21, 2008, both of which international applications claim the benefit of U.S. Provisional Application No. 60/989,628, filed Nov. 21, 2007, U.S. Provisional Application No. 61/038,033, filed Mar. 19, 2008, U.S. Provisional Application No. 61/088,600, filed Aug. 13, 2008, U.S. Provisional Application No. 61/095,884, filed Sep. 10, 2008, U.S. Provisional Application No. 61/096,232, filed Sep. 11, 2008, and U.S. Provisional Application No. 61/106,073, filed Oct. 16, 2008, all of which are herein incorporated by reference in their entireties.

BACKGROUND

Aldehyde dehydrogenases (ALDHs) are intracellular enzymes responsible for oxidizing aldehydes. Substrates for ALDHs include acetyldehyde, an intermediate in ethanol metabolism, and biogenic amines produced during catecholamine catabolism. (Russo et al., *Cancer Res.* 48: 2963-2968 (1988)). ALDH has also been reported to play a crucial role in the conversion of vitamin A to its active metabolite, retinoic acid (Labrecque et al., *Biochem. Cell Biol.* 71:85-89 (1993); Yoshida et al., *Enzyme* 46:239-244 (1992)).

High enzymatic activity of ALDH has been shown to be a characteristic feature of primitive hematopoietic progenitor cells in mice and humans (Kohn et al., *Biochem. Pharmacol.* 34:3465-3471 (1985); Kastan et al., *Blood* 75:1947-1950 (1990)). ALDH activity has been used as a marker to identify and enrich hematopoietic stem cells (Jones et al., *Blood*, 85(10): 2742-2746 (1995)), and to assess the quality of cells as hematopoietic stem cell transplants (Lioznov et al., *Bone Marrow Transplant.*, 35:909-914 (2005)). An assay based on ALDH activity useful in enumerating endogenous progenitor cells in peripheral blood has been described (Povsic et al., *J. Am. Coll. Cardiol.*, 50:2243-2248 (2007)).

Oxazaphosphorines (e.g., cyclophosphamide) are latent drugs that provide a chemically and pharmacologically inactive form of nitrogen mustards, cytotoxic chemotherapeutic agents. Oxazaphosphorines are metabolized to their active forms in vivo. For example, cyclophosphamide is a prodrug that requires metabolic activation to exhibit cytotoxic activity. The primary metabolite of cyclophosphamide, 4-hydroxycyclophosphamide (4-OH-CPA), is in equilibrium with its open-ring tautomer, aldophosphamide, which undergoes chemical decomposition to form phosphoramide mustard (a bifunctional DNA alkylator) and acrolein, with phosphoramide mustard being the ultimate cytotoxic metabolite. Alternatively, 4-OH-CPA and aldophosphamide are detoxified by glutathione S-transferase with thiols or sulfates and by ALDH to carboxycyclophosphamide, respectively. (Brock, *Cancer*, 78(3): 542-47 (1996)).

The dosage of oxazaphosphorines such as cyclophosphamide, and their toxicity profiles, vary widely depending on the clinical indication. Fifty years after it was first synthesized, cyclophosphamide continues to be used for a wide array of diseases, including solid tumors, hematologic malignancies, autoimmune disorders, stem cell mobilization, and as a conditioning regimen for bone marrow transplant (Emadi et al., *Nat. Rev. Clin. Oncol.*, 6:638-647 (2009)).

The chemotherapeutic properties of oxazaphosphorines have been demonstrated in a wide range of tumors. (Brock, *Cancer*, 78(3): 542-47 (1996)). For example, cyclophosphamide is one of the few drugs with a broad indication for cancer, and has been included in various chemotherapeutic regimens, as a monotherapy or in combination with other anti-neoplastic drugs (for example, 40-50 mg/kg over a period of 2-5 days, 10 to 15 mg/kg every 7-10 days, or 3-5 mg/kg twice weekly). Moreover, high-dose cyclophosphamide (for example, 50 mg/kg/day×4 days) has been used for the treatment of certain autoimmune diseases such as, for example, severe aplastic anemia. High-dose cyclophosphamide was originally used in allogeneic bone marrow transplantation because of its ability to break immune tolerance and facilitate engraftment. (Santos et al., *Transplant Proc.*, 4: 559-564 (1972)).

It has been observed that high levels of cytosolic ALDH produce cyclophosphamide-resistance in tumor cell lines (Russo J E and Hilton, J, *Cancer Res.*, 48:2963 (1988)). It has been shown that measurable levels of some ALDH enzymes are found in some, but not all, tumor types. Furthermore, in those tumor types where measurable ALDH levels are present (e.g., carcinomas of the breast), inter-individual variation may exist (ALDH levels may vary from patient to patient). Further, it has been proposed that ALDH-1 and ALDH-3 levels/activities in tumors can be used to predict the therapeutic potential of oxazaphosphorine chemotherapy regimens, e.g., in breast cancer (Sreerama L and Sladek N E, *Cancer Res.*, 54:2176-2185 (1994); Sladek N E, *Curr. Pharm. Des.*, 5(8):607-625 (1999); Sladek N E et al., *Cancer Chemother. Pharmacol.*, 49(4):309-321 (2002)). Other proposed clinical strategies based on ALDH include: sensitizing tumor cells to oxazaphosphorines by inhibiting synthesis of ALDH or ALDH activity; and decreasing the sensitivity of vulnerable and essential normal cells, such as pluripotent hematopoietic cells, to oxazaphosphorines by increasing ALDH1 or ALDH3 through gene delivery (Sladek N E et al., 2002).

SUMMARY

Despite the general knowledge regarding ALDH and oxazaphosphorine drugs, it remains difficult to select suitable patients for safe and effective oxazaphosphorine therapy, to select safe and effective dosages for oxazaphosphorine therapy and to predict whether a certain patient will experience treatment failure or disease relapse following oxazaphosphorine therapy. The present invention is based, at least in part, on the discovery of certain factors, e.g., safety and efficacy factors, which allow for the selection of an appropriate patient, for the selection of an appropriate pharmacological agent for a patient, for the selection of an appropriate dosage, and/or for the substantially accurate prediction of treatment results.

The chemotherapeutic properties of oxazaphosphorines have been demonstrated in a wide range of tumors and cyclophosphamide has been included in various chemotherapeutic regimens. Chemotherapy-induced neutropenia (low neutrophil count) is a major dose-limiting factor in the management of cancer patients. Clinicians currently assume that cyclophosphamide-induced neutropenia is caused by increased levels of the active cyclophosphamide metabolite, 4-hydroxycylophosphamide/aldophosphamide, due to increased cytochrome P450 (CP450) activity in the liver, whether by gene polymorphism or drug metabolism by CP450. Accordingly, the conventional wisdom in clinical practice, as reflected by the product label of cyclophosphamide (Cytoxan), is to adjust the dose of cyclophosphamide downward if the dose begins to cause neutropenia in the patient. However, neutropenia may actually be due to one or a combination of multiple factors including: reduced ALDH in the patient's granulocytes, and/or increased CP450 activity in the liver, which causes more 4-OH cyclophosphamide/aldophosphamide to be produced and exert its cytotoxic effect on both cancer cells and normal cells. There has been no prior appreciation of these opposing explanations for cyclophosphamide-induced neutropenia, and the conventional teaching in the clinical setting to reduce or withhold the dose of cyclophosphamide if neutropenia is occurring risks under-treating the patient's cancer because the cause of the neutropenia could be reduced ALDH levels in the neutrophils, increasing toxicity to them. Accordingly, the dosing information provided to, and relied upon, by the clinicians is wrong and the methods of the invention should be adopted.

In some aspects, the present invention is directed to methods for treating a subject in need thereof with an oxazaphosphorine. In some embodiments, the methods include determining whether treatment with an oxazaphosphorine can be safe and effective for the subject based on one or more safety or efficacy factors; and treating the subject with the oxazaphosphorine if it is determined that treatment with an oxazaphosphorine can be safe and effective. Thus, one aspect of the invention includes a method for treating a subject in need thereof with an oxazaphosphorine, comprising administering the oxazaphosphorine to a subject for which it has been pre-determined that treatment of that subject with the oxazaphosphorine can be safe and effective based on one or more safety or efficacy factors, such as an ALDH inhibition factor and/or ALDH activation factor.

In some aspects, the present invention is directed to methods for selecting a subject suitable for oxazaphosphorine therapy. In some embodiments, the methods include determining whether treatment with an oxazaphosphorine can be safe and effective for the subject based on one or more safety or efficacy factors, and selecting a subject suitable for oxazaphosphorine therapy where it is determined that treatment can be safe and effective.

In some aspects, the present invention is directed to systems for ensuring the safety or efficacy of a treatment that includes oxazaphosphorine administration. In some embodiments, the systems include selecting a set of safety and efficacy factors associated with the safe and effective treatment of a subject with an oxazaphosphorine drug; defining a set of information to be obtained from a subject including information probative of the set of selected safety and efficacy factors associated with the safe and effective treatment of a subject with an oxazaphosphorine drug; determining whether treatment that includes an oxazaphosphorine administration can be safe and effective for the subject based on the set of information; and generating a prescription approval code if it is determined that the treatment including the oxazaphosphorine administration can be safe and effective. In some embodiments, the method further comprises transmitting the prescription approval code to the drug manufacturer or administration facility that is to administer the oxazaphosphorine to the subject for which it has been determined that the treatment can be safe and effective. In some embodiments, to ensure that the correct subject is matched with the correct oxazaphosphorine (and, preferably, the correct dose of oxazaphoshorine), the container containing at least one dose of the oxazaphosphorine is tagged with (affixed or otherwise associated with) the authorized subject's unique identifying information (ID code, e.g., a bar code). In some embodiments, the prescription approval code is affixed to, or otherwise associated with, a container containing the oxazaphosphorine, and wherein the prescription approval code associates the container with the subject for which it has been determined that the treatment can be safe and effective. In some embodiments, the prescription approval code comprises a bar code or other identifier that is specific to the subject. In some embodiments, the system further comprises transmitting the container with the prescription approval code to the administration facility that is to administer the oxazaphosphorine to the subject for which it has been determined that the treatment can be safe and effective.

In some embodiments of the system for ensuring the safety or efficacy of a treatment that includes oxazaphosphorine administration, the information probative of the set of selected safety and efficacy factors comprises a radiological assessment (such as magnetic resonance imaging (MRI), or computed axial tomography scan (CT or CAT scan)) of the subject, a functional or quality of life assessment of the subject (such as expanded disability status scale (EDSS) or multiple sclerosis functional composite score (MSFC)), or both. In some embodiments, the subject undergoes a brain MRI assessment, or radiological evaluation for brain volume (e.g., T2-weighted axial images can be used to calculate the parenchymal fraction in order to assess brain volume), or the patient undergoes an MRI assessment for the presence of GEL). In some embodiments, the radiological assessment includes obtaining a brain or a spine radiological image or series of images (e.g., MRI, X-ray images, or CT), or data representative of the image (image data) from the subject. In some embodiments, the patient undergoes a pre-treatment functional assessment or quality of life assessment such as the EDSS, MSFC z-score, Scripps Neurologic Rating Scale (SNRS), Krupp Fatigue Severity Scale (FSS), Incapacity Status Scale (ISS), Functional Independence Measure (FIM), Ambulation Index (AI), Cambridge Multiple Sclerosis Basic Score (CAMBS), Functional Assessment of Multiple Sclerosis (FAMS), Profile of Mood States (POMS), Sickness Impact Profile (SIP), Guy's Neurological Disability Scale (GNDS), or a combination of two or more of the foregoing, and the results of this assessment are used to determine a patient's eligibility to receive treatment.

An aspect of the invention includes a method for treating a subject in need thereof with a cytotoxic agent, the method comprising: (a) determining the presence or absence of an ALDH inhibition factor in the subject, or determining whether the subject has otherwise been exposed to an ALDH inhibition factor; and (b) administering: (i) an oxazaphosphorine to the subject, if an ALDH inhibition factor is not present in the subject or if the subject has not otherwise been exposed to an ALDH inhibition factor, or (ii) a non-oxazaphosphorine cytotoxic agent to the subject, if an ALDH inhibition factor is present in the subject or if the subject has otherwise been exposed to an ALDH inhibition factor. For example, the method may comprise administering an oxazaphosphorine to a subject for which it has been pre-determined (e.g., by a clinician or others) that the subject has not been exposed to, or is not otherwise under the influence of, an ALDH inhibition factor. In other embodiments, the method may comprise withholding the oxazaphosphorine or administering a non-oxazaphosphorine cytotoxic agent to the subject for which it has been pre-determined (e.g., by a clinician or others) that the subject has been exposed to, or is otherwise under the influence of, an ALDH inhibition factor. In some embodiments, the method further comprises, prior to (b), after (b), or both prior to and after (b), obtaining an ALDH level in a sample of granulocytes obtained from the subject. In some embodiments, the non-oxazaphosphorine cytotoxic agent is an alkylating agent. In some embodiments, the non-oxazaphosphorine cytotoxic agent is an antimetabolite. In some embodiments, the antimetabolite is azathioprine. In some embodiments, the cytotoxic agent is administered to the subject for treatment of cancer. In some embodiments, the cytotoxic agent is administered to the subject for treatment of an immune disorder selected from among an autoimmune disease, an allergic reaction, and transplant rejection. In some embodiments, the cytotoxic agent is administered to the subject for treatment of multiple sclerosis.

An aspect of the invention includes a method for managing oxazaphosphorine-induced granulocytopenia, comprising: (a) determining the presence or absence of an ALDH inhibition factor in a subject, or determining whether the subject has otherwise been exposed to an ALDH inhibition factor; and (b) if an ALDH inhibition factor is present in the subject or if the subject has otherwise been exposed to an ALDH inhibition factor, (i) administering a reduced dose of oxazaphosphorine to the subject, or (ii) advising the subject to cease or avoid intake or exposure to the ALDH inhibition factor, or (iii) administering a non-oxazaphosphorine cytotoxic agent to the subject. Preferably, the severity of oxazaphosphorine-induced granulocytopenia, or the delay in granulocyte recovery following oxazaphosphorine-induced granulocytopenia, is thereby reduced in the subject. In some embodiments, the reduced dose is 50% or less of a standard therapeutic dose. In some embodiments, the reduced dose is 33% or less of a standard therapeutic dose. In some embodiments, the method further comprises determining granulocyte count in the subject one or more times after (b)(i) or (b)(ii).

In some embodiments, the one or more safety or efficacy factors includes an ALDH inhibition factor, e.g., hormonal contraceptive use, tobacco use, chronic alcohol (ethanol) consumption and any combinations thereof. In some embodiments, the one or more safety and efficacy factors includes use of at least one ALDH inhibiting agent or at least one ALDH activating agent. ALDH inhibiting agents include, but are not limited to disulfiram, calcium carbimide, diazepam, chlordiazepoxide, isosorbide dinitrate, nitroglycerine, chlorpropamide, tolazamide, and cephalosporin.

In some embodiments, the one or more ALDH inhibition factors are one or more anti-cancer agents. In some embodiments, the one or more ALDH inhibition factors are one or more antibiotics. In some embodiments, the one or more ALDH inhibition factors are one or more dietary constituents such as dietary supplements. In some embodiments, the one or more ALDH inhibition factors are one or more competitive inhibitors of ALDH, non-competitive inhibitors of ALDH, or mixed-type inhibitors of ALDH. In some embodiments, the one or more ALDH inhibition factors are one or more irreversible inhibitors of ALDH. In some embodiments, the one or more ALDH inhibition factors are one or more reversible inhibitors of ALDH.

An aspect of the invention includes a method for treating a subject in need thereof with a cytotoxic agent, the method comprising: (a) determining the presence or absence of an ALDH activation factor in the subject, or determining whether the subject has otherwise been exposed to an ALDH activation factor; and (b) if an ALDH activation factor is present in the subject or the subject has otherwise been exposed to an ALDH activation factor, (i) administering an increased dose of an oxazaphosphorine to the subject, or (ii) administering a non-oxazaphosphorine cytotoxic agent to the subject. In some embodiments, the increased dose is at least 50% greater than a standard therapeutic dose. In some embodiments, the increased dose is at least 33% greater than a standard therapeutic dose.

In some embodiments, the one or more ALDH activation factors are one or more ALDH activating (inducing) agents selected from the group consisting of coffee, oltipraz, *Crucifera* vegetable family member, Liliaceae vegetable family member, and Phenobarbital, or an ALDH activating metabolite of any of the foregoing.

In some embodiments, the one or more safety or efficacy factors includes an ALDH level consistent with a resistant ALDH level in hematopoietic progenitor stem cells. In some embodiments, the one or more safety or efficacy factors includes an ALDH level consistent with a resistant ALDH level in peripheral lymphocytes. In some embodiments, the one or more safety or efficacy factors includes a normal ALDH level or activity in granulocytes. For example, enhanced vulnerability of granulocytes to oxazaphosphorines due to ALDH inhibiting agents could lead to greater risk and/or degree of unwanted and dangerous granulocytopenia. In the context of cancer, while ALDH inhibition may increase sensitivity of the cancer cells to the oxazaphosphorine, it increases risk of infection. Accordingly, in some aspects, the invention is directed to methods for treating a subject in need thereof with a cytotoxic agent, the method comprising: (a) obtaining an ALDH level in a sample of granulocytes obtained from the subject; and (b) administering: (i) an oxazaphosphorine to the subject if the obtained ALDH level is consistent with a resistant ALDH level in granulocytes, or (ii) a reduced dose of the oxazaphosphorine to the subject if the obtained ALDH level is consistent with a sensitive ALDH level in granulocytes, or (iii) a non-oxazaphosphorine cytotoxic agent to the subject if the obtained ALDH level is consistent with a sensitive ALDH level in granulocytes. In some embodiments, the cytotoxic agent is being administered to the subject for treatment of cancer. In some embodiments, the non-oxazaphosphorine cytotoxic agent is an alkylating agent, or an antimetabolite such as azathioprine (Imuran). In some embodiments, the method further comprises, prior to (b), determining the presence or absence of an ALDH inhibiting agent in the subject, or determining whether the subject has otherwise been exposed to an ALDH inhibiting agent.

In some aspects, the present invention is directed to a method for treating a subject in need thereof with a cytotoxic agent, the method comprising: (a) determining the presence or absence of an ALDH inhibiting agent in the subject, or determining whether the subject has otherwise been exposed to an ALDH inhibiting agent; and (b) administering: (i) an oxazaphosphorine to the subject if an ALDH inhibiting agent is not present in the subject or if the subject has not otherwise been exposed to an ALDH inhibiting agent, or (ii) a reduced dose of the oxazaphosphorine to the subject if an ALDH inhibiting agent is present in the subject or if the subject has otherwise been exposed to an ALDH inhibiting agent, or (iii) a non-oxazaphosphorine cytotoxic agent to the subject if an ALDH inhibiting agent is present in the subject or if the subject has otherwise been exposed to an ALDH inhibiting agent. In some embodiments, the cytotoxic agent is being administered for treatment of cancer. In some embodiments, the reduced dose of (b)(ii) is less than that which would normally be administered for treatment of cancer. In some embodiments, the non-oxazaphosphorine cytotoxic agent is an alkylating agent, or an antimetabolite such as azathioprine (Imuran). In some embodiments, the method further comprises obtaining an ALDH level in a sample of granulocytes obtained from the subject prior to (b).

In some embodiments, the systems and methods of the present invention further include periodically determining whether treatment with an oxazaphosphorine continues to be safe and effective for the subject based on one or more safety or efficacy factors. In some embodiments, the systems and methods of the present invention further include monitoring white blood cell count before treatment, during treatment, after treatment, or a combination of two or more of the foregoing.

In some embodiments, treating the subject includes adjusting dosage or recommencing treatment based on the white blood cell count. In some embodiments, treating includes adjusting dosage or recommencing treatment based on the white blood cell count, based on an ALDH level in a sample comprising hematopoietic progenitor stem cells or based on an ALDH level in a sample comprising peripheral lymphocytes, or both.

In some embodiments, the oxazaphosphorine is selected from the group consisting of cyclophosphamide, ifosfamide, perfosfamide, trophosphamide, and a pharmaceutically acceptable salt, solvate, prodrug, or active metabolite thereof. In some embodiments, the oxazaphosphorine is cyclophosphamide. In other embodiments, the oxazaphosphorine is 4-hydroxycyclophosphamide or aldophosphsamide.

In some embodiments, the subject is a female of childbearing potential.

In some embodiments, treating the subject includes administering a myeloablative amount of oxazaphosphorine. In other embodiments, treating the subject includes administering a non-myeloablative amount of oxazaphosphorine. In some embodiments, treating the subject includes intravenous administration of about 40 mg/kg to about 50 mg/kg oxazaphosphorine in divided doses over a period of from about 2 to about 5 days. In other embodiments, treating the subject includes intravenous administration of about 10 mg/kg to about 15 mg/kg oxazaphosphorine every 7 to 10 days or about 3 to about 5 mg/kg twice weekly. In still other embodiments, treating the subject includes oral administration of about 2.5 mg/kg to about 3 mg/kg daily for about 60 to about 90 days. In other embodiments, treating the subject includes intravenous administration of 50 mg/kg/day of oxazaphosphorine. In yet other embodiments, treating the subject includes daily intravenous administration of 50 mg/kg/day of oxazaphosphorine, for 4 consecutive days. In some embodiments, treating the subject includes daily intravenous administration of about 100 mg/kg to about 200 mg/kg for 1 to 7 days. In other embodiments, treating the subject includes daily intravenous administration of about 25 mg/kg to about 100 mg/kg for 2 to 6 days. In further embodiments, treating the subject includes daily intravenous administration of about 25 mg/kg to about 100 mg/kg for 3 to 5 days.

In some embodiments, the subject is suffering from cancer. In other embodiments, the subject is suffering from an immune disorder. In still other embodiments, the subject is suffering from, or at risk of, an autoimmune disease, an allergic reaction, or transplant rejection.

In some aspects, the present invention is directed to methods for treating a subject in need thereof with an oxazaphosphorine. In some embodiments, the methods include treating the subject with an oxazaphosphorine; and providing the subject with information or advising the subject that the subject should not use at least one of hormonal contraceptives, tobacco or alcohol during oxazaphosphorine treatment.

In some embodiments, the methods further include advising the subject to discontinue use of hormonal contraception at least 120 days prior to oxazaphosphorine treatment. In some embodiments, the methods further include advising the subject to use non-hormonal contraception during oxazaphosphorine treatment. In some embodiments, the methods further include advising the subject to use non-hormonal contraception for at least 30 days subsequent to oxazaphosphorine treatment.

In some aspects, the present invention is directed to methods for delivering an oxazaphosphorine to subjects in need thereof while restricting access to the oxazaphosphorine by subjects for whom the drug may be contraindicated. In some embodiments, the methods include obtaining subject information relating to the existence of one or more contraindication factors; and permitting delivery of the oxazaphosphorine only after it has been determined that the subject can safely be treated based on the information relating to one or more contraindication factors. In some embodiments, to ensure that the correct subject is matched with the correct oxazaphosphorine (and, preferably, the correct dose of oxazaphoshorine), the container containing at least one dose of the oxazaphosphorine is tagged with (affixed or otherwise associated with) the authorized subject's unique identifying information (ID code, e.g., a bar code). In some embodiments, the oxazaphosphorine is delivered to the administration facility in a container, and the method further comprises affixing or otherwise associating an approval code with the container, wherein the approval code is specific to the subject for whom safe treatment has been determined. In some embodiments, the approval code comprises a bar code or other subject-specific identifier. In some embodiments, at least one dose of the oxazaphosphorine is tagged with (affixed or otherwise associated with) the authorized subject's unique identifying information (e.g., a bar code).

In some embodiments of the oxazaphosphorine delivery method, the subject information comprises results (e.g., data) of a radiological assessment (such as magnetic resonance imaging (MRI), or computed axial tomography scan (CT or CAT scan)) of the subject, a functional or quality of life assessment of the subject (such as expanded disability status scale (EDSS) or multiple sclerosis functional composite score (MSFC)), or both. In some embodiments, the subject undergoes a brain MRI assessment, or radiological evaluation for brain volume (e.g., T2-weighted axial images can be used to calculate the parenchymal fraction in order to assess brain volume), or the subject undergoes an MRI assessment for the presence of GEL). In some embodiments, the radiological assessment includes obtaining a brain or a spine radiological image or series of images (e.g., MRI, X-ray images, or CT), or data representative of the image (image data) from the subject. In some embodiments, the subject undergoes a pre-treatment functional assessment or quality of life assessment such as the EDSS, MSFC z-score, Scripps Neurologic Rating Scale (SNRS), Krupp Fatigue Severity Scale (FSS), Incapacity Status Scale (ISS), Functional Independence Measure (FIM), Ambulation Index (AI), Cambridge Multiple Sclerosis Basic Score (CAMBS), Functional Assessment of Multiple Sclerosis (FAMS), Profile of Mood States (POMS), Sickness Impact Profile (SIP), Guy's Neurological Disability Scale (GNDS), or a combination of two or more of the foregoing, and the results of this assessment are used to determine a patient's eligibility to receive treatment.

In some aspects, the present invention is directed to methods for treating a subject in need thereof with an oxazaphosphorine. In some embodiments, the methods include obtaining subject information relating to the existence of one or more contraindication factors; determining whether oxazaphosphorine treatment is contraindicated based on the information relating to one or more contraindication factors; and administering oxazaphosphorine only if oxazaphosphorine treatment is not contraindicated.

In some embodiments, the contraindication factors include an ALDH inhibition factor, e.g., hormonal contraceptive use, tobacco use, chronic alcohol use and any combinations thereof. In some embodiments, the contraindication factors include use of at least one ALDH inhibiting agent or at least one ALDH activating agent. ALDH inhibiting agents include, but are not limited to disulfiram, calcium carbimide, diazepam, chlordiazepoxide, isosorbide dinitrate, nitroglycerine, chlorpropamide, tolazamide, and cephalosporin.

In some embodiments, permitting delivery comprises generating a prescription approval code to be retrieved by a pharmacy before a prescription is filled. In some embodiments, to ensure that the correct subject is matched with the correct oxazaphosphorine (and, preferably, the correct dose of oxazaphoshorine), the container containing at least one dose of the oxazaphosphorine is tagged (affixed or otherwise associated with) with the authorized subject's unique identifying information (e.g., a bar code).

In some embodiments, the methods further include counseling the patient as to risk avoidance measures in response to the information relating to the existence of one or more contraindication factors.

In some aspects, the present invention is directed to methods for determining a safe and effective dose of an oxazaphosphorine for treatment of a subject in need thereof. In some embodiments, the methods include obtaining information relevant to a sensitivity factor of a subject selected from the group consisting of: white blood cell count, ALDH in lymphocytes, ALDH in hematopoietic progenitor stem cells or any combinations thereof and determining safe and effective dose of an oxazaphosphorine informed by one or more of the sensitivity factors.

In some embodiments, the methods further include administering an ALDH inhibiting agent or an ALDH activating agent to the subject before, during or after determining the safe and effective dose of an oxazaphosphorine. In some embodiments, the ALDH inhibiting agent comprises disulfiram.

In some aspects, the present invention is directed to methods for treating a subject in need thereof with an oxazaphosphorine. In some embodiments, the methods include obtaining information relevant to a sensitivity factor of a subject selected from the group consisting of: white blood cell count, ALDH in lymphocytes or ALDH in hematopoietic progenitor stem cells and combinations thereof; determining a safe and effective dose of an oxazaphosphorine informed by one or more of the sensitivity factors; and administering the safe and effective dose of the oxazaphosphorine to the subject.

In some embodiments, the information is obtained before a treatment is commenced or recommenced. In some embodiments, the information is obtained during treatment and the safe and effective dose is adjusted based on the information during treatment.

In some embodiments, the methods further include administering an ALDH inhibiting agent or an ALDH activating agent to the subject before, during or after determining the safe and effective dose of an oxazaphosphorine and before said administering the safe and effective dose of an oxazaphosphorine. In some embodiments, the ALDH inhibiting agent comprises disulfiram.

In some aspects, the present invention is directed to methods for treating a subject having a neurological immune disorder. In some embodiments, the methods include administering a lymphocytoxic non-myeloablative amount of a oxazaphosphorine drug to the subject, such that the subject's immune system reconstitutes without stem cell transplantation, and wherein the subject has substantial disability observable or equivalent to an Expanded Disability Status Scale (EDSS) score of between about 2 and about 6.5 at time of treatment.

In some embodiments, the neurological immune disorder is chronic inflammatory demyelinating polyneuropathy. In some embodiments, the neurological immune disorder is not chronic inflammatory demyelinating polyneuropathy. In some embodiments, the disorder is an autoimmune disorder. In some embodiments, the disorder is multiple sclerosis (MS). In some embodiments, the disorder is relapsing remitting (RRMS). In some embodiments, the disorder is aggressive RRMS. In some embodiments, the subject suffering from MS exhibits at least one of the following characteristics: failure to respond to conventional therapy for multiple sclerosis; at least two gadolinium enhancing lesions; at least one clinical exacerbation in the year preceding said administering; or a sustained increase of =1.0 on the Kurtzke expanded disability status scale (EDSS) in the year preceding delivery or administration of the oxazaphosphorine.

In some embodiments, the disorder remains in remission without administration of additional immunosuppressive agents.

In some embodiments, the subject has had one or more relapses within the 12 months preceding the oxazaphosphorine treatment. In some embodiments, the subject has one or more total gadolinium enhancing lesions on a brain and/or spinal cord magnetic resonance imaging (MRI), or one or more large enhancing lesions measuring at least about 1 centimeter, within about 18 months prior to the oxazaphosphorine treatment. In some embodiments, the subject has one or more total gadolinium enhancing lesions on a brain and/or spinal cord magnetic resonance imaging (MRI), or one or more large enhancing lesions measuring at least about 1 centimeter, within about one year prior to the oxazaphosphorine treatment. In some embodiments, the subject has sustained increase of equal to or greater than about 1.0 on the EDSS.

In some embodiments, the subject has undergone conventional immunomodulatory treatment for the neurological immune disorder. In some embodiments, the subject has undergone conventional immunomodulatory treatment for the neurological immune disorder and has experienced clinical progression despite the conventional treatment. In some embodiments, the subject has substantial disability observable or equivalent to an EDSS score of between about 2 and about 6.0 at time of the oxazaphosphorine treatment.

In some embodiments, the subject exhibits sustained improvement in disability following the oxazaphosphorine treatment. In some embodiments, the sustained improvement comprises improvement that is observable or equivalent to a change in EDSS score of equal to or greater than a 1 point decrease for at least two consecutive assessments.

In some embodiments, methods further include identifying the subject as suffering from the neurological immune disorder.

In some embodiments, the methods or systems in accordance with the present invention further include monitoring viral titers taken from the subject subsequent to oxazaphosphorine administration.

In some embodiments of the methods or systems of the present invention, the method or system is computer-implemented.

In some aspects the present invention provides a computer-readable storage medium holding computer executable instructions for carrying out at least one of the methods or systems in accordance with the present invention.

In some aspects, the present invention is directed to methods for determining whether a subject is suitable for high-dose oxazaphosphorine therapy. In some embodiments, the methods include determining whether the subject has undergone treatment with an autologous, anti-idiotype vaccine; and selecting a subject as non-suitable for high-dose oxazaphosphorine therapy where it is determined that the subject has undergone treatment for a B cell malignancy with the autologous, anti-idiotype vaccine and has achieved complete remission following vaccination. In some embodiments, the autologous, anti-idiotype vaccine comprises the BIO-VAXID® vaccine.

In some aspects, the present invention is directed to methods for treating multiple sclerosis in a subject in need thereof with an oxazaphosphorine. In some embodiments, the methods include determining whether treatment with an oxazaphosphorine can be safe and effective for the subject based on one or more safety or efficacy factors; and treating the subject with the oxazaphosphorine if it is determined that treatment with oxazaphosphorine can be safe and effective; and monitoring viral titers taken from the subject subsequent to oxazaphosphorine administration. In some embodiments, the viral titers are monitored for at least about 30 days subsequent to oxazaphosphorine administration.

In some aspects, the present invention is directed to a method for treating a subject in need thereof with a lymphocytotoxic, non-myeloablative amount of an oxazaphosphorine, the method comprising: (a) obtaining an ALDH level in a sample of hematopoietic progenitor stein cells obtained from the subject; and (b) if the obtained ALDH level is consistent with a sensitive ALDH level in hematopoietic progenitor stem cells, (i) withholding the lymphocytotoxic, non-myeloablative amount of oxazaphosphorine from the subject, or (ii) administering the lymphocytotoxic, non-myeloablative amount of oxazaphosphorine to the subject followed by rescue therapy with bone marrow transplant and/or stem cell transplant. In some embodiments, the method further comprises determining the presence or absence of an ALDH inhibiting agent in the subject prior to (b). In some embodiments, the lymphocytotoxic, non-myeloablative amount of oxazaphosphorine is 50 mg/kg/day for four consecutive days.

In some aspects, the present invention is directed to a method for treating a subject in need thereof with a lymphocytotoxic, non-myeloablative amount of an oxazaphosphorine, the method comprising: (a) determining the presence or absence of an ALDH inhibiting agent in the subject, or determining whether the subject has otherwise been exposed to an ALDH inhibiting agent; and (b) if an ALDH inhibiting agent is present in the subject or the subject has otherwise been exposed to an ALDH inhibiting agent, (i) withholding the lymphocytotoxic, non-myeloablative amount of oxazaphosphorine from the subject, or (ii) administering a reduced dose of the lymphocytotoxic, non-myeloablative amount of oxazaphosphorine to the subject, or (iii) administering the lymphocytotoxic, non-myeloablative amount of oxazaphosphorine to the subject followed by rescue therapy with bone marrow and/or stem cell transplant (e.g., allogenic bone marrow and/or stem cell transplant). In some embodiments, the reduced dose of (b)(ii) is less than 200 mg per kg of the subject's weight (e.g., less than 50 mg/kg/day, for four consecutive days). In some embodiments, the method further comprises obtaining an ALDH level in a sample of hematopoietic progenitor stem cells obtained from the subject prior to (b).

In some aspects, the present invention is directed to a method for treating a subject in need thereof with a lymphocytotoxic, non-myeloablative amount of an oxazaphosphorine, the method comprising: (a) obtaining an ALDH level in a sample of peripheral lymphocytes obtained from the subject; and (b) if the obtained ALDH level is consistent with a resistant ALDH level in peripheral lymphocytes, (i) withholding the lymphocytotoxic, non-myeloablative amount of oxazaphosphorine from the subject, or (ii) administering an increased dose of the lymphocytotoxic, non-myeloablative amount of oxazaphosphorine to the subject. In some embodiments, the method further comprises, prior to (b), determining the presence or absence of an ALDH activating agent in the subject, or determining whether the subject has otherwise been exposed to an ALDH activating agent.

In some aspects, the present invention is directed to a method for treating a subject in need thereof with a lymphocytotoxic, non-myeloablative amount of an oxazaphosphorine, the method comprising: (a) determining the presence or absence of an ALDH activating agent in the subject, or determining whether the subject has otherwise been exposed to an ALDH activating agent; and (b) if an ALDH activating agent is present in the subject or the subject has otherwise been exposed to an ALDH activating agent, (i) withholding the lymphocytotoxic, non-myeloablative amount of oxazaphosphorine from the subject, or (ii) administering an increased dose of the lymphocytotoxic, non-myeloablative amount of oxazaphosphorine to the subject. In some embodiments, the method further comprises obtaining an ALDH level in a sample of peripheral lymphocytes obtained from the subject prior to (b).

An aspect of the invention includes a method for oxazaphosphorine re-treatment, comprising re-administering an oxazaphosphorine to a subject if the subject is determined to have a white blood cell (WBC) count that is consistent with incomplete immunosuppression. In some embodiments, a WBC of greater than zero is consistent with incomplete immunosuppression.

An aspect of the invention includes a method for identifying a subject suitable for oxazaphosphorine re-treatment, comprising determining the number of WBC in a blood sample obtained from the subject following an oxazophosphorine treatment, wherein the subject is identified as being suitable for oxazaphosphorine re-treatment if the number of WBC is consistent with incomplete immunosuppression. In some embodiments, the method further comprises administering an oxazaphosphorine to the subject identified as being suitable for oxazaphosphorine re-treatment. In some embodiments, the method further comprises repeating the determining step one or more times by obtaining one or more additional samples (e.g., serially) over time and determining the number of WBC in a sample until complete immunosuppression is achieved or to monitor immunosuppression.

BRIEF DESCRIPTION OF THE FIGURES

FIG. 1 is a table showing ALDH levels and WBC levels in the 9 human patients with aggressive relapsing-remitting multiple sclerosis that received 50 mg/kg/day cyclophosphamide intravenously for four days ("geoaldh"=geometric mean of the ALDH values for that patient; "CD4stimgeo"=CD4 counts; "CD8geo"=CD8 counts; and "newavgnadirwbc over 6 days"=nadir WBC over 6 days).

FIG. 2 is a table showing that Spearman's correlation coefficient of geometric ALDH levels and the 6 day average minimal WBC level was 0.800 with a p value of 0.010 (highly statistically significant).

DETAILED DESCRIPTION

Figure 3:
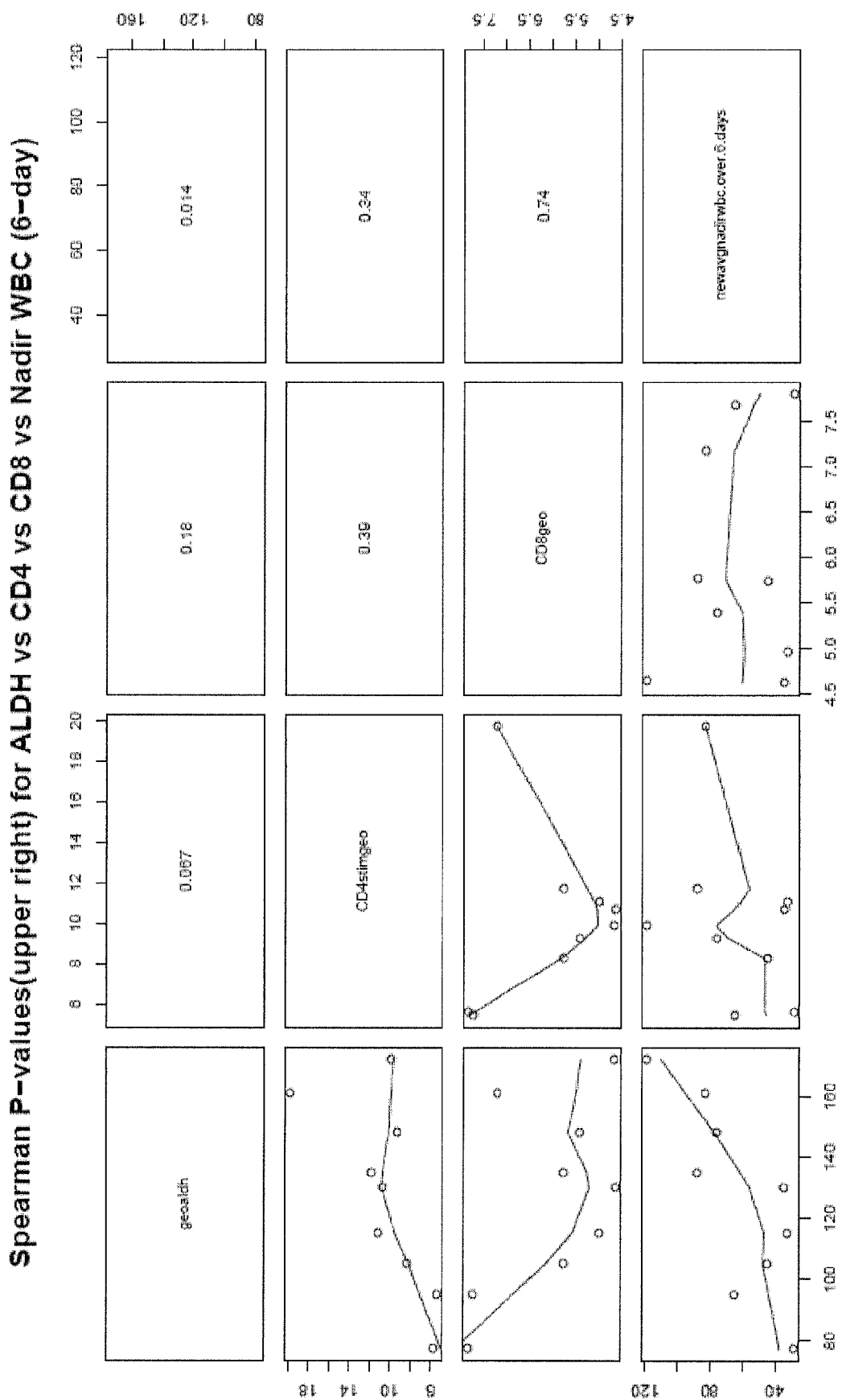
FIG. 3 is a plot of Spearman P-values (upper right) for ALDH versus CD4 vs. CD8 vs. Nadir WBC (6-day). The upper right panel compares geometric ALDH to the 6-day nadir WBC, with a p-value of 0.014. The lower left panels are scatter plots of ALDH versus WBC, matching the corresponding panels with the p-values.

The present invention is based, at least in part, on the discovery that certain factors, e.g., safety and efficacy factors, are important considerations in the treatment of subjects with oxazaphosphorine drugs. For example, the present invention is based, at least in part, on the fact that measurement and monitoring of ALDH levels in both high-dose and low-dose oxazaphosphorine treatment (e.g., prior to and/or during treatment) leads to safer and more efficacious treatment regimens. Moreover, the present invention is based, at least in part, on the discovery that certain pharmaceuticals and lifestyle attributes will influence the efficacy of oxazaphosphorine drugs. Without wishing to be bound by any particular theory, it is believed that this is due, in part, to the effect that such pharmaceuticals and lifestyle attributes exert on ALDH levels in peripheral lymphocytes. For example, increased alcohol or tobacco use may lead to inhibition of ALDH levels or activity. Consequently, conventional oxazaphosphorine treatment would lead to administration of more oxazaphosphorine than is necessary and desirable from both a safety and efficacy perspective. Similarly, exposure to disulfiram or hormonal contraceptives may also lead to inhibition of ALDH levels or activity, affording the same result. These variations in risk and efficacy due to the influence of modulators of ALDH level or activity should be taken into consideration for any treatment regimen utilizing an oxazaphosphorine drug.

Furthermore, enhanced vulnerability of granulocytes to oxazaphosphorines due to ALDH inhibition by agents such as drugs, diet (e.g., alcohol), and supplements that reduce ALDH activity could lead to greater risk and degree of unwanted and dangerous granulocytopenia. While this situation may increase the susceptibility of cancer cells to the oxazaphosphorine, it increases the risk of infection, so administration of a reduced dosage of oxazaphosphorine or administration of a non-oxazaphosphorine cytotoxic agent would be more appropriate in such patients.

Another important consideration in the treatment of patients with oxazaphosphorines is rate of granulocyte recovery, which is a function of hematopoietic progenitor stem cell activity. Inhibition of ALDH activity in a patient's hematopoietic progenitor stem cells due to the influence of ALDH inhibition agents can also cause an unanticipated delay in the recovery of granulocyte count following oxazaphosphorine treatment (high-dose or low dose oxazaphosphorine treatment). Thus, measuring ALDH levels (prior to and/or during treatment) and/or determining the presence or absence, or influence of, an ALDH inhibition agent in a patient will facilitate safer and more efficacious treatment regimens.

Oxazaphosphorine drugs such as cyclophosphamide are lymphocytotoxic but normally spare hematopoietic progenitor stem cells because of high levels of ALDH in those cells. As a prodrug, cyclophosphamide is converted to 4-hydroxycyclophosphamide (4HC) and its tautomer aldophosphamide in the liver. These compounds diffuse into cells and are converted into the active compound phosphoramide mustard. Alternatively, they are inactivated by the enzyme aldehyde dehydrogenase to form the inert carboxyphosphamide. Lymphoid cells, including NK cells, and B and T lymphocytes, have low levels of aldehyde dehydrogenase and are rapidly killed by high-doses (i.e., lymphocytotoxic) of cyclophosphamide. In contrast, hematopoietic progenitor stem cells possess high levels of aldehyde dehydrogenase, rendering them resistant to cyclophosphamide. (Hilton, *Cancer Res.* 44:5156-5160 (1984); Kastan et al., *Blood* 75:1947-1950 (1990); Zoumbos et al., *N. Eng. J. Med.* 312:257-265 (1985); Brodsky, *Sci. World J.* 2:1808-1815 (2002)).

Increased and dependent ALDH activity has been identified as a mechanism of anti-tumor drug resistance to cyclophosphamide. For example, in vivo studies in mice have demonstrated that a cytosolic ALDH isozyme found in murine tumor tissue is responsible for conferring cyclophosphamide resistance. (Russo et al., *Enzyme and Mol. Biol. of Carbonyl Metabolism* 2:65-79 (1989)). Elevated levels of ALDH have also been characterized as being associated with cellular resistance to cyclophosphamide in L1210 murine lymphocytic leukemia model, where a 200-fold higher cytosolic ALDH activity was reported in a cell line resistant to cyclophosphamide when compared to a sensitive cell-line. (DeWys, *J Natl Cancer Inst* 50:783-789 (1973)). Additionally, ALDH levels in the peripheral lymphocytes that are the targets of high-dose oxazaphosphorine treatment may render those cells resistant to cyclophosphamide and other oxazaphosphorines and can lead to worsened clinical outcome or disease relapse.

Although ALDH has previously been used for enriching a cell population for hematopoietic progenitor stem cells, ALDH can also be used for predicting successful outcomes with oxazaphosphorine treatment by using it as an indicator in methods for identifying those patients that may be suitable for oxazaphosphorine treatment, as well as an indicator in methods for determining an appropriate dosage of oxazaphosphorine for therapy, e.g., a low dose which will specifically target tumor cells, but not peripheral lymphocytes, or a high dose which will be lymphocytotoxic but not target hematopoietic progenitor stem cells. Without wishing to be bound by any particular theory, it is believed that this is especially useful in determining which patients are likely to most benefit from the administered therapy.

The present invention is also based, at least in part, on the discovery that WBC count may be used as an indicator for identifying patients that are suitable for initial oxazaphosphorine treatment, as well as retreatment with oxazaphosphorine drugs.

The inventors recognize that determining the ALDH level or activity in peripheral lymphocytes from subjects, determining the ALDH level or activity in hematopoietic progenitor stem cells from subjects, and/or determining the number of WBC in subjects, can be used to identify a safe and effective dose of oxazaphosphorine, as well as to identify subjects in whom treatment will be safe and effective and to treat such subjects.

In some aspects, the present invention is directed to a method for treating a subject in need thereof with an oxazaphosphorine, the method comprising: determining whether treatment with an oxazaphosphorine can be safe and effective for the subject based on one or more safety or efficacy factors; and treating the subject with the oxazaphosphorine if it is determined that treatment with the oxazaphosphorine can be safe and effective. In some aspect, the present invention is directed to a method for selecting a subject suitable for oxazaphosphorine therapy, comprising: determining whether treatment with an oxazaphosphorine can be safe and effective for the subject based on one or more safety or efficacy factors and selecting a subject suitable for oxazaphosphorine therapy where it is determined that treatment can be safe and effective. In some embodiments, the present invention is directed to a system for ensuring the safety or efficacy of a treatment that includes oxazaphosphorine administration, the system comprising: selecting a set of safety and efficacy factors associated with the safe and effective treatment of a subject with an oxazaphosphorine drug; defining a set of information to be obtained from a subject including information probative of the set of selected safety and efficacy factors associated with the safe and effective treatment of a subject with an oxazaphosphorine drug determining whether treatment that includes an oxazaphosphorine administration can be safe and effective for the subject based on the set of information; and generating a prescription approval code if it is determined that the treatment including the oxazaphosphorine administration can be safe and effective. In some embodiments, the present invention is directed to a method for delivering an oxazaphosphorine to subjects in need thereof while restricting access to the oxazaphosphorine by subjects for whom the drug may be contraindicated, said method comprising: obtaining subject information relating to the existence of one or more contraindication factors; and permitting delivery of the oxazaphosphorine only after it has been determined that the subject can safely be treated based on the information relating to one or more contraindication factors. In some embodiments, the one or more contraindication factors comprise one or more ALDH inhibition factors, one or more ALDH activation factors, or both.

Some aspects of the invention are directed to methods for treating a subject in need thereof with an oxazaphosphorine, such as a lymphocytotoxic, non-myeloablative amount of an oxazaphosphorine. In some aspects, the present invention is directed to a method for treating a subject in need thereof with an oxazaphosphorine, the method comprising: obtaining subject information relating to the existence of one or more contraindication factors; determining whether oxazaphosphorine treatment is contraindicated based on the information relating to one or more contraindication factors; and administering an oxazaphosphorine only if oxazaphosphorine treatment is not contraindicated. In some embodiments, the one or more contraindication factors comprise one or more ALDH inhibition factors, one or more ALDH activation factors, or both.

Some aspects of the invention are directed to a method for treating a subject in need thereof with a lymphocytotoxic, non-myeloablative amount of an oxazaphosphorine, the method comprising: (a) obtaining an ALDH level in a sample of hematopoietic progenitor stem cells obtained from the subject; and (b) if the obtained ALDH level is consistent with a sensitive ALDH level in hematopoietic progenitor stem cells, (i) withholding the lymphocytotoxic, non-myeloablative amount of oxazaphosphorine from the subject, or (ii) administering the lymphocytotoxic, non-myeloablative amount of oxazaphosphorine to the subject followed by rescue therapy with bone marrow transplant and/or stem cell transplant. In some embodiments, the method further comprises, prior to (b), after (b), or both prior to and after (b), determining the presence or absence of an ALDH inhibiting agent in the subject, or determining whether the subject has otherwise been exposed to an ALDH inhibiting agent. Some aspects of the invention are directed to a method for treating a subject in need thereof with a lymphocytotoxic, non-myeloablative amount of an oxazaphosphorine, the method comprising: (a) determining the presence or absence of an ALDH inhibiting agent in the subject, or determining whether the subject has otherwise been exposed to an ALDH inhibiting agent; and (b) if an ALDH inhibiting agent is present in the subject or the subject has otherwise been exposed to an ALDH inhibiting agent, (i) withholding the lymphocytotoxic, non-myeloablative amount of oxazaphosphorine from the subject, or (ii) administering a reduced dose of the lymphocytotoxic, non-myeloablative amount of oxazaphosphorine to the subject, or (iii) administering the lymphocytotoxic, non-myeloablative amount of oxazaphosphorine to the subject followed by rescue therapy with bone marrow and/or stem cell transplant. In some embodiments, the method further comprises, prior to (b), after (b), or both prior to and after (b), obtaining an ALDH level in a sample of hematopoietic progenitor stem cells obtained from the subject.

Some aspects of the invention are directed to a method for treating a subject in need thereof with a lymphocytotoxic, non-myeloablative amount of an oxazaphosphorine, the method comprising: (a) obtaining an ALDH level in a sample of peripheral lymphocytes obtained from the subject; and (b) if the obtained ALDH level is consistent with a resistant ALDH level in peripheral lymphocytes, (i) withholding the lymphocytotoxic, non-myeloablative amount of oxazaphosphorine from the subject, or (ii) administering an increased dose of the lymphocytotoxic, non-myeloablative amount of oxazaphosphorine to the subject. In some embodiments, the method further comprises, prior to (b), after (b), or both prior to and after (b), determining the presence or absence of an ALDH activating agent in the subject, or determining whether the subject has otherwise been exposed to an ALDH activating agent. Some aspects of the invention are directed to a method for treating a subject in need thereof with a lymphocytotoxic, non-myeloablative amount of an oxazaphosphorine, the method comprising: (a) determining the presence or absence of an ALDH activating agent in the subject, or determining whether the subject has otherwise been exposed to an ALDH activating agent; and (b) if an ALDH activating agent is present in the subject or the subject has otherwise been exposed to an ALDH activating agent, (i) withholding the lymphocytotoxic, non-myeloablative amount of oxazaphosphorine from the subject, or (ii) administering an increased dose of the lymphocytotoxic, non-myeloablative amount of oxazaphosphorine to the subject. In some embodiments, the method further comprises, prior to (b), after (b), or both prior to and after (b), obtaining an ALDH level in a sample of peripheral lymphocytes obtained from the subject.

Some aspects of the invention are directed to treating a subject in need thereof with a cytotoxic agent, such as an oxazaphosphorine or non-oxazaphosphorine cytotoxic agent (e.g., a cytotoxic agent the cytoxicity of which is not inhibited by ALDH). In some aspects, the present invention is directed to a method for treating a subject in need thereof with a cytotoxic agent, the method comprising: (a) obtaining an ALDH level in a sample of granulocytes obtained from the subject; and (b) administering: (i) an oxazaphosphorine to the subject if the obtained ALDH level is consistent with a resistant ALDH level in granulocytes, or (ii) a reduced dose of the oxazaphosphorine to the subject if the obtained ALDH level is consistent with a sensitive ALDH level in granulocytes, or (iii) a non-oxazaphosphorine cytotoxic agent to the subject if the obtained ALDH level is consistent with a sensitive ALDH level in granulocytes. In some embodiments, method further comprises, prior to (b), after (b), or both prior to and after (b), determining the presence or absence of an ALDH inhibiting agent in the subject, or determining whether the subject has otherwise been exposed to an ALDH inhibiting agent.

Some aspects of the invention are directed to a method for treating a subject in need thereof with a cytotoxic agent, the method comprising: (a) determining the presence or absence of an ALDH inhibiting agent in the subject, or determining whether the subject has otherwise been exposed to an ALDH inhibiting agent; and (b) administering: (i) an oxazaphosphorine to the subject if an ALDH inhibiting agent is not present in the subject or if the subject has not otherwise been exposed to an ALDH inhibiting agent, or (ii) a reduced dose of the oxazaphosphorine to the subject if an ALDH inhibiting agent is present in the subject or if the subject has otherwise been exposed to an ALDH inhibiting agent, or (iii) a non-oxazaphosphorine cytotoxic agent to the subject if an ALDH inhibiting agent is present in the subject or if the subject has otherwise been exposed to an ALDH inhibiting agent. In some embodiments, the method further comprises, prior to (b), after (b), or both prior to and after (b), obtaining an ALDH level in a sample of granulocytes obtained from the subject.

Some aspects of the invention are directed to a method for treating a subject in need thereof with a cytotoxic agent, the method comprising: (a) determining the presence or absence of an ALDH activating agent in the subject, or determining whether the subject has otherwise been exposed to an ALDH activating agent; and (b) if an ALDH activating agent is present in the subject or the subject has otherwise been exposed to an ALDH activating agent, (i) administering an increased dose of an oxazaphosphorine to the subject, or (ii) administering a non-oxazaphosphorine cytotoxic agent to the subject.

Some aspects of the invention are directed to methods for selecting a subject suitable for treatment with a lymphocytotoxic, non-meyloablative amount of an oxazaphosphorine. Some aspects of the invention are directed a method for selecting a subject suitable for a lymphocytotoxic, non-myeloablative amount of an oxazaphosphorine, the method comprising: (a) obtaining an ALDH level in a sample of hematopoietic progenitor stem cells obtained from the subject; and (b) if the obtained ALDH level is consistent with a sensitive ALDH level in hematopoietic progenitor stem cells, (i) withholding the lymphocytotoxic, non-myeloablative amount of oxazaphosphorine from the subject, or (ii) selecting the subject for administration of the lymphocytotoxic, non-myeloablative amount of oxazaphosphorine to the subject followed by rescue therapy with bone marrow transplant and/or stem cell transplant. In some embodiments, the method further comprises, prior to (b), after (b), or both prior to and after (b), determining the presence or absence of an ALDH inhibiting agent in the subject, or determining whether the subject has otherwise been exposed to an ALDH inhibiting agent. Some aspects of the invention are directed to a method for selecting a subject suitable for a lymphocytotoxic, non-myeloablative amount of an oxazaphosphorine, the method comprising: (a) determining the presence or absence of an ALDH inhibiting agent in the subject, or determining whether the subject has otherwise been exposed to an ALDH inhibiting agent; and (b) if an ALDH inhibiting agent is present in the subject or the subject has otherwise been exposed to an ALDH inhibiting agent, (i) withholding the lymphocytotoxic, non-myeloablative amount of oxazaphosphorine from the subject, or (ii) selecting the subject for administration of a reduced dose of the lymphocytotoxic, non-myeloablative amount of oxazaphosphorine to the subject, or (iii) selecting the subject for administration of the lymphocytotoxic, non-myeloablative amount of oxazaphosphorine to the subject followed by rescue therapy with bone marrow and/or stem cell transplant. In some embodiments, the method further comprises, prior to (b), after (b), or both prior to and after (b), obtaining an ALDH level in a sample of hematopoietic progenitor stem cells obtained from the subject. Some aspects of the invention are directed to a method for selecting a subject suitable for a lymphocytotoxic, non-myeloablative amount of an oxazaphosphorine, the method comprising: (a) obtaining an ALDH level in a sample of peripheral lymphocytes obtained from the subject; and (b) if the obtained ALDH level is consistent with a resistant ALDH level in peripheral lymphocytes, (i) withholding the lymphocytotoxic, non-myeloablative amount of oxazaphosphorine from the subject, or (ii) selecting the subject for administration of an increased dose of the lymphocytotoxic, non-myeloablative amount of oxazaphosphorine to the subject. In some embodiments, the method further comprises, prior to (b), after (b), or both prior to and after (b), determining the presence or absence of an ALDH activating agent in the subject, or determining whether the subject has otherwise been exposed to an ALDH activating agent.

Some aspects of the invention are directed to a method for selecting a subject suitable for a lymphocytotoxic, non-myeloablative amount of an oxazaphosphorine, the method comprising: (a) determining the presence or absence of an ALDH activating agent in the subject, or determining whether the subject has otherwise been exposed to an ALDH activating agent; and (b) if an ALDH activating agent is present in the subject or the subject has otherwise been exposed to an ALDH activating agent, (i) withholding the lymphocytotoxic, non-myeloablative amount of oxazaphosphorine from the subject, or (ii) selecting the subject for administration of an increased dose of the lymphocytotoxic, non-myeloablative amount of oxazaphosphorine to the subject. In some embodiments, the method further comprises, prior to (b), after (b), or both prior to and after (b), obtaining an ALDH level in a sample of peripheral lymphocytes obtained from the subject.

Some aspects of the invention are directed to a method for treating a subject with a cytotoxic agent, the method comprising: (a) obtaining an ALDH level in a sample of granulocytes obtained from the subject; and (b) administering: (i) an oxazaphosphorine to the subject if the obtained ALDH level is consistent with a resistant ALDH level in granulocytes, or (ii) a reduced dose of the oxazaphosphorine to the subject if the obtained ALDH level is consistent with a sensitive ALDH level in granulocytes, or (iii) a non-oxazaphosphorine cytotoxic agent to the subject if the obtained ALDH level is consistent with a sensitive ALDH level in granulocytes. In some embodiments, the method further comprises, prior to (b), after (b), or both prior to and after (b), determining the presence or absence of an ALDH inhibiting agent in the subject, or determining whether the subject has otherwise been exposed to an ALDH inhibiting agent.

Some aspects of the invention are directed to a method for treating a subject with a cytotoxic agent, the method comprising: (a) determining the presence or absence of an ALDH inhibiting agent in the subject, or determining whether the subject has otherwise been exposed to an ALDH inhibiting agent; and (b) administering: (i) an oxazaphosphorine to the subject if an ALDH inhibiting agent is not present in the subject or if the subject has not otherwise been exposed to an ALDH inhibiting agent, or (ii) a reduced dose of the oxazaphosphorine to the subject if an ALDH inhibiting agent is present in the subject or if the subject has otherwise been exposed to an ALDH inhibiting agent, or (iii) a non-oxazaphosphorine cytotoxic agent to the subject if an ALDH inhibiting agent is present in the subject or if the subject has otherwise been exposed to an ALDH inhibiting agent. In some embodiments, the method further comprises, prior to (b), after (b), or both prior to and after (b), obtaining an ALDH level in a sample of granulocytes obtained from the subject.

Some aspects of the invention are directed to methods for selecting a cytotoxic agent for use in treatment. Some aspects of the invention are directed to a method for selecting a cytotoxic agent for use in treatment, the method comprising: (a) obtaining an ALDH level in a sample of granulocytes obtained from the subject; and (b) selecting: (i) an oxazaphosphorine for administration to the subject if the obtained ALDH level is consistent with a resistant ALDH level in granulocytes, or (ii) a reduced dose of the oxazaphosphorine for administration to the subject if the obtained ALDH level is consistent with a sensitive ALDH level in granulocytes, or (iii) a non-oxazaphosphorine cytotoxic agent for administration to the subject if the obtained ALDH level is consistent with a sensitive ALDH level in granulocytes. In some embodiments, the method further comprises: (c) if the ALDH inhibiting agent is absent or if the subject has not otherwise been exposed to the ALDH inhibiting agent, administering an oxazaphosphorine to the subject.

Some aspects of the invention are directed to a method for selecting a cytotoxic agent for use in treatment, the method comprising: (a) determining the presence or absence of an ALDH inhibiting agent in the subject, or determining whether the subject has otherwise been exposed to an ALDH inhibiting agent; and (b) selecting: (i) an oxazaphosphorine for administration to the subject if an ALDH inhibiting agent is not present in the subject or if the subject has not otherwise been exposed to an ALDH inhibiting agent, or (ii) a reduced dose of the oxazaphosphorine for administration to the subject if an ALDH inhibiting agent is present in the subject or if the subject has otherwise been exposed to an ALDH inhibiting agent, or (iii) a non-oxazaphosphorine cytotoxic agent for administration to the subject if an ALDH inhibiting agent is present in the subject or if the subject has otherwise been exposed to an ALDH inhibiting agent. Some aspects of the invention are directed to a method for selecting a cytotoxic agent for use in treatment, the method comprising: (a) determining the presence or absence of an ALDH activating agent in the subject, or determining whether the subject has otherwise been exposed to an ALDH activating agent; and (b) if an ALDH activating agent is present in the subject or the subject has otherwise been exposed to an ALDH activating agent, (i) selecting an increased dose of an oxazaphosphorine for administration to the subject, or (ii) selecting a non-oxazaphosphorine cytotoxic agent for administration to the subject, or (iii) advising the subject to cease or avoid intake or exposure to the ALDH activating agent.

Some aspects of the invention involve managing or reducing oxazaphorine-induced granulocytopenia. Some aspects of the invention are directed to a method for managing oxazaphosphorine-induced granulocytopenia, comprising: (a) determining the presence or absence of an ALDH inhibiting agent in a subject, or determining whether the subject has otherwise been exposed to an ALDH inhibiting agent; and (b) if an ALDH inhibiting agent is present in the subject or if the subject has otherwise been exposed to an ALDH inhibiting agent, (i) administering a reduced dose of oxazaphosphorine to the subject, or (ii) advising the subject to cease or avoid intake or exposure to the ALDH inhibiting agent, or (iii) administering a non-oxazaphosphorine cytotoxic agent to the subject. Some aspects of the invention are directed to a method for reducing oxazaphosphorine-induced granulocytopenia severity, or delay in granulocyte recovery following oxazaphosphorine-induced granulocytopenia, the method comprising: (a) determining the presence or absence of an ALDH inhibiting agent in a subject, or determining whether the subject has otherwise been exposed to an ALDH inhibiting agent; and (b) if an ALDH inhibiting agent is present in the subject or if the subject has otherwise been exposed to an ALDH inhibiting agent, (i) administering a reduced dose of oxazaphosphorine to the subject, or (ii) advising the subject to cease or avoid intake or exposure to the ALDH inhibiting agent, or (iii) administering a non-oxazaphosphorine cytotoxic agent to the subject. The methods for managing or reducing granulocytopenia can further comprise determining granulocyte count in the subject one or more times after (b)(i) or (b)(ii). In some embodiments, a reduced dose of the oxazaphosphorine is given to the subject in which it is determined that an ALDH inhibiting agent is present or in which it is determined that the subject has otherwise been exposed to an ALDH inhibiting agent, and the subject's granulocyte count is then monitored before continuing with additional doses of the oxazaphosphorine.

In some embodiments of the aforementioned methods of the invention, the one or more safety or efficacy factors include one or more ALDH inhibition factors, one or more ALDH activation factors, or both. In some embodiments of the aforementioned methods of the invention, the one or ALDH inhibition factors includes at least one selected from the group consisting of hormonal contraceptive use, tobacco use, chronic alcohol consumption, and any combinations thereof. In some embodiments of the aforementioned methods of the invention, the one or more ALDH inhibition factors includes at least one ALDH inhibition agent selected from the group consisting of disulfiram, hormonal contraceptive, procarbazine, N-methyltetrazolylthiomethyl bearing beta-lactam, kudzu root product, calcium carbimide, diazepam, chlordiazepoxide, isosorbide dinitrate, nitroglycerine, chlorpropamide, tolazamide, and cephalosporin, or an ALDH inhibiting metabolite thereof. Further examples of ALDH inhibitory agents are listed in Table 1. In some embodiments of the aforementioned methods of the invention, the one or more ALDH inhibition factors are one or more anti-cancer agents (e.g., procarbazine). In some embodiments of the aforementioned methods of the invention, the one or more ALDH inhibition factors are one or more antibiotics. In some embodiments of the aforementioned methods of the invention, the one or more ALDH inhibition factors are one or more dietary constituents such as dietary supplements. In some embodiments of the aforementioned methods of the invention, the one or more ALDH inhibition factors are one or more competitive inhibitors, non-competitive inhibitors, or mixed-type inhibitors of ALDH. In some embodiments of the aforementioned methods of the invention, the one or more ALDH inhibition factors are one or more irreversible inhibitors of ALDH. In some embodiments of the aforementioned methods of the invention, the one or more ALDH inhibition factors are one or more reversible inhibitors of ALDH. In some embodiments of the aforementioned methods of the invention, the one or more ALDH activation factors are one or more ALDH activation agents selected from the group consisting of coffee, oltipraz, *Crucifera* vegetable family member, Liliaceae vegetable family member, and Phenobarbital, or an ALDH activating metabolite of any of the foregoing. Further examples of ALDH activating agents are listed in Table 2. In some embodiments of the aforementioned methods of the invention, the one or more ALDH activation factors are one or more dietary constituents such as dietary supplements.

In some embodiments of the aforementioned methods of the invention, the non-oxazaphosphorine cytotoxic agent is an alkylating agent. In some embodiments of the aforementioned methods of the invention, the non-oxazaphosphorine cytotoxic agent is an antimetabolite, such as azathioprine.

In some embodiments of the aforementioned methods of the invention, the cytotoxic agent is to be administered for treatment of cancer. In some embodiments of the aforementioned methods of the invention, the subject is suffering from an immune disorder, such as an autoimmune disease, an allergic reaction, and transplant rejection. In some embodiments of the aforementioned methods of the invention, the subject is suffering from multiple sclerosis (e.g., relapsing remitting multiple sclerosis). In some embodiments of the aforementioned methods of the invention, the subject is suffering from multiple sclerosis that is refractory (has exhibited resistance to conventional therapy). In some embodiments of the aforementioned methods of the invention, is suffering from, or at risk of developing, transplant rejection. In some embodiments, the method further comprises identifying the subject as one suffering from the immune disorder.

In some embodiments of the aforementioned methods of the invention, the lymphocytotoxic, non-myeloablative amount of oxazaphosphorine is 200 mg/kg intravenously. In some embodiments of the aforementioned methods of the invention, the lymphocytotoxic, non-myeloablative amount of oxazaphosphorine is 50 mg/kg/day intravenously, for four consecutive days. In some embodiments of the aforementioned methods of the invention, the lymphocytotoxic, non-myeloablative amount of oxazaphosphorine is less than 200 mg/kg intravenously.

In some embodiments of the aforementioned methods of the invention, the oxazaphosphorine is to be administered for the treatment or prevention of an immune disorder selected from the group consisting of an autoimmune disease, allergic reaction, and transplant rejection.

In some embodiments of the aforementioned methods of the invention, the oxazaphosphorine is to be administered by a regimen selected from the group consisting of: intravenous administration of about 40 mg/kg to about 50 mg/kg in divided doses over a period of from about 2 to about 5 days, intravenous administration of about 10 mg/kg to about 15 mg/kg oxazaphosphorine every 7 to 10 days, intravenous administration of about 3 mg/kg to about 5 mg/kg twice weekly, and oral administration of about 2.5 mg/kg to about 3 mg/kg daily for about 60 to about 90 days. In some embodiments of the aforementioned methods of the invention, the subject has cancer. In some embodiments, the method further comprises identifying the subject as one suffering from cancer.

In some embodiments of the aforementioned methods of the invention, the reduced dose is 50% or less of a standard therapeutic dose. In some embodiments of the aforementioned methods of the invention, the reduced dose is 33% or less of a standard therapeutic dose. In some embodiments of the aforementioned methods of the invention, the increased dose is at least 50% greater than a standard therapeutic dose. In some embodiments of the aforementioned methods of the invention, the increased dose is at least 33% greater than a standard therapeutic dose.

In some of the aforementioned methods of the invention that comprise determining the presence or absence of an ALDH modulator (an ALDH inhibitor or ALDH activator) in the subject, or determining whether the subject has otherwise been exposed to an ALDH modulator, the method can further comprise determining the ALDH level in a sample from the subject (e.g., a sample of hematopoietic progenitor stem cells, peripheral lymphocytes, or granulocytes), particularly if the presence of both an ALDH inhibitor and an ALDH activator is determined or if it is determined that the subject has otherwise been exposed to both an ALDH inhibitor and an ALDH activator, which may still be exerting effects on ALDH level in the relevant cell population.

In some embodiments of the aforementioned methods of the invention, the oxazaphosphorine is selected from the group consisting of cyclophosphamide, ifosfamide, perfosfamide, trophosphamide, 4-hydroxycyclophosphamide, aldophosphamide, and a pharmaceutically acceptable salt, solvate, prodrug, or active metabolite of any of the foregoing.

In some embodiments of the aforementioned methods of the invention, one or more steps of the method are computer-implemented.

In some aspects the present invention provides a computer-readable storage medium holding computer executable instructions for carrying out at least one of the methods or systems in accordance with the present invention.

DEFINITIONS

In order that the present disclosure may be more readily understood, certain terms are first defined. Additional definitions are set forth throughout the detailed description.

As used herein, the term "ALDH" or "aldehyde dehydrogenase" refers to an enzyme or a class of enzymes which are capable of oxidizing aldehydes. Aldehyde dehydrogenase (ALDH) (Enzyme Commission 1.2.1.3) is an enzyme responsible for oxidizing intracellular aldehydes and plays an important role in metabolism of ethanol, vitamin A, cyclophosphamide and other oxazaphosphorines. Substrates for ALDH include acetyldehyde and biogenic amines produced during catecholamine catabolism. (Russo et al., *Cancer Res.* 48: 2963-2968 (1988)). ALDH has also been reported to play a crucial role in the conversion of vitamin A to its active metabolite, retinoic acid. (Labrecque et al., *Biochem. Cell Biol.* 71:85-89 (1993); Yoshida et al., *Enzyme* 46:239-244 (1992)). The ALDH level or activity can comprise the level or activity of one or multiple ALDH enzymes. Examples of ALDH enzymes in humans include ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, ALDH18A1. As used herein, phrases such as "measuring ALDH" is intended to mean measuring ALDH enzyme, measuring ALDH activity, or both.

In some embodiments, the ALDH level or activity determined is selected from the group consisting of ALDH-1 (e.g., ALDH1A1, ALDH1A3, ALDH1B1, ALDH1L1, ALDH1L2), ALDH-2, and ALDH-3 (e.g., ALDH3A1, ALDH3A2, ALDH3B1, ALDH3B2), or a combination of two or more of the foregoing (e.g., ALDH-1 and ALDH-3). In some embodiments, the ALDH level or activity determined is ALDH-1 and ALDH-3 (e.g., ALDH1A1 and ALDH-3A1). In some embodiments, the ALDH level or activity determined is ALDH-2. In some embodiments, the ALDH level or activity determined is ALDH-1, ALDH-2, and ALDH-3.

As of 2007, 19 ALDH families have been so far identified. (Russo et al., *Cancer Res.* 48:2963-2968 (1988) and the Aldehyde Dehydrogenase Gene Superfamily Resource at http://www.aldh.org/superfamily.php#ALDH7; accessed August 2008). Both hematopoietic progenitors and intestinal crypt stem cells display high levels of cytosolic ALDH and consequently are relatively resistant to cyclophosphamide. Although all hematopoietic progenitors are known to express relatively high levels of cytosolic ALDH, both mouse as well as human hematopoietic stem cells (HSCs) appear to express even higher levels of ALDH than their less primitive counterparts. Accordingly, primitive hematopoietic progenitors are generally more resistant to 4-hydroxycyclophosphamide than later progenitors.

The term "ALDH level", as used herein, is inclusive of the amount of ALDH enzyme and the amount of ALDH enzymatic activity. Thus, reference only to "ALDH level" should be read to mean the amount of ALDH enzyme, the amount of ALDH enzymatic activity, or both.

The terms "oxazaphosphorine" and "oxazaphosphorine drug" refer interchangeably to a class of drugs which act as alkylating agents and cause immunoablation. They are generally highly cytotoxic and are often used as chemotherapeutic agents. In some embodiments, oxazaphosphorines include compounds of formula (I):

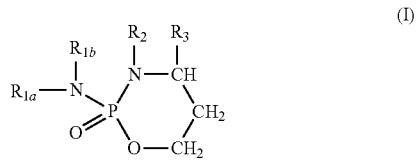

wherein $R_{1a}$ and $R_{1b}$ are each independently selected from —H, —$(CH_2)_n$Cl, or —$(CH_2)_n SO_3 CH_3$; provided that $R_{1a}$ and $R_{1b}$ are not both —H;

$R_2$ is selected from —H or —$(CH_2)_n$Cl;

$R_3$ is selected from —H, —OOH or —$(CH_2)_n SO_3^-$;

n is, independently for each occurrence, an integer from 1 to 3; and and pharmaceutically acceptable salts, solvates, prodrugs and metabolites thereof. Examples of oxazaphosphorine drugs include, but are not limited to, cyclophosphamide, ifosfamide, perfosfamide, trophosphamide (trofosfamide), and pharmaceutically acceptable salts, solvates, prodrugs and metabolites thereof. In some embodiments, an oxazaphosphorine drug used in the methods described herein is cyclophosphamide, which is sold under common trade-names including PROCYTOX®, CYTOXAN® and NEOSAR®. As discussed above, cyclophosphamide is converted to 4-hydroxycyclophosphamide and its tautomer aldophosphamide in the liver and is cytotoxic to cells that express low levels of the enzyme aldehyde dehydrogenase, for example, NK cells and T and B lymphocytes.

Ifosfamide (MITOXANAO) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis.

As used herein, the phrase "high-dose oxazaphosphorine" refers to a lymphocytotoxic, non-myeloablative amount of an oxazaphosphorine drug. The phrase "low-dose oxazaphosphorine" refers to an amount that is less than a high-dose amount. As used herein, the phrase "a lymphocytotoxic non-myeloablative amount of an oxazaphosphorine drug" refers to an amount of the drug which is immunoablative, upon single or multiple dose administration to a subject (such as a human patient suffering from an autoimmune disease, an allergic reaction or transplant rejection), thereby resulting in a substantial reduction in or complete elimination of mature circulating lymphocytes in the subject. In some embodiments, administration of a lymphocytotoxic non-myeloablative amount of a oxazaphosphorine drug results in treating, preventing, curing, delaying, reducing the severity of, ameliorating at least one symptom of a disorder or recurring disorder, or prolonging the survival of the subject beyond that expected in the absence of such administration. In some embodiments, "a lymphocytotoxic non-myeloablative amount of an oxazaphosphorine drug" refers to a dose of the drug administered to a subject in need thereof, which results in eliminating or substantially reducing the number of circulating lymphocytes in the subject, including those which are associated with an adverse immune reaction such as, for example, an autoimmune disease, transplant rejection and allergic reaction, while sparing the hematopoietic progenitor stem cells. For example, in some embodiments, "a lymphocytotoxic non-myeloablative amount of a oxazaphosphorine drug" is a 50 mg/kg/day dose of cyclophosphamide or other oxazaphosphorine administered to a subject in need thereof for 4 consecutive days. The use of high-dose oxazaphosphorine for the treatment of certain immune disorders is described, for example, in U.S. Publication No. 2007/0202077, the entire contents of which is incorporated herein by this reference.

The term "non-myeloablative," as used herein, refers to a property of a compound such as, for example, oxazaphosphorine (e.g., cyclophosphamide), whereby the compound does not have a cytotoxic effect on myeloid stem cells, for example, hematopoietic progenitor stem cells. In some embodiments, a non-myeloablative agent used in the methods described herein has a cytotoxic effect on the circulating mature lymphocytes (e.g., NK cells, and T and B lymphocytes) while sparing the progenitor cells, e.g., hematopoietic progenitor stem cells that are capable of reconstituting the immune system. In some embodiments, a non-myeloablative agent used in the methods of the invention kills cells which express low or sensitive levels of the enzyme aldehyde dehydrogenase (e.g., NK cells and B and T lymphocytes) while sparing cells which express high or resistant levels of the enzyme aldehyde dehydrogenase (e.g., hematopoietic progenitor stem cells). In some embodiments, "a non-myeloablative amount of oxazaphosphorine" refers to a dose of cyclophosphamide or other oxazaphosphorine administered to a subject in need thereof, which results in eliminating or substantially reducing the number of circulating lymphocytes in the subject, including those which are associated with an adverse immune reaction such as, for example, an autoimmune disease, transplant rejection and allergic reaction, or which are associated with cancer, while sparing the hematopoietic progenitor stem cells. For example, in some embodiments, "a non-myeloablative amount of oxazaphosphorine" is a 50 mg/kg/day dose of oxazaphosphorine administered to a subject in need thereof for 4 consecutive days. In some embodiments, "a non-myeloablative amount of oxazaphosphorine" is a 50 mg/kg/day dose of cyclophosphamide administered to a subject in need thereof for 4 consecutive days (a non-myeloablative amount of cyclophosphamide).

The term "hematopoietic progenitor stem cell," as used herein refers to any type of cell of the hematopoietic system, including, but not limited to, undifferentiated cells such as hematopoietic stem cells and progenitor cells, which are capable of reconstituting the immune system following administration of a lymphocytotoxic non-myeloablative amount of oxazaphosphorine (e.g., cyclophosphamide) to a subject identified using the methods described herein. Preferably, the hematopoietic progenitor stem cells are hematopoietic stem cells (HSC). In some embodiments, the hematopoietic progenitor stem cells are hematopoietic progenitor cells. In some embodiments, the hematopoietic progenitor stem cells are mature hematopoietic progenitor cells (Gordon M. Y. et al., *Leuk. Res.*, 9:1017-1021 (1985)). In some embodiments, the hematopoietic progenitor stem cells are primitive hematopoietic progenitor cells (Gordon M. Y. et al., (1985)). In some embodiments, the hematopoietic progenitor stem cells are both HSC and hematopoietic progenitor cells.

The terms "peripheral lymphocyte", "differentiated lymphocyte", and "mature lymphocyte", as used interchangeably herein, refer to the immune system cells which are differentiated and distinct from the hematopoietic progenitor stem cells. These can include populations or individual cells of circulating differentiated lymphocytes (e.g., NK cells, and T and B lymphocytes).

The terms "immunoablation" and "immunoablative," as used herein, refer to severe immunosuppression using a high-dose (i.e., lymphocytotoxic non-myeloablative amount) of oxazaphosphorine, for example, 50 mg/kg×4 days of oxazaphosphorine (e.g., cyclophosphamide), which leads to substantial reduction in or elimination of the population of circulating lymphocytes, including for example, NK cells and B and T lymphocytes. Immunoablation, as described herein, results in complete or substantially complete reduction in autoreactive antibodies and memory cells responsible for an autoimmune response.

The term "lymphocytotoxic," as used herein, refers to complete elimination of or substantial reduction in the number of circulating lymphocytes, including those associated with an adverse immune reaction in a subject, such as, for example, an autoimmune disease, an allergic reaction, a transplant rejection, or cancer in a subject following administration of a high-dose (i.e., lymphocytotoxic non-myeloablative amount) of oxazaphosphorine, such as, for example, 50 mg/kg×4 days of oxazaphosphorine (e.g., cyclophosphamide). Substantial reduction can be a reduction of about 5%, 10%, 15%, 20%, 25%, 50%, 75%, 90%, 95%, 98%, 99% of the circulating lymphocytes. The term "lymphocytotoxic," includes killing of those immune cells by a oxazaphosphorine drug which express low levels of the enzyme aldehyde dehydrogenase.

The term "resistant ALDH" refers to a level or activity of ALDH which confers resistance of cells to high-dose oxazaphosphorine (e.g., high-dose cyclophosphamide). By resistance to oxazaphosphorine is meant that the cells, for example, hematopoietic progenitor stem cells or peripheral lymphocytes having an ALDH level or activity equal to or greater than a "resistant ALDH" survive exposure to high-dose oxazaphosphorine. The term "resistant ALDH" also refers to a level or activity of ALDH which is higher than an ALDH level or activity in a cell or cells, for example, a hematopoietic progenitor stem cell or peripheral lymphocyte, which do not survive exposure to high-dose oxazaphosphorine (e.g., high-dose cyclophosphamide).

The terms "non-resistant ALDH" and "sensitive ALDH" in cells refer to the level or activity of ALDH which confers sensitivity or does not confer resistance to high-dose oxazaphosphorine (e.g., high-dose cyclophosphamide). By sensitivity to high-dose oxazaphosphorine it is meant that a cell or cells, for example, hematopoietic progenitor stem cells or peripheral lymphocytes, having an ALDH level or activity less than "resistant ALDH" are killed by exposure to high-dose oxazaphosphorine (e.g., high-dose cyclophosphamide).

In some embodiments, a subject identified as being suitable for high-dose oxazaphosphorine treatment (e.g., high-dose cyclophosphamide treatment) has an ALDH at least 10-fold, or 20-fold, or 30-fold, or 40-fold, or 50-fold or 60-fold, or 70-fold, or 80-fold, or 90-fold, or 100-fold, or 150-fold, or 200-fold, or higher than "resistant ALDH."

In some embodiments, various methodologies of the instant invention include a step that involves comparing ALDH in a sample derived from a subject to a "suitable control," also referred to interchangeably herein as an "appropriate control." A "suitable control" or "appropriate control" is a predetermined value associated with ALDH useful for comparison purposes, which can take many different forms. Exemplary forms include, but are not limited to, for example, a transcription rate, mRNA level, translation rate, protein level, protein structure, biological activity, cellular characteristic or property, genotype, phenotype, enzymatic activity etc. associated with ALDH. In one embodiment, a "suitable control" is a predetermined ALDH activity, which is compared to ALDH activity in a sample derived from a subject being identified as suitable or not suitable for high-dose oxazaphosphorine treatment. In another embodiment, a "suitable control" is a predetermined ALDH level, which is compared to ALDH level in a sample derived from a subject being identified as suitable or not suitable for high-dose oxazaphosphorine treatment. In another embodiment, a "suitable control" is a predetermined ALDH level, which is compared to ALDH level in a sample derived from a subject in which a clinical measure was achieved, for example an ALDH level obtained from cells in a subject who reached or failed to reach a white blood cell count of 0 following oxazaphosphorine treatment.

In some embodiments, a "suitable control" or an "appropriate control" can be a single cut-off value, such as a median or mean. A single cut-off value can be established, for example, based upon comparative groups, such as in groups having an ALDH level or activity which confers resistance to high-dose oxazaphosphorine and groups having an ALDH level or activity which does not confer resistance to high-dose oxazaphosphorine. For example, hematopoietic progenitor stem cell samples or peripheral lymphocyte samples can be derived from various individuals or blood banks and an ALDH level or activity can be measured in each sample prior to being subjected to high-dose oxazaphosphorine. Consequently, a single cut-off value can be based on the mean of an ALDH level or activity in samples which are resistant to high-dose oxazaphosphorine (e.g., cyclophosphamide). Another comparative group can be, for example, an ALDH level or activity in a group of individuals with a family history of successful treatment with high-dose oxazaphosphorine and a group without such a family history. Another comparative group can be, for example, an ALDH level or activity in a group of individuals with a history of treatment with high-dose oxazaphosphorine having achieved maximal immunosuppression and a group having not achieved maximal immunosuppression.

In some embodiments of the methods of the present invention, a subject is identified as being suitable for oxazaphosphorine treatment if the ALDH measured in a hematopoietic progenitor stem cell sample, a peripheral lymphocyte sample, or a granulocyte sample derived from the subject is consistent with an "appropriate control." By "consistent with an appropriate control," is meant that the ALDH is either equal or equivalent to, higher than, or lower than a predetermined ALDH control, in case of a single cut-off value, or the ALDH falls within a range for a predetermined ALDH control. In some embodiments, a subject is identified as being suitable for high-dose oxazaphosphorine treatment if the ALDH measured in a hematopoietic progenitor stem cell sample derived from the subject is consistent with a "resistant ALDH" in hematopoietic progenitor stem cells. By "consistent with a resistant ALDH," is meant that the ALDH is either equal to or higher than a predetermined "resistant ALDH," in case of a single cut-off value, or the ALDH falls within a range for a predetermined resistant ALDH. In other embodiments, a subject is identified as being suitable for high-dose oxazaphosphorine treatment if the ALDH measured in a peripheral lymphocyte cell derived from the subject is consistent with a "sensitive ALDH" in peripheral lymphocytes. By "consistent with a sensitive ALDH," is meant that the ALDH is either equal to or lower than a predetermined "sensitive ALDH," in case of a single cut-off value, or the ALDH falls within a range for a predetermined sensitive ALDH.

The terms "treat," "treating," and "treatment," as used herein, refer to therapeutic or preventative measures described herein. The methods of "treatment" employ administration of a drug such as an oxazaphosphorine (e.g., cyclophosphamide) to a subject that may be identified using methods of the present invention, for example, a subject having an autoimmune disease, an allergic reaction, transplant rejection, or cancer, or who ultimately may acquire a disorder such as, for example, an autoimmune disease, an allergic reaction, transplant rejection, or cancer. The drug is administered in order to prevent, cure, delay, reduce the severity of, or ameliorate one or more signs or symptoms of the disorder or recurring disorder, or in order to increase time to relapse, or in order to prolong the survival of a subject beyond that expected in the absence of such treatment.

The terms "cure" and "curing," as used herein, refer to a complete remission of a disease in a subject identified using the methods of the present invention, such as, for example, a subject having an autoimmune disease, an allergic reaction, transplant rejection, or cancer, by the administration of an oxazaphosphorine, such as a lymphocytotoxic non-myeloablative amount of oxazaphosphorine (e.g., cyclophosphamide), to the subject. The remission of a disease or the elimination of symptoms of a disease in a subject may be for at least about 1 year, at least about 2 years, at least about 3 years, at least about 4 years, or at least about 5 years. In certain embodiments, a remission of a disease or an elimination of symptoms of a disease in a subject includes the absence of administering alternative methods of treatment such as immunosuppressants (e.g., cyclosporine, cyclophosphamide, etc.), and/or steroids. In some embodiments, a method of curing an immune disorder includes administration of a lymphocytotoxic non-myeloablative amount of an oxazaphosphorine drug to a subject in need thereof, where the immune disorder is not severe aplastic anemia, chronic inflammatory demyelinating polyneuropathy, paraneoplastic pemphigus, paraneoplastic pemphigus, pemphigus foliaceus, or pemphigus vulgaris.

The terms "subject," "patient," and "individual" are used interchangeably to refer to a human of any age (e.g., child, adult) and/or gender (e.g., male, female).

The terms "maximally immunosuppressive" and "maximal immunosuppression" as used herein, refer to a treatment which eliminates or reduces the mature lymphocytes of a patient but normally have little or no observable cytotoxic effect on myeloid stem cells, for example, hematopoietic progenitor stem cells. The treatment has a cytotoxic effect on the circulating mature lymphocytes (e.g., NK cells, and T and B lymphocytes) while sparing the progenitor cells, e.g., hematopoietic progenitor stem cells that are capable of reconstituting the immune system. In some embodiments, a maximally immunosuppressive agent used in the methods of the invention kills cells which express low or sensitive levels of the enzyme aldehyde dehydrogenase (e.g., NK cells and B and T lymphocytes) while sparing cells which express high or resistant levels of the enzyme aldehyde dehydrogenase (e.g., hematopoietic progenitor stem cells).

The term "incomplete immunosuppression" refers to a state of less than maximal immunosuppression. In some embodiments, incomplete immunosuppression is indicated by the existence of a WBC count of greater than zero. In some embodiments, incomplete immunosuppression is indicated by the existence of a WBC count of greater than 4. In some embodiments, incomplete immunosuppression is indicated by the existence of a WBC count of greater than 10. In some embodiments, incomplete immunosuppression is indicated by the existence of a WBC count of greater than 12. In some embodiments, incomplete immunosuppression is indicated by the existence of a WBC count of greater than 15. In some embodiments, incomplete immunosuppression is indicated by the existence of a WBC count of greater than 20.

The term "relapse" refers to the recurrence of a disorder, such as an autoimmune disease or cancer, after recovery following treatment; and or recurrence of one or more symptoms associated with a disorder after recovery following treatment. No relapse for at least about four years is intended to include no relapse between about 3.5 years to about 4.5 years. No relapse for at least about five years is intended to include no relapse between about 4.5 to about 5.5 years. No relapse for at least about ten years is intended to include no relapse between about 9 to about 11 years.

The tem, "remission" in the context of an immune disorder refers to the disappearance of autoreactive cells following treatment and/or disappearance of one or more or all symptoms associated with an adverse immune reaction, including, for example, an autoimmune disease, an allergic reaction and transplant rejection.

The term "white blood cell (WBC) count" refers to the number of white blood cells per microliter or per cubic millimeter ($mm^3$)). See, for example, Blumenreich, M. S., in Clinical Methods, The History, Physical, and Laboratory Examinations, Third Edition, 1990, Butterworth Publishers, Chapter 153, pages 724-727.

As used herein, the terms "ALDH inhibiting agent" and "ALDH inhibitor" are used interchangeably to refer to an agent that limits or inhibits the enzymatic activity of one or more aldehyde dehydrogenases. ALDH inhibiting agents can exert their effects directly or indirectly by reducing the amount of available enzyme and/or otherwise reducing the amount of ALDH enzymatic activity in one or more relevant cell populations (e.g., hematopoietic progenitor stem cells, peripheral lymphocytes, granulocytes, etc.). ALDH inhibiting agents include, but are not limited to, small molecules, proteins, polypeptides, peptides, antisense oligonucleotides, RNA interference molecules (RNAi), ribozymes, DNAzymes, aptamers, peptidomimetics, substrate mimics, decoys, dominant negative mutants, or other means for interfering with ALDH transcription and/or translation. Examples of ALDH inhibiting agents include, but are not limited to, those listed in Table 1, and any of their metabolites or analogs exhibiting ALDH-inhibiting activity. Certain anti-cancer agents (e.g., procarbazine), antibiotics (e.g., cephem antibiotics, beta-lactam antibiotics containing N-methyltetrazolethiol (NMTT)), and dietary constituents such as nutritional or dietary supplements (e.g., daidzin) have been identified as ALDH inhibiting agents.

TABLE 1

| ALDH INHIBITING AGENTS | |
| --- | --- |
| COMPOUND | COMPOUND |
| Acetaldehyde (low concentrations) | Isotretinoin (Accutane) |
| Acetaminophen | Kudzu root (*Pueraria lobata*) and Kudzu products (McGregor NR, Alcohol, 41: 469-478, 2001; U.S. Pat. No. 6,465,436 (Lukas et al.) |
| Acetazolamide | Long- and medium-chain fatty acyl derivatives of cyanamide (such as palmitoyl-, stearoyl-, and n-butyrlcyanamide) |

TABLE 1-continued

ALDH INHIBITING AGENTS

| COMPOUND | COMPOUND |
|---|---|
| Acetyloxy[(4-chlorophenyl)sulfonyl]carbamic acid | Magnesium ions (high concentrations) |
| Acrolein | Malondialdehyde (MDA) |
| Alcohol (chronic ethanol administration via its primary metabolite, acetaldehyde) | Menthol |
| Aldehyde hydrates | Menthone |
| All-trans retinoic acid | Methyltetrazolethiol |
| Amantadine | Metronidazole |
| Amperozide | Miconazole |
| Amphetamine | Mixed disulfide |
| Antidisotropic compounds (U.S. Pat. No. 7,368,434 (Keung et al.) | Moxalactam |
| Aromatic chelating agents | Mozenavir (DMP-450) |
| Aspirin | Mushrooms (*Coprinus* mushrooms including *C. atramenarius*, *C. insignis*, *C. variegates*, and *C. quadritidus*, *Beletus luridus*, *Clitocybe clavipes*, *Polyporus sulphureus*, *Pholiota squarosa*, *Morchella* spp., *Tricholoma aurantum*, and *Verpa bohemica*) |
| Beclamide | Naltrexone |
| Benomyl | N-methyltetrazolylthiomethyl-bearing beta-lactams |
| Benzoylcyanamide | N-protected alpha-aminoacyl and peptidyl derivatives of cyanimide (such as N-carbobenzoxyglycyl-, hippuryl-, N-benzoyl-L-leucyl-, N-carbobenzoxyglycyl-L-leucyl-, N-carbobenzoxy-L-pyroglutamyl-, L-pyroglutamyl-L-leucyl-, and L-pyroglutamyl-L-phenylalanylcyanamide) |
| Betazole | N(1)-alkyl, N(1)methoxy, and N(1)-hydroxy substituted ester derivatives of chlorpropamide |
| Burimamide | Nitrate-ester anti-anginal agents (e.g., isosorbite dinitrate, nitroglycerine) |
| Caffeine | Nitrefazole |
| Cadmium ions | N-tosyl-L-phenylalanine |
| Calcium carbimide | Pargyline (Eutonyl) |
| Carbamazepine | Penicillamine |
| Carbon disulfide | Pentobarbitol |
| Carbon tetrachloride | Phenobarbitol |
| Cephalosporins (e.g., methylthiotetrazole (MTT) side chain containing cephalosporins such as cefotetan, cefoperazone, cefamdole, and cefmenoxime) | Phenylethyl isothiocyanate |
| Chloral hydrate | Phorone |
| Chlorpropamide | Pimozide |
| Cimetidine | Pivaloylcyanamide |
| Clofibrate | Pravastatin |
| Copper ions | Procarbazine |
| Coprine (N5(hydroxycyclopropyl)-L-glutamine) | Progesterone |
| Cyanamide (active metabolite Nitroxyl) | Promazine |
| Daidzin (7-glucoside of 4',7-dihydroxyisoflavone; U.S. Pat. No. 5,204,369 (Vallee et al.) | Propioaldehyde |
| Daidzin analogs (U.S. Pat. Nos. 6,255,497; 6,121,010; 5,886,028; 5,624,910 (Vallee et al.) | PTEN (phosphatase and tensin homolog) |
| Diazepam | Pyrazole |
| Diethylaminobenzaldehyde | Retinoins (e.g., retinoic acid, such as all-trans retinoic acid, 9-cis retinoic acid, 13-cis retinoic acid) (Moreb JS et al., Journal of Pharmacology and Experimental Therapeutics, 312: 339-345 (2005)) |
| Diethyldithiocarbamic acid | Scopolamine |
| Diethyldithiocarbomate-methyl ester (DDTC-Me) | Sulfonylurea hypoglycemic agents (e.g., chlorpropamide, tolazamide, tolbutamide) |
| Diethyl maleate | Tamoxifen |
| Diethylstilbestrol | Testosterone |
| Di-n-propylacetate | Theophilline |
| Disulfiram (tetraethylthiuram disulfide) | Thiocarbomate herbicides |
| DOPAl | Thiram analogs (e.g., copper, mercuric, and sodium diethyldithiocarbamate; zinc and |

TABLE 1-continued

ALDH INHIBITING AGENTS

| COMPOUND | COMPOUND |
|---|---|
| | ferric dimethyldithiocarbamate; zinc and disodium ethylenebis (dithlocarbamate)) |
| Estradiol | Tolbutamide |
| Ethinyl estradiol | Trichloroethylene |
| Ethoxycyclopropanol | Vinyl ketone analogues of insect pheromones |
| Ethylphenyl(2-formylethyl)phosphinate | 1-adamantoylcyanamide |
| $Et_2N$-CS-SS-$CH_2OH$ | 1-Aminocyclopropanol |
| Fluorouracil | 1-methyltetrazole-5-thiol |
| Formazan granules | 1,1-dimethylethyl ester (NPI-2) |
| Furazolidone | 2-methyl-4-nitro-1-(4-nitrophenyl)imidazole (nitrefazole) |
| Gossypol (2,2'-(Formyl-1,6,7-trihydroxy-5-isopropyl-3-methylnaphthalene)) | 2,2'-dithiodipyridine |
| Haloperidol | 3,4-dihydroxyphenylacetaldehyde |
| Hydrocortisol | 4-amino 4-methyl 2-pentyne 1-al (AMPAL) |
| Insulin | 4-hydroxynonenal (4HNE) |
| Iron ions | 4-(N,N-dipropylamino)benzaldehyde |
| Isosorbide dinitrate | 6-cyanopurine |

Depending upon the circumstances (e.g., the type of ALDH inhibiting agent), the presence or absence of one or more ALDH inhibiting agents within a subject can be determined, for example, by questioning (e.g., interviewing) the subject, by reviewing the subject's medical file or history, or by carrying out an assay for the presence of the ALDH inhibiting agent or for a metabolite or other indicator of exposure to the ALDH inhibiting agent in a sample obtained from the subject (e.g., blood sample). For example, when interpreting a disulfiram blood level, only a small proportion of ingested disulfiram appears in the blood as the parent compound due to rapid metabolism. Metabolites of disulfiram, including diethyldithiomethylcarbamic acid and diethylthiomethylcarbamic acid, can also be measured in the plasma. (Kuffner E K et al., in Goldfrank's Toxicologic Emergencies, 7th Edition, Chapter 65, Disulfiram and Disulfiram-like Reactions, Goldfrank L R et al., eds., p. 976). Other surrogate markers of disulfiram ingestion include carbon disulfide on the breath, and diethylamine in the urine.

As used herein, the terms "ALDH activating agent", "ALDH activator", "ALDH inducing agent", and "ALDH inducer" are used interchangeably to refer to an agent that enhances or increases the enzymatic activity of one or more aldehyde dehydrogenases. ALDH activating agents can exert their effects directly or indirectly by increasing the amount of available enzyme and/or otherwise increasing ALDH enzymatic activity in one or more relevant cell populations (e.g., hematopoietic progenitor stem cells, peripheral lymphocytes, granulocytes, etc.). Examples of ALDH activating agents include, but are not limited to, those listed in Table 2, and any of their metabolites or analogs exhibiting ALDH-activating activity. Depending upon the circumstances (e.g., the type of ALDH activating agent), the presence or absence of one or more ALDH activating agents within a subject can be determined, for example, by questioning the subject, by reviewing the subject's medical file or history, or by carrying out an assay for the presence of the ALDH activating agent or for a metabolite or other indicator of exposure to the ALDH activating agent in a sample obtained from the subject (e.g., blood sample).

TABLE 2

ALDH ACTIVATING AGENTS

| COMPOUND | COMPOUND |
|---|---|
| Benzo(a)pyrene (Lin K-H et al., Cancer Research, 44: 5219-5226 (1984)) | Magnesium ions |
| Broccoli (Sreerama L et al., Clinical Cancer Research, 1: 1153-1163 (1995)) | Manganese ions |
| Calcium ions | Oltipraz |
| Catechol | PartySmart (extracts of Phoenix dactylifera, Cichorium intybus, Andrographis paniculata, Vitis vinifera, Phyllanthus amarus, and Emblica officinalis) (Venkataranganna MV et al., Indian J Med Res, 127: 460-466 (2008)) |
| Coffee (Sreerama L et al., Clinical Cancer Research, 1: 1153-1163, (1995)) | Phenobarbital (Lin K-H et al., Cancer Research, 44: 5219-5226 (1984)) |
| Cruciferae vegetable family members (Sreerama L et al., Clinical Cancer Research, 1: 1153-1163, (1995)) | TCDD (2,3,7,8-tetrachlorodibenzodioxin) (Germolec DR et al., Toxicol Appl Pharmacol, 137(1): 57-66 (1996)) |
| Liliaceae vegetable family members (Sreerama L et al., Clinical Cancer Research, 1: 1153-1163, (1995)) | 2,3-tert-butyl-4-hydroxyanisole |

The terms "ALDH modulators" and "ALDH modulatory agents" are used herein interchangeably to refer to both ALDH inhibiting agents and ALDH activating agents. ALDH modulators can be potentially any substance, molecule, element, compound, entity, or combination thereof. The term "agent" in this context includes, but is not limited to, e.g., small organic molecules; small inorganic molecules; and macromolecules such as polysaccharides, polynucleotides, polypeptides, glycoproteins, lipoproteins, and the like. An "agent" can be a natural product, synthetic compound, semi-synthetic compound, or a chemical compound, or a combination of two or more substances. In some instances, an oxazaphosphorine or its metabolite may act as an auto-inducer or auto-inhibitor of ALDH. In some embodiments, the ALDH modulator is a non-oxazaphosphorine and/or not a metabolite of an oxazaphosphorine.

Within the context of determining the presence or absence of one or more ALDH modulators, and determining whether the subject has otherwise been exposed to one or more ALDH modulators, the term "determining" refers to quantitative or qualitative determinations and, as such, the term "determining" is used interchangeably herein with "assaying," "measuring," and the like. Depending upon the circumstances (e.g., the type of ALDH modulator, the availability of an assay for the ALDH modulator or its surrogate, the reliability of the subject's response, etc.), the presence or absence of one or more ALDH modulators within a subject can be determined, for example, by questioning the subject, by reviewing the subject's medical file or history, or by carrying out an assay for the presence of the ALDH modulator or for a metabolite or other indicator of exposure to the ALDH modulator in a sample obtained from the subject (e.g., blood sample). The time frame for which the presence, use, or exposure of an ALDH modulator or surrogate is relevant will depend upon the particular type of ALDH modulator. For example, hormonal contraception can exert its ALDH inhibitory effect for a significant period of time after being taken.

One or more questions can be presented to the subject regarding ALDH modulator exposure, such as: verbal, written (e.g., as a questionnaire), telephone survey, fax survey, Internet questionnaire to be submitted via the Internet, or computer display and interface through which the subject directly inputs his/her responses to the questions. Thus, the determining step can be computer-implemented. For example, presenting the subject with one or more questions can involve providing the one or more questions from a server to a client over a computer network. In some embodiments, presenting the one or more subjects with questions comprises presenting the one or more subjects with a questionnaire on a display on a computer, such as a hand-held computer, laptop computer, or desktop computer. In some embodiments, presenting the one or more subjects with a questionnaire comprises presenting the one or more patients with the questionnaire over the Internet.

Any method that can distinguish the presence of the ALDH modulator (or surrogate marker of the ALDH modulator, such as a metabolite of the modulator) in a subject or in a sample obtained from the subject can be used. Such methods include, without limitation, immunological assays that use a binding agent (e.g., antibody, antibody fragment, receptor, ligand, etc.) to detect the ALDH modulator, or surrogate marker thereof. Such binding agents include, without limitation, antibodies or antibody fragments having specificity for the ALDH modulator or surrogate marker.

Assays can include suitable positive and/or negative controls. A variety of other reagents may be included in the assay, such as salts, neutral proteins, e.g., albumin, detergents, etc., including agents used to facilitate optimal enzyme activity and/or reduce non-specific or background activity. Reagents that improve the efficiency of the assay, such as protease inhibitors, nuclease inhibitors, anti-microbial agents, etc., may be used. Screening assays may be designed a number of different ways, where a variety of assay configurations and protocols may be employed. For example, a binding agent or other component may be bound to a solid support, and the remaining components contacted with the support bound component. For example, an anti-modulator or anti-surrogate antibody or antibody fragment can be immobilized to a solid support, a sample can be applied to the immobilized antibody/fragment such that any free modulator/surrogate is captured, and a second labeled anti-modulator antibody/fragment can be used to detect any captured modulator/surrogate. In these types of immunological assays, a simple color reaction can be used, for example.

A "reduced dose" refers to a dose that is below the normally administered dose, below the standard therapeutic dose, and/or below the recommended dose. In some embodiments, these latter terms are used interchangeably herein as a reference point, to refer to the dose that is, at the time of application of the pharmacologic agent (e.g., oxazaphosphorine, such as cyclophosphamide), recommended for use in a given setting by authoritative sources in the pharmaceutical community, including the Physician's Desk Reference, $62^{nd}$ Edition (2008), package inserts of the drug product, and/or the Food and Drug Administration. For example, if the normally administered dose is 50 milligrams per kilogram of the subject's body weight per day (50 mg/kg/day) for a particular setting, a reduced dose is less than 50 mg/kg/day. In one embodiment, the reduced dose is equal to about 75% or less of the normally administered dose. In another embodiment, the reduced dose is equal to about 50% or less of the normally administered dose. In another embodiment, the reduced dose is equal to about 33% or less of the normally administered dose.

An "increased dose" refers to a dose that is above the normally administered dose, above the standard therapeutic dose, and/or above the recommended dose. In some embodiments, these latter terms are used interchangeably herein as a reference point, to refer to the dose that is, at the time of application of the pharmacologic agent (e.g., oxazaphosphorine, such as cyclophosphamide), recommended for use in a given setting by authoritative sources in the pharmaceutical community, including the Physician's Desk Reference, $62^{nd}$ Edition (2008), package inserts of the drug product, and the Food and Drug Administration. For example, if the normally administered dose is 50 milligrams per kilogram of the subject's body weight per day (50 mg/kg/day) for a particular setting, an increased dose is greater than 50 mg/kg/day. In one embodiment, the increased dose is equal to or greater than about 175% of the normally administered dose. In another embodiment, the increased dose is equal to or greater than about 150% of the normally administered dose. In another embodiment, the increased dose is equal to or greater than about 133% of the normally administered dose.

The term "sample" refers to a biological sample potentially containing the cells and/or analyte of interest, such as a biologic fluid (e.g., blood, saliva), bone marrow or other tissue, breath, etc. (Wierzchowski J et al., *Anal Biochem*, 1997, 245(1):69-78).

The terms "computer-readable storage medium" and "computerized storage medium" are used herein interchangeably to refer to a storage medium that can hold patient information and/or computer executable instructions for carrying out a method or system of the invention (e.g., a method for treating a subject in need thereof with an oxazaphosphorine; a method for selecting a subject suitable for oxazaphosphorine therapy; a system for ensuring the safety or efficacy of a treatment that includes oxazaphosphorine administration; a method for delivering an oxazaphosphorine to subjects in need thereof while restricting access to the oxazaphosphorine by subjects for whom the drug may be contraindicated; and/or a method of providing a system of care for an oxazaphosphorine drug regimen). Preferably, a computer-readable storage medium of the invention can store documents from which information can be mined. Alternatively, or additionally, the medium comprises a processor connectable to a network through which access is obtained to one or more collections of documents (collectively, a data source). Preferably, a processor of the system comprises a central processing unit (CPU), which executes one or more programs embedded in the computer readable storage medium to execute the methods and systems described herein. Computer readable storage media include but are not limited to: hard disks (hard drives), floppy disks, compact disks, DVDs, flash memory, tape, online internet web site, intranet web site; other types of optical, magnetic, or digital, volatile or non-volatile storage medium that can contain a program code comprising a set of instructions.

The computer-readable storage medium of the invention participates in, directly or indirectly, providing signals, instructions and/or data. The computer-readable storage medium may take forms, including, but not limited to, non-volatile media, volatile media, and transmission media. Non-volatile media may include, for example, optical or magnetic disks and so on. Volatile media may include, for example, optical or magnetic disks, dynamic memory and the like. Transmission media may include coaxial cables, copper wire, fiber optic cables, and the like. Transmission media can also take the form of electromagnetic radiation, like those generated during radio-wave and infra-red data communications, or take the form of one or more groups of signals. Common forms of a computer-readable storage medium include, but are not limited to, an application specific integrated circuit (ASIC), a compact disc (CD), a digital video disk (DVD), a random access memory (RAM), a read only memory (ROM), a programmable read only memory (PROM), an electronically erasable programmable read only memory (EEPROM), a disk, a carrier wave, a memory stick, a floppy disk, a flexible disk, a hard disk, a magnetic tape, other magnetic media, a CD-ROM, other optical media, punch cards, paper tape, other physical media with patterns of holes, an EPROM, a FLASH-EPROM, or other memory chip or card, and other media from which a computer, a processor or other electronic device can read. Signals used to propagate instructions or other software over a network, like the Internet, can be considered a "computer-readable storage medium." The computer-readable storage medium can comprise cooperating or interconnected computer readable media, which exist exclusively on a single computer system or are distributed among multiple interconnected computer systems that may be local or remote. A computer can include a stand-alone unit or several interconnected units. A functional unit is considered an entity of hardware or software, or both, capable of accomplishing a specified purpose. Hardware includes all or part of the physical components of an information processing system, such as computers and peripheral devices.

The term "computer-implemented" refers to a method or system in which one or more steps of the method or system are carried out by a computer or by using a computer such that the one or more steps are computer-implemented operations. For example, one or more steps of the method or system can exist as instructions embodied on computer readable storage media, e.g., software or hardware. A computer-implemented system or method may incorporate components for interfacing with a user. The computer-implemented method or system can employ a user viewable display for viewing an output of computer-implemented instructions or results of patient tests, user input devices (e.g., keyboards or pointing devices such as a mouse) or other peripheral devices for inputting user commands, activating the method or system, or outputting data in a tangible form (e.g., printer or other method to generate a prescription authorization code). Computer program instructions may be loaded onto a computer or other programmable data processing apparatus to cause a series of operational steps to be performed on the computer or other programmable apparatus to produce a computer-implemented method or system such that the instructions which execute on the computer or other programmable apparatus provide steps for implementing the functions specified in the system or method.

The terms "idiotype," "Id," and "idiotypic determinant," as used herein, refer to an epitope in the hypervariable region of an immunoglobulin. Typically, an idiotype or an epitope thereof is formed by the association of the hypervariable or complementarity determining regions (CDRs) of VH and VL domains.

The terms "anti-idiotypic" and "anti-Id," refer to the binding of an antibody or antigen-binding portion thereof to one or more idiotypes.

The term "autologous anti-idiotypic vaccine" refers to a composition, the active ingredient of which is an immunogenic molecule capable of inducing an immune response against a B-cell idiotype derived from the same subject to which it is administered. In some embodiments, the immunogenic molecule in a vaccine used in the methods of the present invention is a normal product of a subject's B cells that happens to be expressed clonally on the cancer cells (e.g., cells derived from a Hodgkin's lymphoma or non-Hodgkin's lymphoma or chronic lymphocytic leukemia, mantle cell lymphoma or multiple myeloma) and serves as a unique a target for immune attack. In some embodiments, an "autologous anti-idiotypic vaccine," is capable of eliciting an immune response against a B-cell idiotype derived from a subject having non-Hodgkin's lymphoma. In another embodiment, an "autologous anti-idiotypic vaccine," is capable of eliciting an immune response against a B-cell idiotype derived from a subject having Hodgkin's lymphoma. In yet another embodiment, an "autologous anti-idiotypic vaccine," is capable of eliciting an immune response against a B-cell idiotype derived from a subject having chronic lymphocytic leukemia. In a further embodiment, an "autologous anti-idiotypic vaccine," is capable of eliciting an immune response against a B-cell idiotype derived from a subject having multiple myeloma. In a yet further embodiment, an "autologous anti-idiotypic vaccine," is capable of eliciting an immune response against a B-cell idiotype derived from a subject having mantle cell lymphoma. In some embodiments of the present invention, an "autologous anti-idiotypic vaccine," is used for the treatment of a B-cell derived cancer in combination with a lymphocytotoxic but hematopoietic cell sparing high-dose pulsed amount of an oxazaphosphorine drug. In other embodiments of the present invention, an "autologous anti-idiotypic vaccine" is used for the treatment of a B-cell derived cancer in combination with other immune therapeutics such as, for example, monoclonal antibodies that selectively bind B-cell specific antigens. In some embodiments, an "autologous anti-idiotypic vaccine" includes an antigen associated with a B-cell derived cancer in a subject (e.g., non-Hodgkin's lymphoma, Hodgkin's lymphoma, chronic lymphocytic leukemia, mantle cell lymphoma or multiple myeloma) linked to KLH (keyhole limpet hemocyanin, a carrier protein). In some embodiments of the present invention, an autologous anti-idiotypic vaccine is administered with GM-CSF.

Methods of Treatment

In some aspects, the present invention provides methods for treating a subject in need thereof with an oxazaphosphorine drug. In some embodiments, the methods of the present invention include determining whether treatment with an oxazaphosphorine can be safe and effective for the subject based on one or more safety or efficacy factors; and treating the subject with the oxazaphosphorine if it is determined that treatment with oxazaphosphorine can be safe and effective.

As used herein, the term "safety or efficacy factors" refer to features or causes which make oxazaphosphorine treatment more safe or effective. In some embodiments, the safety or efficacy factors include an ALDH inhibition factor or ALDH activation factor. ALDH inhibition factors include, but are not limited to, hormonal contraceptive use (e.g., estrogen and/or progestin via oral administration, patch or injection), tobacco use, and chronic alcohol use. ALDH inhibition factors also include, but are not limited to the use of ALDH inhibiting agents, such as those listed in Table 1. ALDH activation factors include, but are not limited to, the use of ALDH activating agents, such as those listed in Table 2.

The ALDH inhibiting agent can be any of the ALDH inhibiting agents listed herein, including, but not limited to, disulfiram, calcium carbimide, diazepam, chlordiazepoxide, isosorbide dinitrate, nitroglycerine, chlorpropamide, tolazamide, and cephalosporin. The ALDH activating agent can be any of the ALDH activating agents listed herein, including calcium ions.

In some embodiments, the safety or efficacy factors include an ALDH level consistent with a resistant ALDH level in hematopoietic progenitor stem cells. In some embodiments, the safety or efficacy factors include an ALDH level consistent with a resistant ALDH level in peripheral lymphocytes.

In some embodiments, the method further includes periodically determining whether treatment with an oxazaphosphorine continues to be safe and effective for the subject based on one or more safety or efficacy factors. In some embodiments, the method further includes monitoring white blood cell count before treatment, during treatment, after treatment, or a combination of two or more of the foregoing.

In some embodiments, treating the subject includes adjusting dosage and/or dosage schedule, or recommencing treatment, based on the white blood cell count. In some embodiments, treating includes adjusting dosage and/or dosage schedule, or recommencing treatment, based on the white blood cell count based on an ALDH level in a sample comprising hematopoietic progenitor stem cells, or based on an ALDH level in a sample comprising peripheral lymphocytes, or both.

In some embodiments, the methods of the present invention include treating the subject with an oxazaphosphorine; and providing the subject with information or advising the subject that the subject should not use hormonal contraceptives, tobacco or alcohol during treatment.

In those embodiments in which an oxazaphosphorine (e.g., cyclophosphamide) is to be administered, the oxazaphosphorine may be administered as a monotherapy or as a combination therapy (in combination with other agents concurrently or sequentially).

In some embodiments, the method further includes advising the subject to discontinue use of hormonal contraception prior to treatment. In some embodiments, the method further includes advising the subject to discontinue use of hormonal contraception at least 60 days prior to treatment, at least 80 days prior to treatment, at least 100 days prior to treatment, at least 120 days prior to treatment, at least 140 days prior to treatment, at least 160 days prior to treatment, or at least 180 days prior to treatment.

In some embodiments, the method further includes advising the subject to use non-hormonal contraception during treatment. In some embodiments, the method further includes advising the subject to use non-hormonal contraception subsequent to treatment. In some embodiments, the method further includes advising the subject to use non-hormonal contraception for at least 30 days subsequent to treatment, at least 60 days subsequent to treatment, at least 90 days subsequent to treatment, at least 120 days subsequent to treatment, or at least 180 days subsequent to treatment.

In some embodiments, the methods of the present invention include obtaining subject information relating to the existence of one or more contraindication factors; determining whether oxazaphosphorine treatment is contraindicated based on the information relating to one or more contraindication factors; and administering oxazaphosphorine only if oxazaphosphorine treatment is not contraindicated.

In some embodiments, the contraindication factors include one or more ALDH inhibition factors. ALDH inhibition factors include, but are not limited to, hormonal contraceptive use (e.g., estrogen and/or progestin via oral administration, patch or injection), tobacco use, and chronic alcohol use. ALDH inhibition factors also include, but are not limited to the use of ALDH inhibiting agents and/or ALDH activating agent.

The ALDH inhibiting agent can be any of the ALDH inhibiting agents listed herein, including, but not limited to, disulfiram, calcium carbimide, diazepam, chlordiazepoxide, isosorbide dinitrate, nitroglycerine, chlorpropamide, tolazamide, and cephalosporin. The ALDH activating agent can be any of the ALDH activating agents listed herein, including calcium ions.

In some embodiments, the method further includes counseling the patient as to risk avoidance measures in response to the information relating to the existence of one or more contraindication factors.

In some embodiments, the methods of the present invention include obtaining information relevant to a sensitivity factor of a subject selected from the group consisting of: white blood cell count, ALDH in lymphocytes or ALDH in hematopoietic progenitor stem cells and combinations thereof; determining a safe and effective dose of an oxazaphosphorine informed by one or more of the sensitivity factors; and administering the safe and effective dose of the oxazaphosphorine to the subject.

In some embodiments, the methods of the present invention further include administering an ALDH inhibiting agent or an ALDH activating agent. For example, in some embodiments, the methods of the present invention further include administering an ALDH inhibiting agent or an ALDH activating agent before, during or after determining the safe and effective dose of an oxazaphosphorine. In some embodiments, the methods of the present invention further include administering an ALDH inhibiting agent or an ALDH activating agent before administering the safe and effective dose of an oxazaphosphorine. The ALDH inhibiting agents and ALDH activating agents can be any of those described herein. In some embodiments, the ALDH inhibiting agent includes disulfiram.

In some embodiments, the information relevant to a sensitivity factor of a subject is obtained before a treatment is commenced or recommenced. In some embodiments, the information relevant to a sensitivity factor of a subject is obtained during treatment and the safe and effective dose is adjusted based on the information during treatment.

The oxazaphosphorine utilized in the methods of the present invention may be any of those known to one of skill in the art or described herein. For example, the oxazaphosphorine utilized in the methods of the present invention includes, but is not limited to cyclophosphamide, ifosfamide, perfosfamide, trophosphamide, and a pharmaceutically acceptable salt, solvate, prodrug, or active metabolite thereof. In some embodiments, the oxazaphosphorine is cyclophosphamide, or a pharmaceutically acceptable salt, solvate, prodrug, or active metabolite thereof. Active metabolites of oxazaphosphorine drugs include, but are not limited to 4-hydroxycyclophosphamide or aldophosphsamide.

In some embodiments, treating the subject includes administering a non-myeloablative amount of oxazaphosphorine. In some embodiments, treating the subject includes administering a myeloablative amount of oxazaphosphorine. A myeloablative dose may be desired, for example, when used in conjunction with stem cell transplantation.

In some embodiments, the present invention includes high-dose oxazaphosphorine therapy. In some embodiments, high-dose oxazaphosphorine therapy will be more effective than the low-dose therapy, which usually requires daily oral dosing or monthly intravenous pulses at 500-1000 mg/m$^2$ and has a higher risk of malignancies and premature menopause and/or infertility. High-dose oxazaphosphorine therapy, however, is not suitable for all patients, because of higher toxicity. Accordingly, in some embodiments, the present invention includes low-dose oxazaphosphorine therapy.

In some embodiments, the subject is a female of childbearing potential. As with other alkylating agents, teratogenic effects have been reported in association with the use of cyclophosphamide. In general, alkylating agents when given during the first trimester are believed to cause slight increases in the risk of congenital malformations, and when given during the second or third trimesters are believed to increase the risk of growth retardation (Glantz, 1994). (Cunningham et al, 1993; Doll et al, 1988). Cyclophosphamide crosses the placenta and belongs to the U.S. Food and Drug Administration's Pregnancy Category: Category D (Prod Info Cytoxan®, 2000) (All Trimesters). Accordingly, in some embodiments, treatment in accordance with the present invention will include the use of a non-hormonal means of contraception (e.g., abstinence or condoms), but not a hormonal contraceptive.

Granulocytopenia

Granulocytes, also called polymorphonuclear leukocytes (PMN or PML), are white blood cells that are characterised by the presence of granules in their cytoplasm. The three types of granulocytes (neutrophil granulocytes, eosinophil granulocytes and basophil granulocytes) are distinguished by their appearance under Wright's stain. Granulocytopenia, an abnormally low concentration of granulocytes in the blood, reduces resistance to infection, and thus is typically an unwanted and dangerous complication of oxazaphosphorine use. In some aspects of the present invention, the method includes monitoring or determining ALDH levels or activity in granulocytes. In some embodiments, where a subject has low ALDH levels or activity in granulocytes or other white blood cells, the dosage of oxazaphosphorine is lowered or the treatment with oxazaphosphorine is halted. However, in some cases, e.g., in cases where maximal immunosuppression is desired, targeting of ALDH in the granulocytes is desired. Accordingly, in some embodiments, the dosage of oxazaphosphorine is adjusted based upon the level or activity of ALDH in the granulocytes.

In some aspects, the invention is directed to methods for treating a subject in need thereof with a cytotoxic agent, the method comprising: (a) obtaining an ALDH level in a sample of granulocytes obtained from the subject; and (b) administering: (i) an oxazaphosphorine (e.g., low dose oxazaphosphorine) to the subject if the obtained ALDH level is consistent with a resistant ALDH level in granulocytes, or (ii) a reduced dose of the oxazaphosphorine to the subject if the obtained. ALDH level is consistent with a sensitive ALDH level in granulocytes, or (iii) a non-oxazaphosphorine cytotoxic agent to the subject if the obtained ALDH level is consistent with a sensitive ALDH level in granulocytes. In some embodiments, the cytotoxic agent is being administered to the subject for treatment of cancer. In some embodiments, the non-oxazaphosphorine cytotoxic agent is an alkylating agent, or an antimetabolite such as azathioprine (Imuran). In some embodiments, the method further comprises, prior to (b), determining the presence or absence of an ALDH inhibiting agent in the subject, or determining whether the subject has otherwise been exposed to an ALDH inhibiting agent.

In some aspects, the present invention is directed to a method for treating a subject in need thereof with a cytotoxic agent, the method comprising: (a) determining the presence or absence of an ALDH inhibiting agent in the subject, or determining whether the subject has otherwise been exposed to an ALDH inhibiting agent; and (b) administering: (i) an oxazaphosphorine (e.g., low dose oxazaphosphorine) to the subject if an ALDH inhibiting agent is not present in the subject or if the subject has not otherwise been exposed to an ALDH inhibiting agent, or (ii) a reduced dose of the oxazaphosphorine to the subject if an ALDH inhibiting agent is present in the subject or if the subject has otherwise been exposed to an ALDH inhibiting agent, or (iii) a non-oxazaphosphorine cytotoxic agent to the subject if an ALDH inhibiting agent is present in the subject or if the subject has otherwise been exposed to an ALDH inhibiting agent. In some embodiments, the cytotoxic agent is being administered for treatment of cancer. Exemplary cancers include malignant lymphomas, Hodgkin's disease, lymphocytic lymphoma, mixed-cell lymphoma, histiocytic lymphoma, Burkitt's lymphoma; multiple myeloma, leukemias, neuroblastoma, adenocarcinoma of the ovary, retinoblastoma, and carcinoma of the breast. In some embodiments, the reduced dose of (b)(ii) is less than that which would otherwise be administered for treatment of a cancer from which the subject is suffering. In some embodiments, the non-oxazaphosphorine cytotoxic agent is an alkylating agent, or an antimetabolite such as azathioprine (Imuran). In some embodiments, the method further comprises obtaining an ALDH level in a sample of granulocytes obtained from the subject prior to (b).

In some aspects, the present invention provides method for treating a subject having a neurological immune disorder. In some embodiments, the method includes administering a lymphocytoxic non-myeloablative amount of a oxazaphosphorine drug to the subject, such that the subject's immune system reconstitutes without stem cell transplantation, and wherein the subject has substantial disability observable or equivalent to an Expanded Disability Status Scale (EDSS) score of between about 2 and about 6.5 at time of treatment.

Neurological immune disorders include any disorders of the immune system that effect the central nervous system (brain and spinal cord), the peripheral nervous system, or the autonomic nervous system. In some embodiments, the neurological immune disorder includes demyelinating diseases of the central nervous system (such as multiple sclerosis) and of the peripheral nervous system (such as Guillain-Barré syndrome and chronic inflammatory demyelinating polyneuropathy (CIDP)). In some embodiments, the neurological immune disorder is chronic inflammatory demyelinating polyneuropathy. In some embodiments, the neurological immune disorder is not chronic inflammatory demyelinating polyneuropathy. In some embodiments, the disorder is an autoimmune disorder.

In some embodiments, the disorder is multiple sclerosis (MS). In some embodiments the disorder is relapsing remitting MS (RRMS), secondary progressive MS (SPMS), progressive relapsing MS (PRMS), or primary progressive MS (PPMS). In some embodiments, the disorder is RRMS. For example in some embodiments, the disorder is RRMS in accordance with McDonald criteria. RRMS is typically characterized by unpredictable attacks (relapses) followed by periods (e.g., periods of months to years) of relative quiet (remission) with no new signs of disease activity. Deficits suffered during the attacks may either resolve or may be permanent. MS has a broad range of symptoms. Physicians take detailed histories and perform complete physical and neurological examinations. Magnetic resonance imaging (MRI) scans with intravenously administered contrast agents (e.g., gadolinium) can assist in identifying, describing, and in some instances, dating lesions in the brain (plaques). An electro-physiological test can be used to examine impulses traveling through the nerves to determine if the impulses are moving normally or too slowly. Examining the cerebro-spinal fluid that surrounds the brain and spinal cord may identify abnormal antibodies or cells associated with the presence of MS.

Signs and symptoms of MS include, but are not limited to, changes in sensation (hypoesthesia and paresthesia), muscle weakness, muscle spasms, or difficulty in moving; difficulties with coordination and balance (ataxia); problems in speech (dysarthria) or swallowing (dysphagia), visual problems (nystagmus, optic neuritis, or diplopia), fatigue, acute or chronic pain, and bladder and bowel difficulties. Cognitive impairment of varying degrees and emotional symptoms of depression or unstable mood are also common. Uhthoff's phenomenon, an exacerbation of symptoms due to an exposure to higher than usual ambient temperatures, and Lhermitte's sign, an electrical sensation that runs down the back when bending the neck, are particularly characteristic of MS although not specific. The main clinical measure of disability progression and symptom severity is the Expanded Disability Status Scale (EDSS).

In some embodiments, the disorder is aggressive RRMS. In some embodiments, the subject has had one or more relapses within the 12 months preceding the oxazaphosphorine treatment. In some embodiments, the subject has one or more total gadolinium enhancing lesions on a brain and/or spinal cord magnetic resonance imaging (MRI), or one or more large enhancing lesions measuring at least about 1 centimeter, within about 18 months prior to the oxazaphosphorine treatment. In some embodiments, the subject has one or more total gadolinium enhancing lesions on a brain and/or spinal cord magnetic resonance imaging (MRI), or one or more large enhancing lesions measuring at least about 1 centimeter, within about one year prior to the oxazaphosphorine treatment. In some embodiments, the subject has sustained increase of equal to or greater than about 1.0 on the EDSS, e.g., an increase for a time period equal to or greater than about 3 months.

In some embodiments, the subject has substantial disability observable or equivalent to an EDSS score of between about 2 and about 6.0 at time of the oxazaphosphorine treatment.

In some embodiments, the subject has undergone conventional immunomodulatory treatment for the neurological immune disorder. In some embodiments, the subject has undergone conventional immunomodulatory treatment for the neurological immune disorder and has experienced clinical progression despite the conventional treatment.

In some embodiments, the subject exhibits sustained improvement in disability following the oxazaphosphorine treatment. In some embodiments, the sustained improvement comprises improvement that is observable or equivalent to a change in EDSS score of equal to or greater than a 1 point decrease for at least two consecutive assessments. In some embodiments, the disorder remains in remission without administration of additional immunosuppressive agents.

In some embodiments, the method further comprises identifying the subject as suffering from the neurological immune disorder.

In some embodiments, oxazaphosphorine therapy is designed to eradicate the immune system. Accordingly, subjects may undergo a time of immune deficiency, e.g., deficiency which is most severe during the first three months post treatment with oxazaphosphorine. In some embodiments, any one of the methods of the present invention may further include monitoring viral titers subsequent to oxazaphosphorine administration. Methods for monitoring viral titers are discussed in more detail below. In some embodiments, any one of the methods of the present invention may further include monitoring viral titers for at least about 15 days subsequent to oxazaphosphorine administration. In some embodiments, any one of the methods of the present invention may further include monitoring viral titers for at least about a month subsequent to oxazaphosphorine administration. In some embodiments, any one of the methods of the present invention may further include monitoring viral titers for at least about 2 months subsequent to oxazaphosphorine administration. In some embodiments, any one of the methods of the present invention may further include monitoring viral titers for at least about 3, 4, 5, 6, 7, 8 or 9 months subsequent to oxazaphosphorine administration. In some embodiments, evidence of improving and apparently adequate return of immune function will occur between about 6 and 9 months after treatment.

In some embodiments, any one of the methods of the present invention may further include advising a subject to stay in an area local to the treating hospital for a time period subsequent to discharge, e.g., at least about 10, 20, 30, 40, 50 or 60 days subsequent to discharge. In some embodiments, any one of the methods of the present invention may further include advising a subject to wear a surgical mask when indoors (e.g., in hospitals, doctor's offices, and when around non-family persons) a time period subsequent to treatment, e.g., at least about 1, 2, 3, 4, or 5 months post-treatment.

In some embodiments, any one of the methods of the present invention may further include advising a subject to receive antiviral therapy subsequent to treatment with oxazaphosphorine. In some embodiments, any one of the methods of the present invention may further include treating a patient with an antiviral, e.g., therapeutically and/or prophylactically. In some embodiments, the antiviral targets varicella, zoster or interstitial pneumonia or any combination thereof. In some embodiments, the antiviral is valacyclovir. In some embodiments, the antiviral is varicella zoster immune globulin (VZIG) prophylaxis.

Dosage and Dosage Selection

In some aspects, the present invention provides methods for determining a safe and effective dose of an oxazaphosphorine for treatment of a subject in need thereof. In some embodiments, the methods include obtaining information relevant to a sensitivity factor of a subject selected from the group consisting of: white blood cell count, ALDH in lymphocytes, ALDH in hematopoietic progenitor stem cells or any combinations thereof; and determining safe and effective dose of an oxazaphosphorine informed by one or more of the sensitivity factors.

In some embodiments, the information to a sensitivity factor of a subject is obtained before a treatment is commenced or recommenced. In some embodiments, the information to a sensitivity factor of a subject is obtained during treatment and the safe and effective dose is adjusted based on the information during treatment.

Without wishing to be bound by any particular theory, it is believed that safe and effective high-dose oxazaphosphorine treatment depends on both the ability of hematopoietic progenitor stem cells to resist high-dose oxazaphosphorine as a result of their elevated ALDH and on a sufficiently weak or absent ALDH level in peripheral lymphocytes which renders those cells sensitive to treatment. Moreover, it is believed that safe and effective low-dose oxazaphosphorine treatment depends on a dosage that effectively targets tumor cells while not being high enough to overcome ALDH levels in peripheral lymphocytes (which would effect the immune system).

In some embodiments, a sample including hematopoietic progenitor stem cells, for example, a bone marrow aspirate, can be derived from a subject and exposed to increasing amounts of oxazaphosphorine (e.g., cyclophosphamide). A dose of oxazaphosphorine such as cyclophosphamide can be identified as being suitable for administration to the subject, if hematopoietic progenitor stem cells survive when exposed to the dose, however, are killed when exposed to a dose higher than the dose at which they survive. Accordingly, such a dose is identified as an effective dose for the particular subject.

In some embodiments, a sample including peripheral lymphocytes (e.g., CD4-positive peripheral lymphocytes), for example, a banked blood sample, can be derived from a subject and exposed to increasing amounts of oxazaphosphorine such as cyclophosphamide. A dose of oxazaphosphorine can be identified as being suitable for administration to the subject, if the peripheral lymphocytes are killed when exposed to a dose higher than the dose at which they survive. Another exemplary dose is a dose within a concentration between which a hematopoietic cell population isolated in a sample survives the treatment and the minimal dose required to kill all or a substantial fraction of the peripheral lymphocytes in a banked blood sample.

In some embodiments, a sample including peripheral lymphocytes, for example, a banked blood sample, can be derived from a subject and exposed to increasing amounts of oxazaphosphorine such as cyclophosphamide. A dose of oxazaphosphorine can be identified as being suitable for administration to the subject, if the dose is within a previously determined range deemed sufficient to drive the subject's white blood cell count to 0 following administration of the therapy. This determination could for instance come from a sampling of the lymphocytes of a similar patient population as the subject or from family members of the subject or from a previous sampling from the subject, or from a model or proxy of the metabolism of the drug by the aldehyde dehydrogenase in the subject.

Accordingly, a dose is identified as an effective dose for a particular subject. The various compounds (e.g., oxazaphosphorines and non-oxazaphosphorine cytotoxic agents) used in the methods described herein may be administered orally, parenterally (e.g., intravenously), intramuscularly, sublingually, buccally, rectally, intranasally, intrabronchially, intrapulmonarily, intraperitonealy, topically, transdermally and subcutaneously, for example. The amount of compound administered in a single dose may be dependent on the subject being treated, the subject's weight, the manner of administration and the judgment of the prescribing physician. Generally, however, administration and dosage and the duration of time for which a composition is administered will approximate that which are necessary to achieve a desired result. In some embodiments, the oxazophosphorine (e.g., cyclophosphamide) may be in a lyophilized form and combined with a diluent (e.g., sterile water and/or sterile sodium chloride solution) prior to administration.

In some embodiments, treating the subject includes intravenous administration the oxazaphosphorine drug. In some embodiments, treating the subject includes intravenous administration of between about 25 mg/kg to about 75 mg/kg oxazaphosphorine in divided doses over a period of from about 1 to about 7 days, e.g., between about 30 mg/kg to about 60 mg/kg in divided doses over a period of from about 2 to about 6 days, e.g., between about 40 mg/kg to about 50 mg/kg in divided doses over a period of from about 2 to about 5 days. In some embodiments, treating the subject includes intravenous administration of about 5 mg/kg to about 20 mg/kg oxazaphosphorine every 5 to 12 days, e.g., about 10 mg/kg to about 15 mg/kg every 7 to 10 days. In some embodiments, treating the subject includes intravenous administration of about 1 to about 10 mg/kg of oxazaphosphorine once or twice weekly, e.g., about 3 to about 5 mg/kg twice weekly. In some embodiments, treating the subject includes intravenous administration of about 10 mg/kg to about 250 mg/kg of oxazaphosphorine for 1 to 14 days, e.g., 50 mg/kg to about 250 mg/kg for 1 to 10 days. In some embodiments, treating the subject includes intravenous administration of about 100 mg/kg to about 200 mg/kg of oxazaphosphorine for 1 to 7 days. In some embodiments, treating the subject includes intravenous administration of about 25 mg/kg to about 100 mg/kg of oxazaphosphorine for 2 to 6 days. In some embodiments, treating the subject includes intravenous administration of about 25 mg/kg to about 100 mg/kg of oxazaphosphorine for 3 to 5 days. In some embodiments, treating the subject includes intravenous administration of about 50 mg/kg/day of oxazaphosphorine, e.g., about 50 mg/kg/day of oxazaphosphorine, for 4 consecutive days.

In some embodiments, treating the subject includes oral administration of the oxazaphosphorine drug. In some embodiments, treating the subject includes oral administration of about 1 mg/kg to about 5 mg/kg daily for about 30 to about 120 days, e.g., about 2 mg/kg to about 4 mg/kg daily for about 45 to about 105 days, e.g., about 2.5 mg/kg to about 3 mg/kg daily for about 60 to about 90 days.

In some embodiments, the method of treatment further includes administration of mesna, an adjuvant used in cancer chemotherapy, by any suitable route (e.g., oral, intravenous). Without wishing to be bound by any particular theory, it is believed that mesna may reduce the incidence of haemorrhagic cystitis and hematuria in oxazaphosphorine therapy by neutralizing metabolites of oxazaphosphorines such as acrolein. In some embodiments, mesna is administered at a total daily dosage of between about 10 mg/kg and about 100 mg/kg. In some embodiments, mesna is administered at a total daily dosage of about 10 mg/kg, 20 mg/kg, 30 mg/kg, 40 mg/kg, 50 mg/kg, 60 mg/kg, 70 mg/kg, 80 mg/kg, 90 mg/kg, or 100 mg/kg. In some embodiments, mesna is administered in a bolus dosage. In some embodiments, mesna is administered in a series of dosages. It is understood that, in such series of dosages, each individual dosage may be the same or different than each other individual dosage. Moreover, the time span between each dosage may be the same or different than the time span between any two other dosages. For example, in one embodiment, mesna is administered in a 10 mg/kg dosage prior to oxazaphosphorine administration, followed by 10 mg/kg dosages at 3, 6, and 8 hours after the oxazaphosphorine administration, such that the total daily dose is 40 mg/kg. For example, over the four days, for a 70 kg patient, the total dose of mesna could be about 11.2 grams.

In some embodiments, the methods include (a) measuring ALDH in a sample including hematopoietic progenitor stem cells derived from the subject; and (b) determining an effective dose of oxazaphosphorine based on comparison of ALDH to an appropriate standard. In some embodiments, the methods include (a) measuring ALDH in a sample including peripheral lymphocytes derived from the subject; and (b) determining an effective dose of oxazaphosphorine based on comparison of ALDH to an appropriate standard. In some embodiments, the methods include (a) measuring ALDH in a sample including peripheral lymphocytes derived from the subject; (b) measuring ALDH in a sample including hematopoietic progenitor stem cells derived from the subject; and (c) determining an effective dose of oxazaphosphorine based on comparison of both ALDH measurements to corresponding appropriate standards.

As indicated above, patients who achieved maximal immunosuppression following the therapy as indicated by their WBC count reaching 0 experience a better clinical outcome and lessened risk of disease relapse than patients whose WBC count did not reach zero following therapy. Therefore, in another aspect, the present invention provides a method for identifying a subject suitable for high-dose oxazaphosphorine retreatment, comprising determining the number of WBC in a blood sample derived from the subject that has previously undergone high-dose oxazaphosphorine treatment, wherein the subject is identified as being suitable for high-dose oxazaphosphorine retreatment if the number of WBC is consistent with incomplete immunosuppression. In some embodiments, incomplete immunosuppression is indicated by a WBC count of greater than zero. In the case of incomplete immunosuppression, the method may further comprise re-administration of high-dose oxazaphosphorine (e.g., high-dose cyclophosphamide) one or more times (retreatment) until the number of WBC is no longer consistent with incomplete immunosuppression. Likewise, the patient is identified as not being suitable for high-dose oxazaphosphorine retreatment if the number of WBC is consistent with complete or maximal immunosuppression (e.g., a WBC count of zero). In some embodiments, the method further comprises measuring ALDH in a sample including hematopoietic progenitor stem cells derived from the subject, wherein the subject is identified as being suitable for high-dose oxazaphosphorine treatment if: (a) the ALDH is consistent with a resistant ALDH in hematopoietic progenitor stem cells; and (b) the number of WBC is consistent with incomplete immunosuppression. In other embodiments, the method further comprises measuring ALDH in a sample including peripheral lymphocytes derived from the subject, wherein the subject is identified as being suitable for high-dose oxazaphosphorine treatment if: (a) the ALDH is consistent with a sensitive ALDH in peripheral lymphocytes; and (b) the number of WBC is consistent with incomplete immunosuppression.

Subjects

Various methods described herein can be used for treating a subject with an oxazaphosphorine drug and/or for identifying a subject as being suitable or not being suitable for oxazaphosphorine treatment (e.g., cyclophosphamide treatment), where the subject has an autoimmune disease, an allergic reaction, transplant rejection, cancer (or any combination of two or more of the foregoing).

In one embodiment, a subject being treated with an oxazaphosphorine drug and/or a subject being identified as suitable or not suitable for oxazaphosphorine (e.g., cyclophosphamide) treatment has an autoimmune disease. Exemplary autoimmune diseases include, but are not limited to, AIDS-associated myopathy, AIDS-associated neuropathy, Acute disseminated encephalomyelitis, Addison's Disease, Alopecia Areata, Anaphylaxis Reactions, Ankylosing Spondylitis, Antibody-related Neuropathies, Antiphospholipid Syndrome, Autism, Autoimmune Atherosclerosis, Autoimmune Diabetes Insipidus, Autoimmune Endometriosis, Autoimmune Eye Diseases, Autoimmune Gastritis, Autoimmune Hemolytic Anemia, Autoimmune Hemophilia, Autoimmune Hepatitis, Autoimmune Interstitial Cystitis, Autoimmune Lymphoproliferative Syndrome, Autoimmune Myelopathy, Autoimmune Myocarditis, Autoimmune Neuropathies, Autoimmune Oophoritis, Autoimmune Orchitis, Autoimmune Thrombocytopenia, Autoimmune Thyroid Diseases, Autoimmune Urticaria, Autoimmune Uveitis, Autoimmune Vasculitis, Behcet's Disease, Bell's Palsy. Bullous Pemphigoid, CREST, Celiac Disease, Cerebellar degeneration (paraneoplastic), Chronic Fatigue Syndrome, Chronic Rhinosinusitis, Chronic inflammatory demyelinating polyneuropathy, Churg Strauss Syndrome, Connective Tissue Diseases, Crohn's Disease, Cutaneous Lupus, Dermatitis Herpetiformis, Dermatomyositis, Diabetes Mellitus, Discoid Lupus Erythematosus, Drug-induced Lupus, Endocrine Orbitopathy, Glomerulonephritis, Goodpasture Syndrome, Goodpasture's Syndrome, Graves Disease, Guillain-Barre Syndrome, Guillian Barre Syndrome (Miller Fisher variant), Guillian Barre Syndrome (axonal), Guillian Barre Syndrome (demyelinating), Hashimoto's Thyroiditis, Herpes Gestationis, Human T-cell lymphomavirus-associated myelopathy, Huntington's Disease, IgA Nephropathy, Immune Thrombocytopenic Purpura, Inclusion body myositis, Interstitial Cystitis, Isaacs syndrome, Lambert Eaton myasthenic syndrome, Limbic encephalitis, Lower motor neuron disease, Lyme Disease, MCTD, Microscopic Polyangiitis, Miller Fisher Syndrome, Mixed Connective Tissue Disease, Mononeuritis multiplex (vasculitis), Multiple Sclerosis, Myasthenia Gravis, Myxedema, Meniere Disease, Neonatal LE, Neuropathies with dysproteinemias, Opsoclonus-myoclonus, PBC, POEMS syndrome, Paraneoplastic Autoimmune Syndromes, Pemphigus, Pemphigus Foliaceus, Pemphigus Vulgaris, Pernicious Anemia, Peyronie's Disease, Plasmacytoma/myeloma neuropathy. Poly-Dermatomyositis, Polyarteritis Nodosa, Polyendocrine Deficiency Syndrome, Polyendocrine Deficiency Syndrome Type 1, Polyendocrine Deficiency Syndrome Type 2, Polyglandular Autoimmune Syndrome Type I, Polyglandular Autoimmune Syndrome Type II, Polyglandular Autoimmune Syndrome Type III, Polymyositis, Primary Biliary Cirrhosis, Primary Glomerulonephritis, Primary Sclerosing Cholangitis, Psoriasis, Psoriatic Arthritis, Rasmussen's Encephalitis, Raynaud's Disease, Relapsing Polychondritis, Retrobulbar neuritis, Rheumatic Diseases, Rheumatoid Arthritis, Scleroderma, Sensory neuropathies (paraneoplastic), Sjogren's Syndrome, Stiff-Person Syndrome. Subacute Thyroiditis, Subacute autonomic neuropathy, Sydenham Chorea, Sympathetic Ophthalmitis, Systemic Lupus Erythematosus, Transverse myelitis, Type 1 Diabetes, Ulcerative Colitis, Vasculitis, Vitiligo, Wegener's Granulomatosis, Acrocyanosis, Anaphylactic reaction, Autoimmune inner ear disease, Bilateral sensorineural hearing loss, Cold agglutinin hemolytic anemia, Cold-induced immune hemolytic anemia, Idiopathic endolymphatic hydrops, Idiopathic progressive bilateral sensorineural hearing loss, Immune-mediated inner ear disease, and Mixed autoimmune hemolysis. In some embodiments, the immune disorder is multiple sclerosis (e.g., relapsing-remitting multiple sclerosis).

In some embodiments, the subject is suffering from an immune disorder, such as an autoimmune disease, an allergic reaction, or transplant rejection (including graft-versus-host-rejection (GVHD)), such as those disclosed herein. In some embodiments, the subject is suffering from, or at risk of developing, transplant rejection, and the oxazaphosphorine is to be administered or delivered to prevent (e.g., avoid or delay onset of) transplant rejection. In some embodiments, the subject is suffering from, or at risk of developing, graft-versus-host disease, and the oxazaphosphorine is to be administered or delivered to prevent (e.g., avoid or delay onset of) graft-versus-host disease.

Without wishing to be bound by theory, it is understood that methods described herein can be used for treating a subject with an oxazaphosphorine drug and/or for identifying a subject suitable for high-dose oxazaphosphorine (e.g., cyclophosphamide) treatment, where the subject has any immune disorder in which it would be desirable to replace the circulating auto-reactive lymphocytes with disease free immune cells. One of ordinary skill in the art can easily determine which diseases fall in this category, for example, by detecting auto-reactive antibodies or antibodies which react with self-antigens in a subject suffering from such a disease. Alternatively, by detecting cells in a subject which are capable of mounting an immune response against a self-antigen in the subject. Methods of diagnosing one or more autoimmune diseases encompassed by this disclosure are well-known in the art and can easily be performed by a skilled artisan.

In addition to autoimmune diseases, also encompassed by this invention are methods of treating a subject with an oxazaphosphorine drug and/or for identifying subjects suitable for oxazaphosphorine (e.g., cyclophosphamide) treatment, where the subject has an allergic reaction. Exemplary allergic reactions include, but are not limited to, systemic allergic reaction, an allergic reaction to immunotherapy, anaphylactic reaction, atopic disease, contrast allergy, drug allergy, food allergy, hypersensitivity reaction, insect sting allergy, latex allergy, penicillin allergy, and radiocontrast medium allergy. Examples of food allergies include an allergic reaction to peanuts or shellfish, for example.

In addition to autoimmune diseases and allergic reactions, also encompassed by the methods of the present invention are methods of treating a subject having transplant rejection with an oxazaphosphorine drug and/or methods for identifying subjects having transplant rejections as being suitable or not being suitable for oxazaphosphorine (e.g., cyclophosphamide) treatment. For example, in some embodiments, a subject has a transplant rejection which occurred during or following an allogenic antigen transplantation of organs, tissues, or cells into a host. In other embodiments, a subject has a transplant rejection which occurred during or following a xenogenic transplantation of organs, tissues, or cells into a host. In yet other embodiments, a subject has a transplant rejection which occurred during or following transplantation of autologous tissue, organs or cells into a host.

Transplant cells may be administered to the subject by any effective route. In one embodiment, the cells (e.g., bone marrow cells) are administered for treatment of a hereditary hemoglobinopathy (such as sickle cell anemia or thalassemia) and/or for treatment of a hematologic malignancy. In one embodiment, the transplant is a bone marrow transplant (e.g., allogenic bone marrow transplant).

Also encompassed by the methods of the present invention are subjects which have a transplant rejection that occurred during or following a transplant of an organ, tissue or cells from a half-matched donor, which usually results in graft versus host disease (GVHD).

In a further embodiment of the present invention, the subject has cancer. As used herein, the term "cancer" refers to disorders characterized by deregulated or uncontrolled cell growth, for example, carcinomas, sarcomas, lymphomas. The term "cancer" includes benign tumors, primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). In one embodiment of the present invention, the subject does not have cancer.

Exemplary cancers include, but are not limited to, Hodgkin's Lymphoma, Non-Hodgkin's Lymphoma, Chronic Lymphocytic Leukemia, Mantle Cell Lymphoma and Multiple Myeloma.

Preparation of Cell Sample Containing Hematopoietic Stem Cells

In various aspects of the methods of the invention, ALDH, for example, cytosolic ALDH, is measured in a cell sample including hematopoietic stem cells, for example, a cell suspension of pluripotent hematopoietic stem cells (pluripotent HSC), that is substantially free of lineage-committed cells. By definition, "pluripotent" hematopoietic stem cells are those progenitor cells having the ability to repopulate lymphohematopoietic lineages on a long-term basis.

In one embodiment, hematopoietic progenitor stem cells are derived from a subject having an autoimmune disease. In another embodiment, hematopoietic progenitor stem cells are derived from a subject having cancer. In yet other embodiments, a subject has an allergic reaction or transplant rejection.

Preparation of cell samples containing hematopoietic stem cells can be found, for example, in U.S. Pat. No. 5,876,956, incorporated by reference herein, in its entirety. Alternatively, a large proportion of differentiated cells may be removed in a cell sample by using, for example, a "relatively crude" separation. The source of the cells may be the bone marrow, fetal, neonate, or adult or other hematopoietic cell source, e.g., fetal liver or blood. For example, magnetic bead separations may be used initially to remove large numbers of lineage committed cells, namely major cell populations of the hematopoietic systems, including such lineages as T cells, B cells (both pre-B and B cells), myelomonocytic cells, or minor cell populations, such as megakaryocytes, mast cells, eosinophils and basophils.

In some embodiments of the methods of the present invention, a sample including hematopoietic progenitor stem cells includes a bone marrow aspirate derived from a subject.

In some embodiments, ALDH is measured in a sample derived from a subject having cancer, where the sample contains leukemia cells or other malignant cells.

In some embodiments, a sample derived from a subject includes a substantially homogeneous population of hematopoietic progenitor stem cells, e.g., hematopoietic stem cells.

The term "substantially homogeneous," as used herein, means that the sample derived from a subject being identified as being suitable or not suitable for high-dose oxazaphosphorine (e.g., cyclophosphamide) treatment includes no more than about 1%, or 2%, or 5%, or 10% of lineage-committed cells. Hematopoietic progenitor stem cells can be isolated using any technique well-known in the art or those described herein. For example, hematopoietic stem cells can be characterized as having one or more of the following attributes, for example, having a small size, generally from about 8 to 10 µm; expressing levels of ALDH from about 10 to about 30 nanomoles aldehyde oxidized/mg protein/min; being substantially free from expression of markers specific for committed lymphohematopoietic lineages, such as CD19, CD33 and CD5; and being negative for expression of c-kit and Thy. In some embodiments, a sample derived from a subject is enriched for hematopoietic stem cells, for example, by flow cytometry using anti-CD34 antibody. Other markers that can be used for identification and isolation of hematopoietic stem cells include, but are not limited to, c-kit and Thy.

In some embodiments, a cell sample including hematopoietic progenitor stem cells can be obtained by isolating cells that express an intracellular enzyme which hydrolyzes a fluorescent non-polar substrate. Preferably, the enzyme is ALDH and the substrate is DAAA as described herein. In other embodiments, the cell sorting step is performed using automated cell sorting, such as fluorescence activated cell sorting (FACS), a high speed method of sorting fluorescent cells.

Preparation of Cell Sample Containing Peripheral Lymphocytes

In various aspects of the methods of the invention, ALDH, for example, cytosolic ALDH, is measured in a cell sample including peripheral lymphocytes, for example, a cell suspension substantially enriched of lineage-committed immune cells. By definition, these lymphocytes originate from a common lymphoid progenitor and form the innate and humoral immune system. These cells are commonly referred to as T cells, B cells and natural killer (NK) cells, white blood cell, and/or dendritic cells. These include such lineages as T cells, B cells (both pre-B and B cells), myelomonocytic cells, or minor cell populations, such as megakaryocytes, mast cells, eosinophils and basophils.

In some embodiments, the peripheral lymphocytes are CD4-positive (also known as helper T-cells, CD4-positive lymphocytes, or CD4-positive T-cells). In addition to flow based assays (e.g., flow cytometry, such as fluorescence activated cell sorting (FACS)), any of various non-flow cytometric technologies may be utilized such as manual assays using optical or fluorescence microscopes (e.g., Dynal immune bead-based assay, Coulter immune bead-based assay), etc. (Pattanapanysat K et al., *Cytometry B. Clin. Cytom.*, 2005, 65(1):29-36; Pattanapanysat K. and Thakar M. R., *Indian J. Med. Res.*, 2005, 121(4):539-549; Paxton H. et al., *Clin. Diagn. Lab. Immunol.*, 1995, 2(1):104-114; Jannosy G. et al., *Br. J. Haemato.l*, 2000, 111:1198-208; Nicholsan J, K. A. et al., *J. Immunol. Methods*, 1994, 177:43-54).

Optionally, to measure ALDH in a sample of peripheral lymphocytes, purification of the sample for CD4-positive lymphocytes and/or other target surface markers can be carried out using methods known in the art, and ALDH contributed by CD4-positive lymphocytes can be measured, for example.

In one embodiment, peripheral lymphocytes are derived from a subject having an autoimmune disease. In another embodiment, peripheral lymphocytes are derived from a subject having cancer. In yet other embodiments, peripheral lymphocytes are derived from a subject having an allergic reaction or transplant rejection.

Preparation of cell samples enriched in peripheral lymphocytes can be obtained using known methods in the art including flow cytometry. The source of the cells may be the bone marrow, fetal, neonate, or adult or other hematopoietic cell source, e.g., fetal liver or blood. For example, magnetic bead separations may be used initially to remove large numbers of lineage committed cells, namely major cell populations of the hematopoietic systems, including such lineages as T cells, B cells (both pre-B and B cells), myelomonocytic cells, or minor cell populations, such as megakaryocytes, mast cells, eosinophils and basophils.

In some embodiments, ALDH is measured in a sample derived from a subject having cancer, where the sample contains leukemia cells or other malignant cells.

In some embodiments of the methods of the present invention a sample including peripheral lymphocytes includes a banked blood sample from the patient.

In some embodiments, a sample derived from a subject includes a substantially homogeneous population of peripheral lymphocytes. The term "substantially homogeneous," as used herein, means that the sample derived from a subject being identified as being suitable or not suitable for high-dose cyclophosphamide treatment includes more than about 1%, or 2%, or 5%, or 10% of lineage-committed cells. Hematopoietic stem cells can be isolated using any technique well-known in the art or those described herein. For example, peripheral lymphocytes can be characterized as having one or more of the following attributes, for example expression of markers specific for committed lymphohematopoietic lineages, such as CD19, CD33 and CD5; or being positive for expression of c-kit and Thy.

Measurement of ALDH

Various methods known in the art and those described herein can be used for measuring ALDH in a cell sample including hematopoietic progenitor stem cells or peripheral lymphocytes. In some embodiments, ALDH is measured using flow cytometry. In other embodiments, ALDH is measured using western blot analysis.

In some embodiments, ALDH activity is measured using a fluorescent substrate called dansyl-aminoacetaldehyde or DAAA, as a substrate. In another exemplary method, ALDH activity is measured using BODIPY aminoacetaldehyde or BAAA as a substrate (commercially available as ALDEFLUOR™). In some embodiments of the various aspects of the present invention, ALDH is measured by: (a) contacting a sample including peripheral lymphocytes derived from a subject with DAAA; and (b) measuring oxidation of DAAA. In some embodiments of the various aspects of the present invention, ALDH is measured by: (a) contacting a sample including hematopoietic progenitor stem cells derived from a subject with DAAA; and (b) measuring oxidation of DAAA.

In some embodiments, measurement of ALDH includes the steps of contacting a cell sample containing hematopoietic progenitor stem cells, peripheral lymphocytes, or granulocytes with a cell-permeable, non-polar fluorescent aldehyde that is rendered polar by contact with ALDH, for example, by oxidation. Once rendered polar, the fluorescent aldehyde is no longer permeable to the cell membrane and, hence, is trapped within only those cells in the cell mixture that express the intracellular marker. Cells containing the trapped polar, non-permeable fluorescent aldehyde so formed are identified by fluorescence using techniques and equipment well known to those of skill in the art. Exemplary fluorescence techniques include, but are not limited to, automated fluorescence cell sorting techniques that separate cells containing or having attached thereto a fluorescent marker, such as Fluorescence Activated Cell Sorting (FACS). Such fluorescence cell sorting techniques are well known to those of skill in that art.

In some embodiments, a fluorescent cell permeable aldehyde is a substrate for aldehyde dehydrogenase (ALDH), and is oxidized by contact with intracellular ALDH to a non-permeable polar fluorescent molecule. When the fluorescent polar molecule is contacted by a light beam having the requisite wavelength to excite the molecule, the fluorescent light emitted as the molecule drops back to its ground state is detected, thereby indicating the presence of a cell or cell population containing intracellular ALDH. In some embodiments, the fluorescent aldehyde is dansylaminoacetaldehyde (DAAA), a substrate for aldehyde dehydrogenase, or analogs thereof. Dansyl fluorescence is excited at both 351.1 nm and 363.8 nm and is detected at about 521 nm. Description of the synthesis of DAAA can be found in U.S. Pat. No. 5,876,956, incorporated by reference herein, in its entirety.

A general method for producing a non-polar fluorescent aldehyde for measuring ALDH is to react a physiologically compatible fluorescent molecule bearing an electrophilic group and a protected aldehyde, such as a methyl or ethyl acetal having a nucleophilic group. For example, the fluorescent electrophile may be a sulfonyl chloride, such as dansyl chloride or Texas Red sulfonyl chloride; an isothiocyanate, such as fluorescein isothiocyantate; an N-hydroxysuccinimide, such as N-hydroxy succinimidorhodamine; or a thiol-reactive fluorescent derivative, such as 5-iodoacetamidofluorescein. The protected aldehyde may contain one of a number of nucleophilic groups, such as an amino, hydroxyl, phenolic, or thiol group.

Without wishing to be bound by theory, it is contemplated that, any suitable characteristic associated with ALDH such as, for example, mRNA level, polypeptide amount, ALDH activity, transcription rate, translation rate etc., may be used as an indicator for identifying subjects that are suitable for high-dose cyclophosphamide treatment. In some embodiments, ALDH level, for example, amount of ALDH polypeptide present is used as an indicator for identifying subjects suitable for high-dose cyclophosphamide treatment. In other embodiments, ALDH activity is used as an indicator for identifying subjects suitable for high-dose cyclophosphamide treatment.

In some embodiments, ALDH levels or activity are measured in cancer cell populations, e.g., breast cancer cells. In some embodiments, ALDH levels or activity are measured in non-cancer cell populations, e.g., non-breast cancer cells.

In some embodiments, ALDH from peripheral lymphocytes determined to be CD4-positive (e.g., by purification or separation) is measured.

White Blood Cell Count

It also has been observed that in patients receiving oxazaphosphorine therapy for autoimmune diseases, patients who achieved maximal immunosuppression following the therapy as indicated by their white blood cell (WBC) count reaching 0 (zero per microliter or per cubic millimeter ($mm^3$)) experience a better clinical outcome and lessened risk of disease relapse than patients whose WBC count did not reach zero following therapy. Analysis of the banked blood of a series of patients following high-dose cyclophosphamide treatment demonstrated that patients who reached a white blood cell count of 0 and subsequently enjoyed a better clinical outcome had a much lower level of ALDH activity than the patient who relapsed without reaching a WBC of 0.

Accordingly, it may be beneficial to monitor the WBC count of patients before, during and/or after oxazaphosphorine treatment and, if the number WBC are consistent with incomplete immunosuppression, retreating the subject with oxazaphosphorine. Thus, another aspect of the invention is a method for identifying a subject suitable for oxazaphosphorine retreatment, comprising determining the number of WBC in a blood sample derived from the subject wherein the subject is identified as being suitable for oxazaphosphorine retreatment if the number of WBC is consistent with incomplete immunosuppression. WBC numbers themselves can be used as an indicator or WBC numbers can be used in conjunction with ALDH measurement to determine a patient's suitability for oxazaphosphorine treatment or re-retreatment.

In some embodiments, incomplete immunosuppression is indicated by the existence of a WBC count of greater than zero. In some embodiments, incomplete immunosuppression is indicated by the existence of a WBC count of greater than 4. In some embodiments, incomplete immunosuppression is indicated by the existence of a WBC count of greater than 10. In some embodiments, incomplete immunosuppression is indicated by the existence of a WBC count of greater than 12. In some embodiments, incomplete immunosuppression is indicated by the existence of a WBC count of greater than 15. In some embodiments, incomplete immunosuppression is indicated by the existence of a WBC count of greater than 20.

Various methods that are known in the art may be utilized in determining the number of WBC in a sample, such as flow cytometry, including fluorescence activated cell sorting (FACS). Automated blood counting can be utilized using automated hematology analyzers, for example. Typically, blood counting machines aspirate a very small amount of the blood specimen through narrow tubing. Within the tubing are sensors that count the number of cells passing through it, and can identify the cell (flow cytometry). Automated blood counting machines that may be utilized include, for example, BECKMAN COULTER LH series, SYSMEX XE-2100, SIEMENS ADVIA 120 and 2120, and the ABBOTT CELL-DYN series.

Typically, methods for estimating WBC in biological fluids are based on automated cell counting technologies, in which the sample is diluted, and cells of different sizes and shapes are counted in a flow cell. See, for example, U.S. Pat. Nos. 2,656,508; 3,502,973; and 6,159,740. In addition, U.S. Pat. No. 6,709,868 describes a method for measuring WBC count by capturing white blood cells from the fluid sample by a retainer, removing red blood cells and other interfering substances by a wash solution, and reading the result of a color reaction in which an ester which is present on the white blood cells cleaves a chromogenic substrate which produces a water insoluble dye. The apparatus for use in the method of U.S. Pat. No. 6,709,868 includes a retainer for white blood cells that has a dye substrate immobilized therein and an absorption layer that wicks and takes up all excess washing solution flowing past the sample. In addition to flow based assays, any of various non-flow cytometric technologies may be utilized such as manual assays using optical or fluorescence microscopes (e.g., Dynal immune bead-based assay, Coulter immune head-based assay), etc. (Pattanapanysat K et al., *Cytometry B. Clin. Cytom.*, 2005, 65(1):29-36; Pattanapanysat K. and Thakar M. R., *Indian J. Med. Res.*, 2005, 121(4): 539-549; Paxton H. et al., *Clin. Diagn. Lab. Immunol.*, 1995, 2(1):104-114; Jannosy G. et al., *Br. J. Haemato.l*, 2000, 111: 1198-208; Nicholsan J, K. A. et al., *J. Immunol. Methods*, 1994, 177:43-54). Though less efficient and subject to human error, the WBC count can be carried out manually. For example, a blood film or peripheral blood smear can be made, which is a slide made from a drop of blood, that allows the cells to be examined microscopically.

Optionally, additional diagnostic tests can be carried out on the blood samples. For example, the WBC count can be determined as part of the complete blood count (CBC).

In some embodiments, the blood sample is selected from among peripheral blood, bone marrow aspirate, and apheresis. In some embodiments, the blood sample comprises a sample of banked blood.

Optionally, the blood sample can be pre-treated, such as with an anti-coagulant or other agent, prior to determining the number of WBC, e.g., with heparin, ethylenediaminetetraacetic acid (EDTA), citrate, or double oxalate; or separated or purified.

In some embodiments, the method further comprises re-administering oxazaphosphorine to the subject one or more times if the WBC number is consistent with incomplete immunosuppression (e.g., if the number of WBC are greater than zero per microliter of sample). In some embodiments, the method further comprises ceasing high-dose oxazaphosphorine re-treatment once the number of WBC in a sample obtained from the patient are no longer consistent with incomplete immunosuppression (e.g., the patient reaches maximal immunosuppression as indicated by a WBC count of zero per microliter of sample).

In some embodiments, the methods of the present invention include determining the number of WBC in a plurality of blood samples derived from the subject over time, and further includes administering oxazaphosphorine to the subject one or more times until the number of WBC are no longer consistent with incomplete immunosuppression.

In some embodiments, retreatment alleviates or eliminates one or more symptoms associated with the immune disorder. In some embodiments, the immune disorder is multiple sclerosis (such as relapsing-remitting multiple sclerosis) or another autoimmune disorder, and wherein the retreatment results in partial or full restoration of function, which can be determined, for example, by multiple sclerosis functional composite (MSFC) score or Kurtzke expanded disability status scale (EDSS).

In some embodiments, the subject has previously undergone oxazaphosphorine administration, and the blood sample is derived from the subject at a time point after the previous oxazaphosphorine administration. For example, blood samples may be obtained from the subject and WBC number determined on a daily basis or semi-daily basis for a number of days or weeks following oxazaphosphorine treatment. In some embodiments, the one or more time points at which a blood sample is obtained from the subject and WBC number determined are within about two weeks of initiating oxazaphosphorine administration. Oxazaphosphorine can be re-administered to the subject one or more times if the number of WBC is consistent with incomplete immunosuppression (e.g., greater than zero WBC per microliter of blood sample).

In some embodiments, the dosage of oxazaphosphorine drug administered before and/or after incomplete immunosuppression is determined is 50 mg/kg/day. In some embodiments, the oxazaphosphorine drug is administered to the subject for 4 days after incomplete immunosuppression is determined. In some embodiments, the amount of oxazaphosphorine drug administered is 200 mg/kg administered over 4 consecutive days. In some embodiments, the amount of oxazaphosphorine drug administered before and/or after incomplete immunosuppression is determined is 50 mg/kg/day administered for 4 days.

In some embodiments, the oxazaphosphorine drug is selected from the group consisting of: cyclophosphamide, ifosfamide, perfosfamide, trophosphamide, and a pharmaceutically acceptable salt, solvate, prodrug or metabolite thereof. In some embodiments, the oxazaphosphorine drug is cyclophosphamide or a pharmaceutically acceptable salt or metabolite thereof. In some embodiments, the oxazaphosphorine drug comprises cyclophosphamide. In some embodiments, the oxazaphosphorine drug is cyclophosphamide administered in the amount of 50 mg/kg for 4 days before determining the WBC count, and/or after incomplete immunosuppression is determined.

In some embodiments, the method further comprises measuring ALDH in a sample including hematopoietic progenitor stem cells derived from the subject, wherein the subject is identified as being suitable for oxazaphosphorine treatment if: (a) the ALDH is consistent with a resistant ALDH in hematopoietic progenitor stem cells; and (b) the number of WBC is consistent with incomplete immunosuppression. In other embodiments, the method further comprises measuring ALDH in a sample including peripheral lymphocytes derived from the subject, wherein the subject is identified as being suitable for high-dose oxazaphosphorine treatment if: (a) the ALDH is consistent with a sensitive ALDH in peripheral lymphocytes; and (b) the number of WBC is consistent with incomplete immunosuppression. The blood sample in which WBC number is determined and the sample in which ALDH is measured can be the same sample or different samples. Various methods known in the art and those described herein can be used for measuring ALDH in a cell sample including hematopoietic progenitor stem cells or peripheral lymphocytes.

Identification of Subjects Suitable for Oxazaphosphorine Treatment

In some aspects, the present invention is directed to methods for selecting a subject suitable for oxazaphosphorine therapy. In some embodiments, the methods include determining whether treatment with an oxazaphosphorine can be safe and effective for the subject based on one or more safety or efficacy factors and selecting a subject suitable for oxazaphosphorine therapy where it is determined that treatment can be safe and effective.

In some embodiments, the safety or efficacy factors include an ALDH inhibition factor. ALDH inhibition factors include, but are not limited to, hormonal contraceptive use (e.g., estrogen and/or progestin via oral administration, patch or injection), tobacco use, and chronic alcohol use. ALDH inhibition factors also include, but are not limited to the use of ALDH inhibiting agents and/or ALDH activating agent.

The ALDH inhibiting agent can be any of the ALDH inhibiting agents listed herein, including, but not limited to, disulfiram, calcium carbimide, diazepam, chlordiazepoxide, isosorbide dinitrate, nitroglycerine, chlorpropamide, tolazamide, and cephalosporin. The ALDH activating agent can be any of the ALDH activating agents listed herein, including calcium ions.

In some embodiments, the safety or efficacy factors include an ALDH level consistent with a resistant ALDH level in hematopoietic progenitor stem cells. In some embodiments, the safety or efficacy factors include an ALDH level consistent with a resistant ALDH level in peripheral lymphocytes.

In some embodiments, the method further includes periodically determining whether treatment with an oxazaphosphorine continues to be safe and effective for the subject based on one or more safety or efficacy factors. In some embodiments, the method further includes monitoring white blood cell count before treatment, during treatment, after treatment, or a combination of two or more of the foregoing.

In some aspects, the present invention provides methods for delivering an oxazaphosphorine to subjects in need thereof while restricting access to the oxazaphosphorine by subjects for whom the drug may be contraindicated. In some embodiments, the methods include obtaining subject information relating to the existence of one or more contraindication factors; and permitting delivery of the oxazaphosphorine only after it has been determined that the subject can safely be treated based on the information relating to one or more contraindication factors.

In some embodiments, the contraindication factors include one or more ALDH inhibition factors. ALDH inhibition factors include, but are not limited to, hormonal contraceptive use (e.g., estrogen and/or progestin via oral administration, patch or injection), tobacco use, and chronic alcohol use. ALDH inhibition factors also include, but are not limited to the use of ALDH inhibiting agents and/or ALDH activating agent.

In some embodiments, permitting delivery includes generating a prescription approval code to be retrieved by a pharmacy before a prescription is filled. In some embodiments, permitting delivery includes allowing the shipment of a dosage to a pharmacy. In some embodiments, permitting delivery includes allowing a patient to be treated with the oxazaphosphorine drug in a prepackaged dosage.

In some embodiments, the methods further include counseling the patient as to risk avoidance measures in response to the information relating to the existence of one or more contraindication factors.

Subsequent to measuring ALDH in a sample containing hematopoietic progenitor stem cells and/or peripheral lymphocytes derived from a subject, the subject is identified as being suitable or not being suitable for oxazaphosphorine treatment (e.g., high-dose cyclophosphamide treatment), by for example, comparing the ALDH to a predetermined value.

In some embodiments, a predetermined value is a resistant ALDH, as described herein. Accordingly, in some embodiments, a subject is identified as being suitable for high-dose oxazaphosphorine treatment (e.g., high-dose cyclophosphamide treatment), if the ALDH (e.g., level or activity of ALDH) in a sample including hematopoietic progenitor stem cells derived from the subject is consistent with a resistant ALDH. A resistant ALDH is an ALDH (e.g., level or activity of ALDH) which is sufficient to confer resistance of a hematopoietic progenitor stem cell to high-dose oxazaphosphorine (e.g., high-dose cyclophosphamide). In other words, a resistant ALDH is that level or activity of ALDH in a hematopoietic progenitor stem cell or a sample containing hematopoietic progenitor stem cells, at which the cell or cells survive exposure to oxazaphosphorine (e.g., high-dose cyclophosphamide). In other embodiments, a subject is identified as not being suitable for high-dose oxazaphosphorine treatment if the ALDH (e.g., level or activity) is not consistent with a resistant ALDH, or if it is consistent with a sensitive ALDH for the stem cells.

It is understood that a resistant ALDH can be a single value or a range of ALDH which is sufficient for conferring resistance to oxazaphosphorine (e.g., high-dose cyclophosphamide). For example, in one embodiment, a resistant ALDH is a level of ALDH protein in a sample containing hematopoietic progenitor stem cells which survive exposure to one or more doses of oxazaphosphorine. In another embodiment, a resistant ALDH is an activity of ALDH in a sample containing hematopoietic progenitor stem cells which survive exposure to one or more doses of high-dose oxazaphosphorine.

It is understood that a resistant ALDH may either be a value known to one of ordinary skill in the art or it may be determined prior to measuring ALDH in a sample derived from a subject being identified as being suitable or not suitable for high-dose oxazaphosphorine treatment (e.g., high-dose cyclophosphamide treatment).

For example, in some embodiments, a predetermined or resistant ALDH is at least 10 to about 30 nanomoles aldehyde oxidized/mg protein/min. Accordingly, in some embodiments, a subject having ALDH at least 10 to about 30 nanomoles aldehyde oxidized/mg protein/min, or higher, is identified as being suitable for high-dose oxazaphosphorine treatment.

In some embodiments, a predetermined ALDH is determined, for example, by expressing varying amounts of ALDH in cells, for example, in cell culture, and exposing them to one or more doses of high-dose oxazaphosphorine treatment (e.g., high-dose cyclophosphamide). Accordingly, a resistant ALDH is the amount or activity of ALDH at which the cells are resistant to high-dose oxazaphosphorine treatment (e.g., high-dose cyclophosphamide). ALDH in a sample derived from a subject being identified using the methods of the invention can subsequently be compared with the resistant ALDH to determine whether the subject is suitable or not suitable for high-dose oxazaphosphorine treatment (e.g., high-dose cyclophosphamide treatment).

In some embodiments according to the present invention, a subject is identified as being suitable or not being suitable for high-dose oxazaphosphorine treatment (e.g., high-dose cyclophosphamide treatment) based on the ALDH relative to an appropriate control.

For example, in some embodiments, a subject is identified as being suitable for high-dose oxazaphosphorine treatment (e.g., high-dose cyclophosphamide treatment) if a sample containing hematopoietic progenitor stem cells derived from the subject includes an ALDH (e.g., level or activity) which is consistent with appropriate control (i.e., equal or higher than the control in case of a single cut-off value or falling within the appropriate range). Conversely, a subject is identified as not being suitable for high-dose oxazaphosphorine treatment if the ALDH (e.g., level or activity) in a sample containing hematopoietic progenitor stem cells derived from the subject is not consistent with an appropriate control (i.e., lower than the control in case of a single cut-off value or not falling within the appropriate range).

It is understood that an appropriate control could be a single value or a range of ALDH which is known to confer resistance to high-dose oxazaphosphorine treatment (e.g., high-dose cyclophosphamide treatment). An appropriate control known in the art may be used in the methods of the invention or it may be determined using one or more methods described herein and those that are known in the art.

For example, in one embodiment, an appropriate control is determined based on the response of a population of subjects to high-dose cyclophosphamide. In some embodiments, a number of samples containing hematopoietic progenitor stem cells are derived from a population of subjects (for example, at least 10, or at least 15, or at least 20, or at least 30, or at least 40, or at least 50, or at least 100, or more). Accordingly, ALDH (e.g., level or activity) can be measured in various samples prior to treatment with high-dose cyclophosphamide. An appropriate control can subsequently be determined as that ALDH (e.g., level or activity) sufficient for conferring resistance to high-dose cyclophosphamide. In other words, an appropriate control can be a single value (e.g., mean or median of ALDH level or activity) or a range of ALDH level or activity in the samples, at which the hematopoietic progenitor stem cells survive exposure to high-dose oxazaphosphorine (i.e., resistant ALDH). Accordingly, a subject is subsequently identified as being suitable for high-dose oxazaphosphorine treatment (e.g., high-dose cyclophosphamide treatment) if a sample containing hematopoietic progenitor stem cells derived from the subject includes an ALDH (e.g., level or activity) which is consistent with (i.e., at least equal to or higher than) the appropriate control. Conversely, the subject is identified as not being suitable for high-dose oxazaphosphorine treatment (e.g., high-dose cyclophosphamide treatment) if the ALDH (e.g., level or activity) is lower than the appropriate control.

In some embodiments, the methods include measuring ALDH in a sample including hematopoietic progenitor stem cells derived from the subject, where the subject is identified as being suitable for high-dose oxazaphosphorine treatment if the ALDH is consistent with a resistant ALDH standard in hematopoietic progenitor stem cells. Conversely, a subject is identified as not being suitable for high-dose oxazaphosphorine treatment if the ALDH is not consistent with a resistant standard or is consistent with a sensitive ALDH standard in hematopoietic progenitor stem cells.

In some embodiments, the methods include measuring ALDH in a sample including peripheral lymphocytes derived from the subject, where the subject is identified as being suitable for high-dose oxazaphosphorine treatment if the ALDH is consistent with a sensitive ALDH standard in peripheral lymphocytes. Conversely, a subject is identified as not being suitable for high-dose oxazaphosphorine treatment if the ALDH is not consistent with a sensitive or is consistent with a resistant ALDH standard in peripheral lymphocytes.

In some embodiments, the methods include measuring ALDH in a sample including peripheral lymphocytes derived from the subject, where the subject is identified as being suitable for high-dose oxazaphosphorine treatment if the ALDH is consistent with an ALDH standard demonstrated to allow maximal immunosuppression in the subject following administration of high-dose oxazaphosphorine.

In some embodiments, the methods include measuring ALDH in a sample including hematopoietic progenitor stem cells derived from a subject, where the subject is identified as being suitable for high-dose oxazaphosphorine treatment if the measured ALDH is consistent with an appropriate standard of ALDH. Conversely, a subject is identified as not being suitable for high-dose oxazaphosphorine treatment if ALDH is not consistent with an appropriate standard.

In some embodiments, the methods include measuring ALDH in a sample including peripheral lymphocytes derived from a subject, where the subject is identified as being suitable for high-dose oxazaphosphorine treatment if ALDH is consistent with an appropriate standard. Conversely, a subject is identified as not being suitable for high-dose oxazaphosphorine treatment if ALDH is not consistent with an appropriate standard.

Additional methods for identifying a subject suitable for high-dose can be found, for example, in WO 2008/034071, the contents of which is incorporated herein in its entirety by this reference.

Without wishing to be bound by any particular theory, it is believed that administration of oxazaphosphorine, e.g., high dose cyclophosphamide is contra-indicated in patients who have successfully achieved a durable remission in tumors following vaccination with an autologous, anti-tumor, anti-idiotype vaccine. Thus, patients who achieve a lasting remission with an autologous, anti-tumor, anti-idiotype vaccine (e.g., BIOVAXID® and/or BIOVAXID® boosters) may be placed in jeopardy of a tumor relapse if the immunity due to the vaccine is either permanently or temporarily disrupted or modified, e.g., following a course of oxazaphosphorine, e.g., high-dose cyclophosphamide, therapy.

Accordingly, in some aspects, the present invention provides a method for determining whether a subject is suitable for high-dose oxazaphosphorine therapy. In some embodiments, the method includes determining whether the subject has undergone treatment with an autologous, anti-idiotype vaccine; and selecting a subject as non-suitable for high-dose oxazaphosphorine therapy where it is determined that the subject has undergone treatment for a B cell malignancy with the autologous, anti-idiotype vaccine and has achieved complete remission following vaccination. In some embodiments, the autologous, anti-idiotype vaccine is the BIOVAXID® vaccine. BIOVAXID® is a patient-specific follicular lymphoma (FL) vaccine derived from an individual subject's cancerous cells.

Controlled Access and Safety

In some aspects, the present invention provides a system for ensuring the safety or efficacy of a treatment that includes oxazaphosphorine administration. In some embodiments, the system includes selecting a set of safety and efficacy factors associated with the safe and effective treatment of a subject with an oxazaphosphorine drug; defining a set of information to be obtained from a subject including information probative of the set of selected safety and efficacy factors associated with the safe and effective treatment of a subject with an oxazaphosphorine drug; determining whether treatment that includes an oxazaphosphorine administration can be safe and effective for the subject based on the set of information; and generating a prescription approval code if it is determined that the treatment including the oxazaphosphorine administration can be safe and effective.

In some embodiments, the safety or efficacy factors include an ALDH inhibition factor. ALDH inhibition factors include, but are not limited to, hormonal contraceptive use (e.g., estrogen and/or progestin via oral administration, patch or injection), tobacco use, and chronic alcohol use. ALDH inhibition factors also include, but are not limited to the use of ALDH inhibiting agents and/or ALDH activating agent.

The ALDH inhibiting agent can be any of the ALDH inhibiting agents listed herein, including, but not limited to, disulfiram, calcium carbimide, diazepam, chlordiazepoxide, isosorbide dinitrate, nitroglycerine, chlorpropamide, tolazamide, and cephalosporin. The ALDH activating agent can be any of the ALDH activating agents listed herein, including calcium ions.

In some embodiments, the safety or efficacy factors include an ALDH level consistent with a resistant ALDH level in hematopoietic progenitor stem cells. In some embodiments, the safety or efficacy factors include an ALDH level consistent with a resistant ALDH level in peripheral lymphocytes.

In some embodiments, the method further includes periodically determining whether treatment with an oxazaphosphorine continues to be safe and effective for the subject based on one or more safety or efficacy factors. In some embodiments, the method further includes monitoring white blood cell count before treatment, during treatment, after treatment, or a combination of two or more of the foregoing.

In some embodiments, a subject will be screened for pregnancy and to ensure they match all necessary inclusion criteria and exclusion criteria. If a subject meets all necessary inclusion criteria and exclusion criteria and is not pregnant, they will be enrolled in the program, e.g., through registration software to verify their eligibility and ensure each subject's cyclophosphamide dose for infusion is appropriately assigned and validated.

In some embodiments, a female of childbearing potential will commit to use two forms of effective contraception simultaneously for one month before, during, and for one month after therapy. Similarly, male subjects will commit to use latex condoms every time they engage in heterosexual sexual intercourse. In some embodiments, a female of childbearing potential will have at least two negative urine or blood (serum) pregnancy tests before commencement of therapy. In some embodiments, the patient will be re-tested each month during therapy and receive a negative result prior to receiving each dosage. In some embodiments, failure to receive a negative result on a pregnancy test will constitute grounds for suspension of therapy.

Inclusion criteria may include, but are not limited to age criterion and active disease requirements (e.g., subjects with one or more disease indications or relapses within the prior twelve months). Exclusion criteria may include, but are not limited to any risk of pregnancy, a history of hormonal contraceptives or disulfiram exposure (e.g., exposure to hormonal contraceptives or disulfiram for the 120 days prior to commencement of therapy), a cardiac ejection fraction of less than 45%, a serum creatinine level of greater than 2.0, any indication of patient being pre-terminal or moribund, bilirubin levels of greater than 2.0, transaminase levels greater than twice the normal level, presence of items which would hinder monitoring of disease/disorder progression (e.g., pacemakers and implants which would inhibit the use of MRIs), WBC count less than 3000 cells/µl, platelet count of less than 100,000 cells/µl (untransfused), active infections, other serious medical illness. In some embodiments, failure to meet all of the inclusions and/or meeting any of the exclusion criteria will constitute grounds for suspension of therapy.

In some embodiments, the system provides a validation system to ensure patients receiving therapy do not concurrently receive medications with known interactions with cyclophosphamide. Medications with known severe interactions with cyclophosphamide include, but are not limited to cyclosporine, etanercept, allopurinol, live bacillus of calmette and guerin vaccine, tamoxifen, smallpox vaccine, live rubella virus vaccine, live mumps virus vaccine, live poliovirus vaccine, live measles virus vaccine, varicella virus vaccine, yellow fever vaccine, pentostatin, typhoid vaccine, St. John's wort, trastuzumab and live rotavirus vaccine. Medications with known moderate interactions with cyclophosphamide include, but are not limited to chloramphenicol, ondansetron, nevirapine, succinylcholine, digoxin, hydrochlorothiazide and indomethacin.

Optionally, the methods and systems of the invention further comprise virological monitoring, including assaying a sample obtained from the subject (e.g., blood, urine, saliva, bronchioalveolar lavage specimens, plasma, other bodily fluids, breath, or tissues) for the presence of viruses, such as herpesvirus (HSV), before administration of the oxazaphosphorine (e.g., high dose or low dose). In one embodiment, low dose oxazaphosphorine (e.g., low dose cyclophosphamide) is administered for treatment of cancer. Examples of herpesviruses include but are not limited to herpes simplex virus 1 (HSV-1), herpes simplex virus 2 (HSV-2), varicella-zoster virus (VZV), Epstein-Barr virus (EBV), cytomegalovirus (CMV), herpesvirus 6 (HHV-6), herpesvirus 7 (HHV-7), and herpesvirus 8 (HHV-8), also known as Kaposi's sarcoma associated herpesvirus (KSHV). Other examples of viruses of concern include respiratory viruses (e.g., adenovirus, influenza, respiratory syncytial virus (RSV)), papovavirus (e.g., papilloma, polyomavirus such as BKV and JCV), measles, hepatitis A (HAV), hepatitis B (HBV), hepatitis C(HCV), enterovirus, parvovirus, rabies virus, Rubella virus, Coxsackievirus, and human lymphotrophic virus.

Assaying for the presence of viruses, e.g., monitoring viral titers, can be done before, during, or after ALDH level is determined. In subjects determined to have low ALDH levels in the peripheral lymphocytes (and, thus, more susceptible to infection), a suitable antiviral agent can be administered in a timely fashion. Preferably, a sample is obtained at one or more time points following administration of the oxazaphosphorine and assayed for viruses as well. Laboratory techniques that may be utilized for detection and quantification of virus include, for example, virus culture, viral serology, viral DNA detection by polymerase chain reaction (PCR), and viral RNA detection by reverse transcription-PCR. Preferably, assays are quantitative or semi-quantitative. PCR and RT-PCR detection methods are preferred, as they generally offer the advantages of rapid turn-around time, high-sensitivity, and high-specificity.

In some embodiments, when all criteria are met, software generates an approval code, preferably with an expiration date, that is transmitted to the filling facility or conveyed to the drug provider to communicate that the patient is approved for drug administration (e.g., drug infusion). The terms "approval code", "approval status code", "prescription approval code", "authorization code", and "prescription authorization code" are used herein interchangeably, and can comprise, for example, a label, signal, tone, bar code, number, series of numbers, color, series of colors, letter, series of letters, symbol, series of symbols, hologram(s), a combination of two or more of the foregoing, or other form of communication. The approval code may be readable to humans, computer-readable, or both. In some embodiments, the approval code includes an indication of the oxazaphoshorine (e.g., cyclophosphamide) dose to be administered (e.g., infused). The approval code may be transmitted or conveyed to the filling facility or the drug provider by any method, such as telephone, facsimile, interne, postal mail, etc. In some embodiments, the approval code includes the patient's unique identifier. In some embodiments, the approval code is affixed to, or otherwise associated with, a container which includes the oxazaphosphorine (e.g., cyclophosphamide). In some embodiments, the container includes the oxazaphosphorine dosage. The oxazaphosphorine is then administered to the subject whose identity is associated with the approval code. The container to which the approval code is affixed, or otherwise associated, may be, for example, a flexible container such as an infusion bag, or a rigid container such as that which may be used for lyophilized drugs. Lyophilized drugs may be reconstituted at an infusion facility for administration to the patient. Drug containers may be delivered or shipped to the filling facility or drug provider by any method, such as mail or courier. In those embodiments in which the approval code is affixed to the drug container(s), the approval code may be directly or indirectly affixed to the drug container(s). For example, in some embodiments, the approval code is affixed to, or otherwise associated with a packaging that contains one or more containers containing oxazaphosphorine for the particular patient.

In some embodiments, once the oxazaphosphorine container is received at the administration facility (e.g., an infusion facility), the patient's unique identifier is verified against the central database for a final status check. In some embodiments, when an approval code is found to be valid, the drug administration to the patient may proceed as described previously. In some embodiments, treatment-related adverse events are entered into the database.

In some embodiments, any one of the methods or systems described herein is computer-implemented. In some embodiments, the present invention also provides a computer-readable storage medium holding computer executable instructions for carrying out any of the methods or systems described herein.

In one embodiment, a method for providing a system of care for an oxazaphosphorine drug regimen includes any combination of the following steps prior to, and/or subsequently to, administration of the oxazaphosphorine drug regimen to the subject:

a. Registering a subject (also referred to herein as a patient) and generating a unique identifier for the patient in a computer-readable storage medium;

b. Providing counseling to the patient regarding the risks associated with the administration of the oxazaphosphorine drug regimen (e.g., high-dose oxazaphosphorine drug regimen), and obtaining the patient's informed consent for participation in the regimen;

c. Registering results in the computer-readable storage medium of one or more assays administered to the patient including, but not limited to:
  1) two independent pregnancy tests in the case of a female patient,
  2) a measure of the level or activity of Aldehyde Dehydrogenase (ALDH) enzyme in the patient's peripheral lymphocytes,
  3) a measure of the level or activity of ALDH enzyme in the patient's hematopoietic progenitor stem cells, a measure of the white blood cell (WBC) count of the patient prior to and after the oxazaphosphorine drug regimen,
  4) an assay (e.g., PCR assay) for detecting the presence of one or more viruses, such as herpesvirus (HSV), herpes simplex virus 1 (HSV-1), herpes simplex virus 2 (HSV-2), varicella-zoster virus (VZV). Epstein-Barr virus (EBV), cytomegalovirus (CMV), herpesvirus 6 (HHV-6), herpesvirus 7 (HHV-7), herpesvirus 8 (HHV-8; also known as Kaposi's sarcoma associated herpesvirus (KSHV), respiratory viruses (e.g., adenovirus, influenza, respiratory syncytial virus (RSV)), papopvavirus (e.g., papilloma, polyomavirus such as BKV and JCV), measles, hepatitis A (HAV), hepatitis B (HBV), hepatitis C(HCV), enterovirus, parvovirus, rabies virus, Rubella virus, Coxsackievirus, and human lymphotrophic virus,
  5) a measure of the QT/QTc interval,
  6) a platelet count,
  7) a neutrophil count, or any combination thereof;

d. Registering in the computer-readable storage medium all pharmaceuticals or substances, including supplements and drugs, currently being administered to the patient, and confirming in the storage medium that none of the pharmaceuticals or substances include contraindicated pharmaceuticals or substance (Contraindicated pharmaceuticals or substances include, for example:
  1) live virus vaccines, allopurinol, pentostatin, cyclosporine, St. John's Wort, etanercept, nevirapine, trastuzumab, ondansetron, succinylcholine, digoxin, chloramphenicol, indomethacin, or
  2) grapefruit products, such as dietary supplements that contain grapefruit bioflavonoids, or any combination thereof,
  3) ALDH modulating agents such as ALDH-inhibiting agents or inhibition factors (e.g., hormonal contraceptives in the case of high-dose oxazaphorine for autoimmune or transplant conditions) and ALDH-inducing agents or activation factors);

e. Computing an approval status code upon successful completion of steps a-d which corresponds to the patient's identifier within the storage medium;

f. Transmitting to the patient's care provider authorization to administer the oxazaphosphorine drug regimen to the patient based on the approval status code (Authorization includes, but is not limited to:
  1) a telephonic facsimile, paper, or Internet transmission of the patient's unique identifier,
  2) a telephonic facsimile, paper, or Internet transmission of the patient's unique identifier in combination with an approval code for dispensing the oxazaphosphorine drug to the patient,
  3) at least one dose of the oxazaphosphorine drug tagged with the patient's unique identifying information (ID code, e.g., a bar code), or any combination thereof);

g. Administering a suitable antiviral therapy such as gancyclovir for CMV if the PCR assay in step (c)(5) is positive for CMV infection;

In a further aspect, the invention includes any combination of the following steps after administration of the first dose of the oxazaphosphorine drug:

h. Monitoring the QT/QTc interval in the patient ensure cardiac safety during and following administration of the drug regimen;

i. Registering in the storage medium the administration of each dose of the oxazaphosphorine drug administered to the patient;

j. Registering in the storage medium any adverse events experienced by the patient in conjunction with the administration of the oxazaphosphorine drug;

k. Re-computing the approval code and transmitting the re-computed approval code to the care provider prior to administration of the next successive dose of the oxazaphosphorine drug to the patient (Re-computing is based upon an algorithm considering the number of doses received, known adverse events and the successful completion of all prophylactic and supportive care);

l. Administering to the patient one or more prophylactic drugs or pharmaceutical prior to, concurrent, or after administration of the oxaphosphorine regimen to the patient (including but not limited to antibacterials, antivirals, antifungals, mesna (e.g., intravenous or oral), or any combination thereof, and registering the administration of each of the prophylactic drugs in the storage medium);

m. Administering to the patient one or more biologics after administration of the oxaphosphorine regimen to the patient (such as granulocyte colony stimulating factor (G-CSF)), and registering the administration of each of the biologics in the storage medium;

n. Registering in the storage medium the administration to the patient of any necessary supportive care therapies including, but not limited to, post-therapy immunizations, platelet infusions, blood transfusions, red blood cell (RBC) infusions, or any combination thereof;

o. Registering the results in the storage medium of one or more assays administered to the patient (such as:
  1) disease-specific assays for markers of the unwanted immune disease, such as antibody counts,
  2) a measure of the WBC count of the patient,
  3) tests for serious infectious disease, including, but not limited to tuberculosis, HIV, and herpes,
  4) a measure of hepatic function, 5) a measure of the level of hematopoietic progenitor stem cell ALDH level or activity and/or peripheral lymphocyte ALDH level or activity,
6) tests for cardiovascular disease or insufficiency,
7) PCR blood draws for assessing the need for an antiviral (e.g., gancyclovir) to prevent CMV pneumonia, and
8) tests for allergy to any of the prophylactic drugs or biologics as administered, or any combination thereof).

It is to be understood that the steps need not be performed in the exact order listed herein. Additionally, one or more of the steps may be performed more than once, e.g., two, three, four or more times. Moreover, when a step is repeated, different variables may be used. For example, the methods of the present invention may include step (o)(2) and step (o)(7), which may occur simultaneously, consecutively or with one or more other steps in between.

By way of example, the method for providing a system of care for an oxazaphosphorine drug regimen may include the following aforementioned steps: step (a); or steps (a) and (b); or steps (a), (b), and (c); or steps (a), (b), (c), and (d); or steps (a), (b), (c), (d), (e), (f), and (g); or steps (a), (b), (c), (d), (e), (f), (g), and (h); or steps (a), (b), (c), (d), (e), (f), (g), (h), and (i); or steps (a), (b), (c), (d), (e), (f), (g), (h), (i), and (j); or steps (a), (b), (c), (d), (e), (f), (g), (h), (i), (j), and (k); or steps (a), (b), (c), (d), (e), (f), (g), (h), (i), (j), (k), and (l); or steps (a), (b), (c), (d), (e), (f), (g), (h), (i), (j), (k), (l), and (m); or steps (a), (b), (c), (d), (e), (f), (g), (h), (i), (j), (k), (l), (m), and (n); or steps (a), (b), (c), (d), (e), (f), (g), (h), (i), (k), (l), (m), (n), and (o), and so forth.

Figure 5:
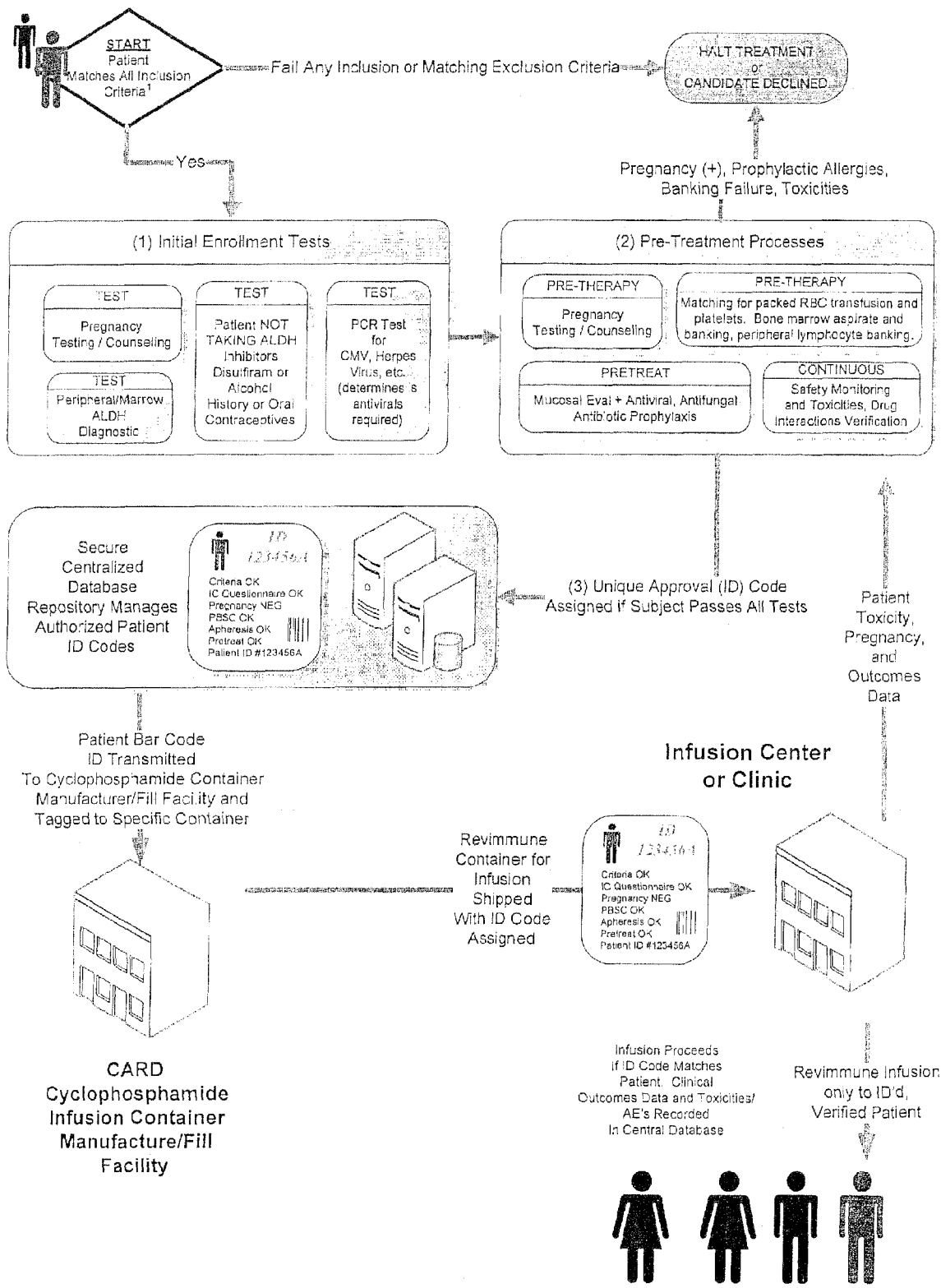
FIG. 5 is a schematic diagram of an exemplary system of care for an oxazaphosphorine drug regimen in accordance with the present invention, wherein Revimmune refers to high-dose oxazaphosphorine (e.g., high-dose cyclophosphamide).

FIG. 5 is a schematic diagram of an exemplary system of care for an oxazaphosphorine drug regimen in accordance with the present invention, wherein Revimmune refers to high-dose oxazaphosphorine (e.g., high-dose cyclophosphamide). Referring to FIG. 5, the patient is authorized for oxazaphosphorine therapy as follows: (1) validate the patient for the pre-treatment testing, including: pregnancy testing, peripheral lymphocyte ALDH quantification, bone marrow ALDH quantification, presence of ALDH inhibitors/activators, PCR test if needed for CMV/herpes/HIV/other viral infections, counseling, packed RBC transfusion and platelet preparation, mucosal evaluation and prophylaxis drug regimen preparation, and establish safety and adverse event monitoring and data gathering; (2) compute an approval code and/or register an approval code in the central database if any number or all of the above are met; (3) provide the authorization code to the drug manufacturer or fill facility; (4) print the authorization code on the drug container or packaging (this assigns the drug packaging to a specific patient; "patient-specific infusion package"); (5) ship the infusion package to the physician or infusion facility; (6) have the infusion facility or physician's office match the patient's personal information with the shipped infusion package's information (e.g., a barcode or other type of approval code printed or affixed on the specific drug packaging) prior to administering that package to the patient; and (7) submitting data to the central reporting database that the drug was infused and continuing with the prophylactic pre- and post-treatment drug regimen, as well as with adverse event and follow-up data gathering steps.

In an alternative embodiment from the steps shown in FIG. 5, the patient is authorized for oxazaphosphorine therapy by: (1) validating the patient for the pre-treatment testing, (2) computing an approval code and/or registering an approval code in the central database, (3) shipping the oxazaphosphorine drug to the physician or infusion facility, and (4) having the infusion facility or physician's office check with the database provider for the patient's status. Thus, the difference is in the authorization step, where instead of the container (e.g., bag or other container) being shipped on a per-patient basis, the drug is shipped as a generic container and then labeled with the patient's ID at the administration facility by the administering physician/staff member.

Radiological and Functional/Quality of Life Assessments

In some embodiments of the methods and systems of the invention, one or more radiological assessments (e.g., brain and/or spinal cord imaging) and/or functional or quality of life assessments are conducted on the patient. In some embodiments, the patient is suffering from a neurological autoimmune disorder, suspected of having a neurological autoimmune disorder, or at risk of developing a neurological autoimmune disorder, and it is to be determined whether treatment that includes oxazaphosphorine administration can be safe and effective for the patient based at least in part on the radiological assessment and/or functional assessment. Optionally, assessments may be made by a plurality of clinicians appropriate for the medical discipline and assessment (e.g., radiologists and/or neurologists).

Appropriate imaging modalities may be determined by those skilled in the art. Brain imaging techniques that may be utilized include, for example, different positron emission tomography (PET) and single photon emission tomography radiotracer methods; structural, functional, perfusion-weighted, or diffusion-weighted magnetic resonance imaging (MRI); x-ray computed tomography (CAT or CT scan); magnetic resonance spectroscopy measurements of N-acetyl aspartic acid, myoinositol, and other chemical compounds; electroencephalography, quantitative electroencephalography, event-related potentials, and other electrophysiological procedures; magnetoencephalography; and a combination of the foregoing. As an example, MRI can be used, for example, to detect and monitor T1 lesions, T2 lesions, gadolinium (gad)-enhancing lesions (GEL), and brain atrophy. In some embodiments, the patient undergoes fluid-attenuated inversion recovery (FLAIR) or T2-weighted MRI.

In some embodiments, the patient undergoes a brain MRI assessment, or radiological evaluation for brain volume (e.g., T2-weighted axial images can be used to calculate the parenchymal fraction in order to assess brain volume), or the patient undergoes an MRI assessment for the presence of GEL).

In some embodiments, the radiological assessment includes obtaining a brain or a spine radiological image or series of images (e.g., MRI, X-ray images, or CT), or data representative of the image (image data) from the patient.

In some embodiments, the patient undergoes a pre-treatment functional assessment or quality of life assessment such as the Expanded Disability Status Scale (EDSS), multiple sclerosis functional composite (MSFC) z-score, Scripps Neurologic Rating Scale (SNRS), Krupp Fatigue Severity Scale (FSS), Incapacity Status Scale (ISS), Functional Independence Measure (FIM), Ambulation Index (AI), Cambridge Multiple Sclerosis Basic Score (CAMBS), Functional Assessment of Multiple Sclerosis (FAMS), Profile of Mood States (POMS), Sickness Impact Profile (SIP), Guy's Neurological Disability Scale (GNDS), or a combination of two or more of the foregoing, and the results of this assessment are used to determine a patient's eligibility to receive treatment.

In some embodiments, the patient must satisfy one or more of the following criteria prior to receiving treatment with the oxazaphosphorine drug in order to be eligible for treatment:
  a. Males and females between the ages of 18 and 50 years, inclusive b. Diagnosis of clinically definite relapsing-remitting MS according to the McDonald Criteria.
c. 2 or more total gadolinium enhancing lesions on a brain and/or spinal cord MRI at screening
d. Subject must have had at least one clinical exacerbation within a year of initiating therapy.
e. Subject must have EDSS ranging from 1.5 to 6.5 inclusive; patients with EDSS ≥5.5 should have been sustained at that disability for ≤3 months.
f. Subject must have had a sustained (≥3 months) increase of >1.0 on the EDSS (historical estimate allowed) between 1.5 and 5.5 or >0.5 between 5.5 and 6.5 in the preceding year.
g. Written informed consent prior to any testing under this protocol, including screening tests and evaluations that are not considered part of the subject's routine care.
h. Women of childbearing potential should have a negative pregnancy test prior to entry into the study.
i. Subjects must have one of the following factors suggestive of a high risk for aggressive MS: one or more T1 hypointensities, OR sustained disability >3 months from an acute attack of greater than or equal to 3.0 OR optical coherence tomography (OCT) measurement of less than 80% of age matched controls in either eye In some embodiments, the patient must be excluded from receiving treatment if the patient meets any of the following conditions:
a. Cardiac ejection fraction of <45%;
b. Serum creatinine >2.0;
c. Patients who are pre-terminal or moribund;
d. Bilirubin >2.0, transaminases >2× normal;
e. Patients with pacemakers and implants who cannot get serial MRIs;
f. Patients with active infections until infection is resolved;
g. Patients with WBC count <3000 cells/µl, platelets <100,000 cells/µl and untransfused.

In some embodiments, the method of providing a system of care with an oxazaphosphorine drug regimen comprises carrying out one or more of the following steps prior to administration of the oxazaphosphorine drug regimen:
a. registering a subject and generating a unique identifier for the subject in a computerized storage medium;
b. providing counseling to the subject regarding the risks associated with the administration of the oxazaphosphorine drug regimen, and obtaining the subject's informed consent for participation in the regimen;
c. registering results in the storage medium of one or more assays administered to the subject including, but not limited to:
  1) two independent pregnancy tests in the case of a female subject,
  2) a measure of the level of aldehyde dehydrogenase (ALDH) enzyme in the subject's peripheral lymphocytes,
  3) a measure of the level of ALDH enzyme in the subject's hematogenous stem cells, a measure of the white blood cell (WBC) count of the subject prior to and after the oxazaphosphorine drug regimen,
  4) an assay (e.g., PCR assay) for detecting the presence of one or more viruses, such as herpesvirus (HSV), herpes simplex virus 1 (HSV-1), herpes simplex virus 2 (HSV-2), varicella-zoster virus (VZV), Epstein-Barr virus (EBV), cytomegalovirus (CMV), herpesvirus 6 (HHV-6), herpesvirus 7 (HHV-7), herpesvirus 8 (HHV-8; also known as Kaposi's sarcoma associated herpesvirus (KSHV), respiratory viruses (e.g., adenovirus, influenza, respiratory syncytial virus (RSV)), papovavirus (e.g., papilloma, polyomavirus such as BKV and JCV), measles, hepatitis A (HAV), hepatitis B (HBV), hepatitis C(HCV), enterovirus, parvovirus, rabies virus, Rubella virus, Coxsackievirus, and human lymphotrophic virus;
  5) a measure of the QT/QTc interval,
  6) a platelet count,
  7) a neutrophil count,
  8) a radiological assessment of the subject's brain volume,
  9) a radiological assessment of the presence of gadolinium-enhancing lesions in the subject,
  10) a functional disability evaluation score (such as EDSS or MSFC z-score),
  11) a record of the subject meeting the qualifying inclusion criteria,
  12) the absence of exclusion criteria, or any combination thereof,
d. registering in the storage medium all pharmaceuticals (e.g., supplements and drugs) currently being administered to the subject, and confirming in the storage medium that none of the pharmaceuticals include contraindicated pharmaceuticals or substances;
e. computing an approval status code upon successful completion of steps a-d which corresponds to the subject's identifier within the storage medium;
f. transmitting to the administration facility authorization to administer the oxazaphosphorine drug regimen to the subject based on the approval status code, or transmitting to the drug manufacturer authorization to release the oxazaphosphorine to the administration facility based on the approval status code; and
g. administering a suitable antiviral therapy such as gancyclovir for CMV if the assay in step (c)(4) is positive for CMV infection.

In some embodiments, the method of providing a system of care with an oxazaphosphorine drug regimen further comprises carrying out at least one of the following steps after administration of the first dose of the oxazaphosphorine drug:
h. monitoring the QT/QTc interval in the subject to ensure cardiac safety during and following administration of the drug regimen;
i. registering in the storage medium the administration of each dose of the oxazaphosphorine drug administered to the subject;
j. registering in the storage medium any adverse events experienced by the subject in conjunction with the administration of the oxazaphosphorine drug;
k. re-computing the approval code and transmitting the re-computed approval code to the care provider prior to administration of the next successive dose of the oxazaphosphorine drug to the subject;
l. administering to the subject one or more prophylactic drugs or pharmaceutical prior to, concurrent with, or after administration of the oxaphosphorine regimen to the subject (such as antibacterials, antivirals, antifungals, mesna, or any combination thereof), and registering the administration of each of the one or more prophylactic drugs or pharmaceutical in the storage medium;
m. administering to the subject one or more biologics after administration of the oxaphosphorine regimen to the subject (such as granulocyte colony stimulating factor (G-CSF)), and registering the administration of each of the biologics in the storage medium;
n. registering in the storage medium the administration to the subject of any necessary supportive care therapies (such as post-therapy immunizations, platelet infusions, blood transfusions, red blood cell (RBC) infusions, or any combination thereof);
o. registering the results in the storage medium of one or more assays administered to the subject;
p. registering in the storage medium a radiological assessment of the subject's brain volume;
q. registering in the storage medium a radiological assessment of the presence of gadolinium-enhancing lesions in the subject; or
r. registering in the storage medium any adverse events potentially disqualifying the subject from receiving further treatment.

In some embodiments of the method of providing a system of care with an oxazaphosphorine drug regimen, the one or more assays of (o) are selected from among:
1) disease-specific assays for markers of unwanted immune disease, such as antibody counts,
2) a measure of the WBC count of the subject,
3) tests for serious infectious disease (such as tuberculosis, HIV, and herpes),
4) a measure of hepatic function,
5) a measure of the level and/or activity of hematopoietic progenitor stem cell ALDH enzyme,
6) tests for cardiovascular disease or insufficiency,
7) PCR blood draws for assessing the need for an antiviral (such as gancyclovir) to prevent CMV pneumonia,
8) tests for allergy to any of the prophylactic drugs or biologics as administered,
9) a radiological assessment of the subject's brain volume,
10) a radiological assessment of the presence of gadolinium-enhancing lesions in the subject,
11) a functional disability score assessment (e.g., EDSS or MSFC z-score) to ensure the subject is within the prescribed range of allowable scores, or any combination thereof.

In some embodiments, prescribers, e.g., physicians, must be authorized in order to provide a subject with treatment. In some embodiments, pharmacies and/or pharmacists must be authorized in order to provide a subject or a physician with the oxazaphosphorine drug. In some embodiments, nurses and/or other practitioners must be authorized in order to administer the oxazaphosphorine drug. In some embodiments, any relevant staff associated with the physicians, pharmacies, pharmacists, nurses and/or other practitioners must also be authorized.

In some embodiments, "authorization" will require training of prescribers, physicians, pharmacies, pharmacists, nurses, other practitioners, and/or relevant staff associated therewith. In some embodiments, training includes providing information about the care system provided herein, the known risks associated with the regimen, the potential benefits of the regimen, appropriate use of the active, or any combinations thereof. In some embodiments, training includes providing information about adverse experience reporting procedures. In some embodiments, only prescribers, physicians, pharmacies, pharmacists, nurses, and other practitioners who complete such training will be considered "authorized." In some embodiments, prescribers, physicians, pharmacies, pharmacists, nurses, and other practitioners will be re-trained in given intervals, e.g., once every 6 months, 1 year, 2 years, 3 years, 4 years, 5 years, 6 years, 7 years, 8 years, 9 years, or 10 years. In some embodiments, only prescribers, physicians, pharmacies, pharmacists, nurses, and other practitioners who agree to comply with the system provided herein will be considered "authorized" to provide a subject with treatment.

In some embodiments, pharmacies will only be allowed to maintain a limited inventory of oxazaphosphorine drugs.

In some embodiments, only subjects who are registered in the system will be eligible for treatment with an oxazaphosphorine drug.

The specification is most thoroughly understood in light of the teachings of the references cited within the specification which are hereby incorporated by reference. The embodiments within the specification provide an illustration of embodiments in this application and should not be construed to limit its scope. The skilled artisan readily recognizes that many other embodiments are encompassed by this disclosure. All publications and patents cited and sequences identified by accession or database reference numbers in this disclosure are incorporated by reference in their entirety. To the extent that the material incorporated by reference contradicts or is inconsistent with the present specification, the present specification will supercede any such material. The citation of any references herein is not an admission that such references are prior art to the present specification.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention will be further described in the following examples, which are not meant to limit the scope of the invention in any way.

EXAMPLES

Example 1

Correlation of Aldehyde Dehydrogenase Activity, White Blood Cell Count, and High-Dose Oxazaphosphorine Treatment Resistance Nine patients were treated 50 mg/kg/day cyclophosphamide intravenously for four days (on Day-3 to Day 0). All 9 patients had aggressive relapsing-remitting multiple sclerosis, 8 of whom failed conventional therapy and 1 was untreated. Median age at time of entry was 29 years (range of 20 to 47 years). The mean number of gadolinium enhancing lesions on baseline MRI was 6.5 (range 3-11). There was a 90% reduction in gadolinium enhancements at 6 months and subsequently a 94% reduction by 18 months following high-dose cyclophosphamide treatment. Only one patient had an exacerbation during follow-up and was started on conventional MS therapy at 18 months. At baseline, 66% of patients had a disability score of 5.0 or more on the Expanded Disability Status Scale (EDSS). A 50% reduction in disability was observed with 3 patients having no disability (EDSS score of 0) and 1 patient with EDSS score of 1. This response rate (reduction of disability) is unprecedented. Similar results have been independently confirmed; however, those patients were more advanced in their disease and the absolute reduction in disability was less (Gladstone D E et al., *Arch Neurol,* 2006, 63(10):1388-1393).

In the pilot study with an initial cohort of 9 patients with severe relapsing MS, there have been no significant adverse outcomes. It appears that the dose of cyclophosphamide has variable effects in individual subjects in terms of the ability of high-dose cyclophosphamide treatment to reduce the patient's white blood cell (WBC) count to 0. This appeared to affect the long-term outcome with respect to the potential for disease reactivation (as measured by the recurrence of gadolinium enhancing lesions).

On Day 6, (six days after completion of high-dose cyclophosphamide treatment), patients received G-CSF. FIG. 1 is a table showing ALDH levels and WBC levels in the 9 human patients with aggressive relapsing-remitting MS that received 50 mg/kg/day cyclophosphamide intravenously on Day-3 to Day-0.

The two patients whose WBC count went to 0 within two weeks of high-dose cyclophosphamide treatment (HiCy05 and HiCy13) had no gadolinium enhancing lesions (GEL) up to 24 months follow-up (FUGEL). Two additional patients (HiCy09 and HiCy15) had 0 GEL and both had a minimum WBC count of 12. Patients who always had GEL on every follow up (HiCy11 and HiCy19) never went to a 0 WBC count (minimum WBC counts were 24 and 50, respectively). However, HiCy19 had only completed 6 months of follow-up. Patients HiCy07 and HiCy14, who went to 0 GEL but on follow-up magnetic resonance imagings (MRIs) had a single GEL, had variable minimum WBC (6 and 31). HiCy01, whose minimum WBC was 70 and never had GEL did not have any GEL at subsequent follow-up visits. This patient had been hospitalized several times with new, acute worsening of his neurologic status that was highly suspicious of exacerbations (even prompting rituxan treatment) despite no GEL.

As shown in the table of FIG. 2, Spearman's correlation coefficient of geometric ALDH levels and the 6 day average minimal WBC level was 0.800 with a p value of 0.010 (highly statistically significant). This represents the average ALDH activity in peripheral blood mononuclear cells (PBMC) from the 9 patients in the study, which was ascertained using ALDEFLUOR™ and fluorescence activated cell sorting (FACS) to identify the contribution of only CD4-positive cells. CD8-positive T cells showed no correlation in ALDH levels and mean minimal WBC count.

FIG. 3 is a plot of Spearman P-values (upper right) for ALDH versus CD4 vs. CD8 vs. Nadir WBC (6-day). The upper right panel compares geometric ALDH to the 6-day nadir WBC, with a p-value of 0.014. The lower left panels are scatter plots of ALDH versus WBC, matching the corresponding panels with the p-values.

Figure 4:
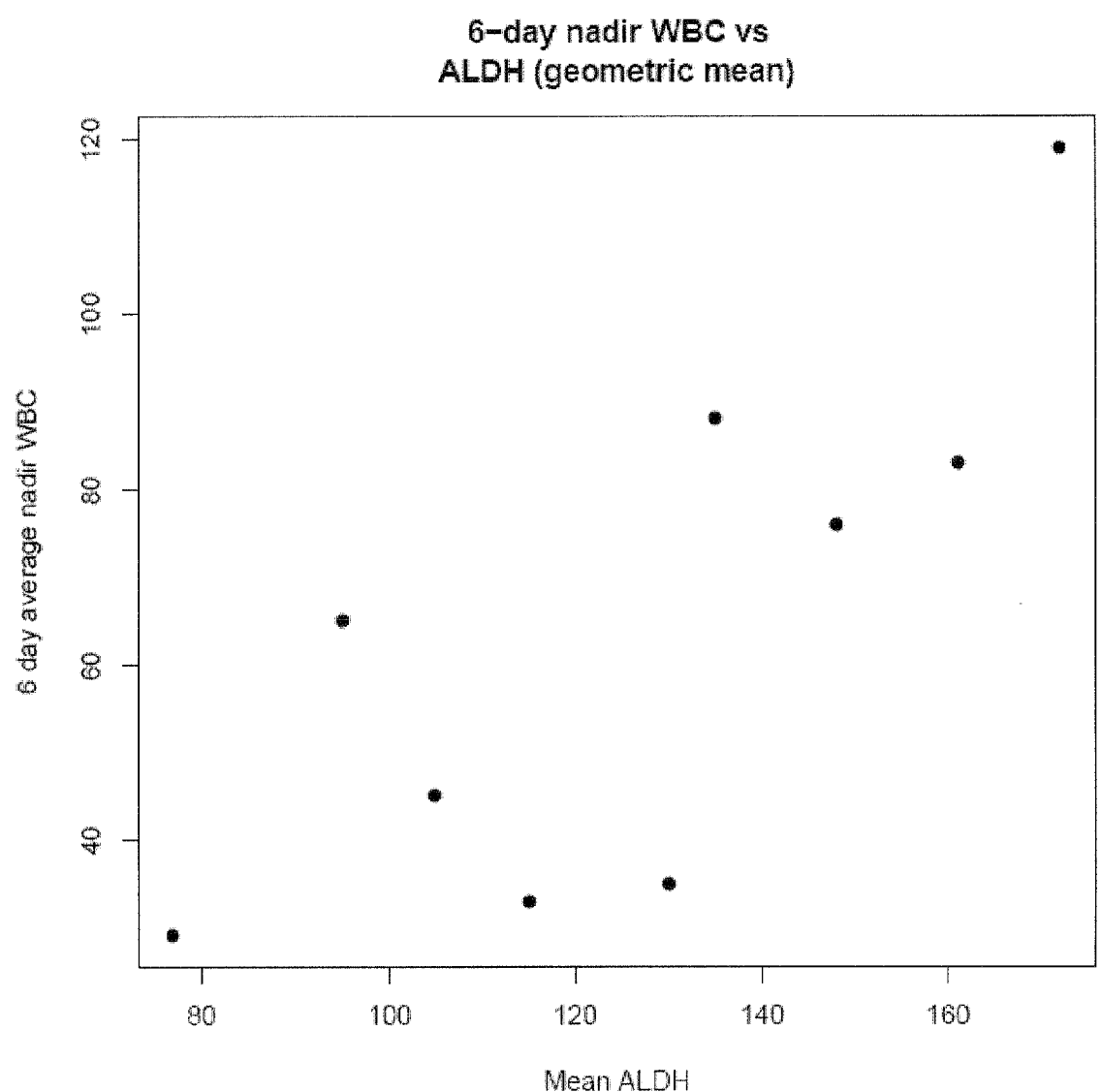
FIG. 4 is a scatter plot of 6-day Nadir WBC vs. ALDH (geometric mean).

FIG. 4 is a scatter plot of 6-day Nadir WBC vs. ALDH (geometric mean).

What is claimed is:

1. A method of providing a system of care with a high-dose oxazaphosphorine drug regimen to treat or delay the onset of transplant rejection, comprising, carrying out the following steps prior to administration of the high-dose oxazaphosphorine drug regimen:
   a. registering a subject and generating a unique identifier for the subject in a non-transitory computerized storage medium;
   b. providing counseling to the subject regarding the risks associated with the administration of the high-dose oxazaphosphorine drug regimen, and obtaining the subject's informed consent for participation in the regimen;
   c. registering one or more of the following items in the storage medium:
      1) results of two independent pregnancy tests from the subject in the case of a female subject,
      2) a measure of the level of aldehyde dehydrogenase (ALDH) enzyme in the subject's peripheral lymphocytes,
      3) a measure of the level of ALDH enzyme in the subject's hematogenous stem cells,
      4) a measure of the white blood cell (WBC) count of the subject prior to and after the high-dose oxazaphosphorine drug regimen,
      5) result of an assay for detecting the presence of one or more viruses in the subject;
      6) a measure of the QT/QTc interval of the subject,
      7) a platelet count from the subject,
      8) a neutrophil count from the subject,
      9) a record of the subject meeting the qualifying inclusion criteria, or
      10) the absence of exclusion criteria, or a combination of any of the foregoing,
   d. registering in the storage medium all pharmaceuticals or other substances currently being administered to the subject, and confirming in the storage medium that none of the pharmaceuticals include contraindicated pharmaceuticals or substances;
   e. computing an approval status code upon successful completion of steps a-d which corresponds to the subject's identifier within the storage medium; and
   f. transmitting to an administration facility authorization to administer the high-dose oxazaphosphorine drug regimen to the subject based on the approval status code, or transmitting to the drug manufacturer authorization to release the oxazaphosphorine of the high-dose oxazaphosphorine regimen to the administration facility based on the approval status code, causing the administration facility to administer the high-dose oxazaphosphorine drug regimen to the subject based on the approval status code, to treat or delay the onset of transplant rejection.

2. The method of claim 1, wherein transmitting of (f) comprises transmitting the approval status code to the drug manufacturer or administration facility, and wherein the approval status code is affixed to, or otherwise associated with, a container containing the oxazaphosphorine.

3. The method of claim 2, wherein the approval status code comprises a bar code or other identifier specific to the subject.

4. The method of claim 1, wherein the high-dose oxazaphosphorine drug regimen comprises administration of a first dose of the oxazaphosphorine drug to the subject, and wherein said method further comprises carrying out at least one of the following steps after administration of the first dose of the oxazaphosphorine drug to the subject:
   g. monitoring the QT/QTc interval in the subject to ensure cardiac safety during and following administration of the drug regimen;
   h. registering in the storage medium the administration of each dose of the oxazaphosphorine drug administered to the subject;
   i. registering in the storage medium any adverse events experienced by the subject in conjunction with the administration of the oxazaphosphorine drug;
   j. re-computing the approval code and transmitting the re-computed approval code to the care provider prior to administration of the next successive dose of the oxazaphosphorine drug to the subject;
   k. administering to the subject one or more prophylactic drugs or pharmaceuticals prior to, concurrent with, or after administration of the oxazaphosphorine regimen to the subject, and registering the administration of each of the one or more prophylactic drugs or pharmaceuticals in the storage medium;

l. administering to the subject one or more biologics after administration of the oxazaphosphorine regimen to the subject, and registering the administration of each of the biologics in the storage medium;

m. registering in the storage medium the administration to the subject of any necessary supportive care therapy;

n. registering the results in the storage medium of one or more assays administered to the subject; or o. registering in the storage medium any adverse events potentially disqualifying the subject from receiving further treatment.

5. The method of claim 4, wherein the contraindicated pharmaceutical or other substance of (d) is one or more among: live virus vaccines, allopurinol, pentostatin, cyclosporine, St. John's Wort, etanercept, nevirapine, trastuzumab, ondansetron, succinylcholine, digoxin, chloramphenicol, and indomethacin.

6. The method of claim 1, wherein the contraindicated pharmaceutical or substance of (d) is one or more grapefruit products.

7. The method of claim 1, wherein the contraindicated pharmaceutical or other substance of (d) is one or more ALDH inhibition factors, one or more ALDH activation factors, or both.

8. The method of claim 7, wherein the one or ALDH inhibition factors includes at least one selected from the group consisting of hormonal contraceptive use, tobacco use, chronic alcohol consumption, and any combinations thereof.

9. The method of claim 7, wherein the one or more ALDH inhibition factors includes at least one ALDH inhibition agent selected from the group consisting of disulfiram, hormonal contraceptive, procarbazine, N-methyltetrazolylthiomethyl bearing beta-lactam, kudzu root product, calcium carbimide, diazepam, chlordiazepoxide, isosorbide dinitrate, nitroglycerine, chlorpropamide, tolazamide, and cephalosporin, or an ALDH inhibiting metabolite thereof.

10. The method of claim 7, wherein the one or more ALDH inhibition factors are one or more anti-cancer agents, antibiotics, or dietary supplements.

11. The method of claim 7, wherein the one or more ALDH inhibition factors are one or more irreversible inhibitors of ALDH.

12. The method of claim 7, wherein the one or more ALDH activation factors are one or more ALDH activation agents selected from the group consisting of coffee, oltipraz, *Crucifera* vegetable family member, Liliaceae vegetable family member, and Phenobarbital, or an ALDH activating metabolite of any of the foregoing.

13. The method of 1, wherein the authorization of (f) is selected from at least one of the following:
1) a telephonic facsimile, paper, or Internet transmission of the subject's unique identifier,
2) a telephonic facsimile, paper, or Internet transmission of the subject's unique identifier in combination with an approval code for dispensing the oxazaphosphorine drug to the subject,
3) at least one dose of the oxazaphosphorine drug in a container affixed or otherwise associated with the subject's unique identifying information, or any combination thereof.

14. The method of claim 4, wherein re-computing of (k) is based upon an algorithm considering the number of doses received, known adverse events and the successful completion of all prophylactic and supportive care.

15. The method of claim 4, wherein the one or more assays of (n) are selected from among:
1) disease-specific assays for markers of unwanted immune disease,
2) a measure of the WBC count of the subject,
3) a test for serious infectious disease,
4) a measure of hepatic function,
5) a measure of the level and/or activity of hematopoietic progenitor stem cell ALDH enzyme,
6) tests for cardiovascular disease or insufficiency,
7) PCR blood draws for assessing the need for an antiviral to prevent CMV pneumonia,
8) tests for allergy to any of the prophylactic drugs or biologics as administered, or any combination thereof.

16. The method of claim 1, wherein the transplant rejection is from a bone marrow transplant.

17. The method of claim 16, wherein the transplant rejection is graft-versus-host disease.

18. The method of claim 1, wherein the transplant is for treatment of a hereditary hemoglobinopathy.

19. The method of claim 1, wherein the high-dose oxazaphosphorine drug regimen comprises administration of 200 mg/kg oxazaphosphorine drug intravenously.

20. The method of claim 1, wherein the high-dose oxazaphosphorine drug regimen comprises intravenous administration of about 40 mg/kg to about 50 mg/kg in divided doses over a period of from about 2 to about 5 days.

21. The method of claim 1, wherein the oxazaphosphorine of the high-dose oxazaphosphorine drug regimen is selected from the group consisting of cyclophosphamide, ifosfamide, perfosfamide, trophosphamide, 4-hydroxycyclophosphamide, aldophosphamide, and a pharmaceutically acceptable salt, solvate, prodrug, or active metabolite of any of the foregoing.

22. A non-transitory computer-readable storage medium holding computer executable instructions to carry out the steps of the method of claim 1.

23. The storage medium of claim 22, wherein the storage medium is selected from an application specific integrated circuit (ASIC), a compact disc (CD), a digital video disk (DVD), a random access memory (RAM), a read only memory (ROM), a disk, memory stick, hard disk, or CD-ROM.

24. The method of claim 1, wherein the storage medium is selected from an application specific integrated circuit (ASIC), a compact disc (CD), a digital video disk (DVD), a random access memory (RAM), a read only memory (ROM), a disk, memory stick, hard disk, or CD-ROM.

25. The method of claim 1, wherein the assay for detecting the presence of one or more viruses in (c)(5) is for the detection of CMV infection, and wherein said method further comprises administering a suitable antiviral therapy for CMV if the assay in step (c)(5) is positive for CMV infection.

26. The method of claim 1, further comprising step (g) providing an amount of the oxazaphosphorine drug of the high-dose oxazaphosphorine drug regimen to the administration facility for administration to the subject.

27. The method of claim 1, wherein the high-dose oxazaphosphorine drug regimen comprises administration of 50 mg/kg/day of the oxazaphosphorine drug intravenously, for four consecutive days.

28. The method of claim 17, wherein the transplant is for treatment of a hematologic malignancy.

29. The method of claim 1, wherein the method comprises (c)(2): registering in the storage medium a measure of the level of ALDH enzyme in the subject's peripheral lymphocytes.

30. The method of claim 1, wherein the method comprises (c)(3): registering in the storage medium a measure of the level of ALDH enzyme in the subject's hematogenous stem cells.

31. The method of claim 1, wherein the method comprises (c)(4) registering in the storage medium a measure of the WBC count of the subject prior to and after the high-dose oxazaphosphorine drug regimen.

32. The method of claim 1, wherein the method comprises:
   (c)(2): registering in the storage medium a measure of the level of ALDH enzyme in the subject's peripheral lymphocytes;
   (c)(3): registering in the storage medium a measure of the level of ALDH enzyme in the subject's hematogenous stem cells; and
   (c)(4) registering in the storage medium a measure of the WBC count of the subject prior to and after the high-dose oxazaphosphorine drug regimen.

* * * * *

UNITED STATES PATENT AND TRADEMARK OFFICE
CERTIFICATE OF CORRECTION

PATENT NO. : 9,026,372 B2
APPLICATION NO. : 12/789401
DATED : May 5, 2015
INVENTOR(S) : O'Donnell, Jr. et al.

Page 1 of 1

It is certified that error appears in the above-identified patent and that said Letters Patent is hereby corrected as shown below:

Title Page of Patent:

"(73) Assignee: Accentia Biopharmaceuticals, Inc., Tampa, FL (US)"

should read

--(73) Assignee: Pabeti, Inc., Marion, IL (US)--

Signed and Sealed this
Seventeenth Day of May, 2016

Michelle K. Lee
*Director of the United States Patent and Trademark Office*